United States Patent [19]

Ryer et al.

[11] Patent Number: 5,242,612
[45] Date of Patent: Sep. 7, 1993

[54] MIXED PHOSPHOROUS- AND SULFUR-CONTAINING REACTION PRODUCTS USEFUL IN POWER TRANSMITTING COMPOSITIONS

[75] Inventors: Jack Ryer, East Brunswick; Antonio Gutierrez, Mercerville; James S. Puckace, Freehold; Raymond F. Watts, Long Valley; Stanley J. Brois, Westfield; Craig W. Gleason, Scotch Plains, all of N.J.

[73] Assignee: Exxon Chemical Patents Inc., Linden, N.J.

[21] Appl. No.: 370,315

[22] Filed: Jun. 22, 1989

Related U.S. Application Data

[63] Continuation-in-part of Ser. No. 210,831, Jun. 24, 1988, abandoned.

[51] Int. Cl.$^5$ ................ C10M 135/00; C10M 137/00
[52] U.S. Cl. .................................... 252/46.7; 252/46.6
[58] Field of Search .......................... 252/46.6, 46.7

[56] References Cited

U.S. PATENT DOCUMENTS

| | | | |
|---|---|---|---|
| 2,230,966 | 2/1941 | Reid et al. | 252/45 |
| 2,290,880 | 7/1942 | Katzman et al. | 260/584 |
| 2,346,154 | 4/1944 | Denison, Jr. et al. | 252/38 |
| 2,522,512 | 9/1950 | Harman et al. | 200/609 |
| 2,562,144 | 7/1951 | Harman et al. | 252/48.2 |
| 2,566,157 | 8/1951 | Barker | 252/34.7 |
| 2,582,605 | 1/1952 | Richter et al. | 260/608 |
| 2,721,177 | 10/1955 | Harle | 252/47.5 |
| 2,750,342 | 6/1956 | Mikeska et al. | 252/46.6 |
| 2,874,192 | 2/1959 | Cottle et al. | 260/609 |
| 2,960,523 | 11/1960 | O'Brien | 260/461 |
| 3,034,907 | 5/1962 | Kleemann et al. | 106/14 |
| 3,135,804 | 6/1964 | von Brachel et al. | 260/609 |
| 3,235,501 | 2/1966 | Waldmann | 252/49.6 |
| 3,254,025 | 5/1966 | Le Suer | 252/32.7 |
| 3,335,189 | 8/1967 | Degener et al. | 568/45 |
| 3,426,075 | 2/1969 | Campbell | 252/45 |
| 3,446,738 | 5/1969 | Chao et al. | 252/46.7 |
| 3,450,771 | 6/1969 | Dombro | 568/38 |

(List continued on next page.)

FOREIGN PATENT DOCUMENTS

WO88/09804 12/1988 World Int. Prop. O. .

OTHER PUBLICATIONS

Journal of Polymer Science vol. XII 219–223, pp. 231–239 (1959).
"The Condensation of 2-Hydroxyethyl Sulfides with Alcohols and Phenols" pp. 4076–4079 Richter et al.
Fokin, A. V., "Nucleophilic Substitution of Hydroxyl Groups in 2-Alkyl(Aryl)-Thioethanols".

*Primary Examiner*—Ellen McAvoy
*Attorney, Agent, or Firm*—R. A. Maggio

[57] ABSTRACT

A phosphorous- and sulfur-containing additive and its use to impart anti-wear properties to oleaginous compositions such as fuels and lubricating oils, particularly power transmission compositions, such as automatic transmission fluids, is disclosed. The additive comprises a mixture of products formed, for example, by simultaneously reacting (1) a beta-hydroxy thioether, such as thiobisethanol, (2) a phosphorous-containing reactant, such as triethyl phosphite and (3) optionally, a nucleophilic reactant capable of reacting with the episulfonium cation

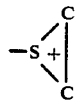

to form thioether species.

169 Claims, 6 Drawing Sheets

U.S. PATENT DOCUMENTS

| | | | |
|---|---|---|---|
| 3,502,677 | 3/1970 | Le Suer | 544/243 |
| 3,509,052 | 4/1970 | Murphy | 252/34.7 |
| 3,660,497 | 5/1972 | Priestley et al. | 568/45 |
| 3,705,139 | 12/1972 | Yamane et al. | 524/173 |
| 3,933,659 | 1/1976 | Lyle et al. | 252/32.7 |
| 4,031,203 | 6/1977 | Musser et al. | 252/48.2 |
| 4,081,387 | 3/1978 | Ripple | 252/46.6 |
| 4,129,508 | 12/1978 | Friihauf | 252/33 |
| 4,170,560 | 10/1979 | Lowe | 252/47.5 |
| 4,201,684 | 5/1980 | Malec | 252/47.5 |
| 4,217,233 | 8/1980 | Michaels | 252/48.2 |
| 4,231,883 | 11/1980 | Malec | 252/33.4 |
| 4,366,307 | 12/1982 | Singh et al. | 528/373 |
| 4,382,006 | 5/1983 | Horodysky | 252/49.6 |
| 4,477,362 | 10/1984 | Steckel | 252/51.5 R |
| 4,511,480 | 4/1985 | Outlaw et al. | 252/8.55 |
| 4,579,672 | 4/1986 | Brecker et al. | 252/49.8 |
| 4,615,818 | 10/1986 | DiBiase et al. | 252/47.5 |
| 4,664,826 | 5/1987 | Gutierrez et al. | 252/482 |
| 4,681,694 | 7/1987 | Zoleski et al. | 252/51.5 R |
| 4,702,850 | 10/1987 | Gutierrez et al. | 252/48.2 |
| 4,704,217 | 11/1987 | Sweeney et al. | 52/32.7 E |
| 4,752,416 | 6/1988 | Scharf et al. | 252/78.5 |
| 4,764,299 | 8/1988 | Salomon | 252/48.2 |
| 4,769,164 | 9/1988 | Salomon | 252/48.2 |
| 4,776,969 | 10/1988 | Ryer et al. | 252/46.7 |

31P NMR SPECTRA

31P NMR SPECTRA

31P NMR SPECTRA

31P NMR SPECTRA

31P NMR SPECTRA

MIXED PHOSPHOROUS- AND SULFUR-CONTAINING REACTION PRODUCTS USEFUL IN POWER TRANSMITTING COMPOSITIONS

RELATED APPLICATION

This application is a continuation-in-part of Ser. No. 210,831, filed Jun. 24, 1988, now abandoned the disclosure of which is incorporated herein by reference.

BACKGROUND OF THE INVENTION

The present invention relates to a hydrocarbon or dispersible mixture of phosphorous- and/or sulfur-containing reaction products, their method of preparation, and their utility as antiwear and anti-oxidation additives for oleaginous compositions such as fuel oils, lubricating oils, including power transmission fluids and crankcase oils, and to the oleaginous compositions in which they are contained.

The lubrication of modern mechanical equipment requires that the lubricating oil possess excellent resistance to oxidation as well as the ability to protect metal surfaces in sliding or rolling contact from wear. These properties are vital to the success of any lubricating oil. Additives which improve the resistance of base lubricating oils to oxidation and extend the life of the equipment are of great importance.

Oxidation in lubricating oils manifests itself as an increase in acidity of the oil, increase in oil viscosity, and formation of insoluble products which appear as a sludge. Acidity in the oil is detrimental as it eventually leads to attack of the metal parts in the form of rusting or corrosion. Parts made of the yellow metals, copper, brass and bronze are especially susceptible to this type of attack. Increasing oil viscosity adversely effects the efficiency of the equipment and can lead to the inability to circulate the lubricant through the mechanism. Formation of sludge causes deposits in oil sumps and reservoirs. These deposits, if formed in small lubricant passageways or channels, can block lubricant flow. Excessive viscosity increase or sludge formation can cause failure due to lubricant starvation.

Wear results from the contact of metal surfaces in motion relative to each other. Under low loads and at high relative speeds hydrodynamic lubrication predominates. That is, the two metal parts are separated by a film of oil. This type of lubrication predominates in journal bearings. At higher loads or lower speeds the oil film fails and boundary lubrication becomes the main mechanism of lubrication. In boundary lubrication the two metal surfaces are separated only by a film of chemical additives. Gears operate in boundary lubrication mode. It is highly desirable that lubricating oils contain additives to provide for boundary lubrication conditions.

Control of friction is also possible through modifying the lubricating oil with additives. It is often desirable to modify the frictional performance of a lubricating oil but not necessarily to minimize it. For example, a specialized property sought to be imparted to certain lubricating oil compositions adapted for use as automatic transmission fluids and tractor hydraulic fluids is the ability to control friction to very exacting requirements. These requirements are set forth by the manufacturers of the equipment. This property distinguishes automatic transmission fluids (ATF's) and tractor hydraulic fluids (THF's) from other lubricants; and in fact, there is further differentiation between types of ATF's and THF's.

Such characteristic quality has received the most attention by both the transmission manufacturers and fluid producers for many years. The attention stems from the fact that the friction requirements of these fluids are unique and depend on the transmission and clutch or brake design, as well as on the type of friction materials used.

As is also well known, oxidation, wear and friction can be controlled through the addition of suitable additives with varying degrees of success.

While there are many known additives which may be classified as anti-wear, or friction modifying agents, it is also well known that many of these additives act in a different physical or chemical manner and often compete with one another, e.g. they may compete for the surface of the moving metal parts which are subjected to lubrication. Accordingly, extreme care must be exercised in selection of these additives to insure compatibility and effectiveness.

Both anti-wear and friction modifying agents function by forming a coating on the surface of the moving parts. The coating may be physically adsorbed or it may actually be bonded chemically to the surface. Consequently, if the association between the anti-wear agent and the metal part is stronger than the association between the friction modifying agent and the metal part, the anti-wear agent will displace the friction modifying agent at the metal surface, i.e. at the metal/fluid interface, and friction control will be lost.

Various tests have been designed by automatic transmission manufacturers for measuring ATF friction and anti-wear properties. These tests are used to evaluate the performance of additives and fluids in view of the requirements of particular transmission designs and their ability to impart transmission durability and smooth shifting under a variety of road conditions.

Frictional performance is typically evaluated on an SAE No. 2 friction apparatus. In this test, a test head containing a test clutch pack and the fluid is fitted to an electric motor with an inertia disc. The motor and flywheel of the friction machine (filled with fluid to be tested) are accelerated to constant speed, the motor is shut off and the flywheel speed is decreased to zero by application of the clutch. The clutch plates are then released, the system is again accelerated to constant speed, and the clutch pack which is immersed in the test fluid is engaged again. This process is repeated many times with each clutch engagement being called a cycle.

During the clutch application, friction torque is recorded as a function of time. The friction data obtained are either the torque traces themselves or friction coefficients calculated from the torque traces. The shape of the torque trace desired is set by the auto manufacturers. One way of characterizing this friction performance is to determine the torque: (a) when the flywheel speed is midway between the maximum constant speed selected and zero speed (such torque measurement is referred to herein as $T_D$) and (b) when as the flywheel speed approaches zero rpm (such torque measurement is referred to herein as $T_0$). Such torques can then be used to determine the torque ratio which is expressed as $T_0/T_D$, or alternatively, to determine the torque differential $T_0-T_D$. The optimum target values for torque ratio and torque differential are set by the auto manufacturers. As the $T_0/T_D$ increasingly exceeds 1, a transmission will typically exhibit shorter harsher shifts as it changes gears. On the other hand as $T_O/T_D$ decreases below 1, there is an increasingly greater danger of clutch slippage when the transmission changes gears. Similar relationships exist with respect to a $T_O-T_D$ target value of 0.

While many automatic transmission fluids can achieve target values of $T_O/T_D$ after a minimum number of cycles, it becomes increasingly more difficult to sustain such target values as the number of cycles are increased. The ability of an ATF to sustain such desired friction properties is referred to herein as friction stability or durability. A high level of friction stability is difficult to achieve with ATFs containing certain anti-wear agents. It is believed that as the ATF ages under the influence of the heat of friction, the anti-wear agent can break down and the decomposition products displace conventional friction modifiers at the metal/fluid interface. As a result, the fluid may exhibit varying friction properties.

Attempts to improve friction stability by simply adding more friction modifier have not met with success because this tends to reduce the breakaway static torque $(T_S)$ of the fluid. This parameter when expressed as the breakaway static torque $(T_S)$ reflects the relative tendency of engaged parts, such as clutch packs, bands and drums, to slip under load. If this value is too low, the slippage can impair the driveability and safety of the vehicle.

Transmission designs have undergone radical changes, thereby necessitating the formulation of ATF additives capable of meeting new and more stringent requirements needed to match such design changes.

No base oil alone can even approach the many special properties required for ATF service. Therefore, it is necessary to employ several chemical additives, each of which is designed to impart or improve a specific property of the fluid. Consequently, it becomes particularly advantageous when one additive can perform more than one function, thereby reducing the number of additives needed to be present in the formulation.

Accordingly, there has been a continuing search for new additives possessed of one or more properties which render them suitable for use in ATF compositions, as well as other oleaginous compositions. There also has been a search for new combinations of additives which not only provide ATF compositions, as well as other oleaginous compositions, with the various specific properties that are required, but which are compatible with each other in the sense that they do not exhibit any substantial tendency to compete with each other, nor to otherwise reduce the effectiveness of the various additives in the compositions. The present invention was developed in response to this search.

U.S. Pat. No. 2,230,966 relates to stabilization of petroleum oils against oxidation by using thiosubstituted alkyl thio ethers of the general structure:

$$R'(SCR_2(CR_2)_n)_xS((CR_2)_mCR_2S)_yR'$$

wherein R represents hydrogen or an alkyl radical; wherein R' represents hydrogen or an alkyl, or aryl or an alkaryl radical (both R' need not be the same), wherein m, n, x and y are whole numbers. These materials are prepared by reaction of alkyl halides and alkyl di-halides with sodium sulfide. No oxygen containing analogues are included.

U.S. Pat. No. 2,346,154 relates to hydrocarbon oil compositions which contain a metal phenate stabilizer, a polyvalent metal salt of an acid of phosphorous containing an organic substituent and a thioether sensitizer which enhances the responsiveness of the hydrocarbon oil to stabilization by the phenate and salt. The thioether sensitizer is claimed as having the structural formula:

$$R\text{-}S\text{-}R_1$$

or the structural formula:

$$R\text{-}S\text{-}CC\text{-}S\text{-}R_1$$

wherein R and $R_1$ are alkyl radicals, wherein at least one of R and $R_1$ contains more than about ten carbon atoms, and wherein the sum of the sum of the number of carbon atoms in R and $R_1$ is at least about twelve.

U.S. Pat. No. 2,522,512 relates to a process for preparing non-mineral oil base sulfur containing lubricating compositions, wherein a sulfur compound is mixed with a dialkenylether and heated in the presence of a minor amount of a catalyst to form a mixture of polymeric linear adducts of the reactants, and wherein the fraction which volatilizes below 160° C. at 1 cm. mercury pressure is recovered from the polymeric adducts as product. The sulfur compound has the general formula:

$$R\text{-}S\text{-}R$$

wherein both R's are selected from the group consisting of hydrogen atoms and alkyl radicals, and at least one R is a hydrogen atom. The catalyst is selected from the group consisting of dialkylperoxides and alkyl hydroperoxides. The polymeric product contains compounds having units of the general configuration $$\text{-}S\text{-}R\text{-}X\text{-}R\text{-}$$

wherein X is either S or O, depending upon whether an ether or thioether reactant was used, and each R is an organic radical, preferably a saturated hydrocarbon radical.

U.S. Pat. No. 2,562,144 discloses lubricating compositions containing one or more reaction products. One of the reactants is a polyether of the general formula $$R_1[O\text{—}R\text{-}S\text{-}R]_n\text{—}O\text{—}R_2$$

wherein $R_1$ and $R_2$ are mercaptoalkyl or alkenyl groups and R is a saturated hydrocarbon.

U.S. Pat. No. 2,566,157 discloses a lubricant having as the major ingredient thereof mixed partially isomeric triple ethers of the general formula:

$$A\text{-}S\text{-}B\text{—}O\text{—}B'\text{-}S\text{-}A'$$

wherein A, A', B and B' are saturated $C_2$–$C_{18}$ aliphatic groups. The lubricant also contains a resin such as a polystyrene or acrylic resin, and an aralkyl ester ingredient which is intersoluble with the triple ether ingredient and a solvent of the resin.

U.S. Pat. 2,582,605 relates to a process for producing long chain sulfur and oxygen containing polyethers by reacting beta-hydroxyethyl sulfides with alcohols. The process consists of reacting any compound with the functional grouping—$SCH_2CH_2OH$ with a hydroxy or polyhydroxy compound in the presence of a strong acid catalyst, preferably sulfuric acid or catalysts which may be considered as being derived from sulfuric acid, e.g. the aryl sulfonic acids or alkyl sulfonic acids (see Col. 8, lines 2-35). The reactions disclosed in this patent are carried out at elevated temperatures being about 130° and 200° C., and preferably between about 140° C. and 160° C.

U.S. Pat. No. 2,721,177 relates to poly-oxyalkylene glycol lubricating oil compositions having improved stability towards oxidative deterioration. The compositions include an aromatic primary oxidation inhibitor and a secondary or auxiliary sulfur-containing oxidation inhibitor. The sulfur-containing inhibitor is characterized by the formula:

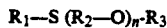

$R_1-S-(R_2-O)_n-R_3$ wherein $R_1$ is a $C_1-C_{20}$ alkyl group, $R_2$ is an ethylene or 1,2-propylene alkylene group, $R_3$ is H, and n is an integer designating the number of alkylene oxide groups. Typically, the average molecular weight of the sulfur-containing secondary inhibitor is between about 250 and 2000.

U.S. Pat. No. 2,750,342 discloses a class of synthetic phosphorous- and sulfur-containing compounds which are useful as lubricating oil additives and which are characterized by the general formula:

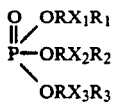

in which R represents a saturated aliphatic $C_2-C_3$ hydrocarbon group, $X_1$, $X_2$ and $X_3$ each represent O or S, and $R_1$, $R_2$ and $R_3$ each represent a $C_1-C_{18}$ alkyl group or a series of saturated aliphatic hydrocarbon groups interlinked by O or S atoms.

U.S. Pat. No. 2,874,192 describes the preparation of mercaptals of long chain hydrocarbon aldehydes and their use as synthetic lubricating oils or anti-oxidants. Compounds of the general formula

(RS)$_2$CHR' are produced wherein R is a hydrocarbon radical derived from the mercaptan and R' is a hydrocarbon radical derived from the aldehyde. R and R' are both independently long chain ($C_8$ to $C_{30}$) hydrocarbons.

U.S. Pat. No. 2,960,523 discloses phosphoric ester derivatives of hydroxylakyl vinyl sulfides having the general formula:

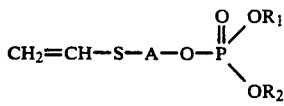

where A is a $C_2-C_6$ alkylene group, and $R_1$ and $R_2$ each are $C_1-C_4$ alkyl groups. The disclosed ester derivatives can be copolymerizable with various acrylic esters to provide copolymers which have utility as flame-proofing agents for textiles and paper products.

U.S. Pat. No. 3,135,804 relates to polyetherthioethers which are prepared by heating alkoxylation products of aliphatic monovalent alcohols with dihydroxyalkyl sulfides at a temperature between 100°-200° C. in the presence of relatively small quantities of acid or acid-forming compounds (generally 0.01-5 wt. %, preferably 0.1-1.5 wt. %) such as p-toluene sulfonic acid, orthophosphoric acid, pyrophosphoric acid, metaphosphoric acid, phenylphosphoric acid, diphenylphosphoric acid, ammonium phosphate, sodium phosphate, triethyl phosphate, methyl toluene sulfonate, dimethyl sulfate and maleic anhydride. The polyether-thioethers are suitable for use as lubricants, hydraulic fluids, metal working fluids, heat transfer agents, insulating oils, textile assistants and as solvents or additives to high molecular weight compounds.

U.S. Pat. No. 3,335,189 discloses the preparation of polyether-thioethers of the general formula:

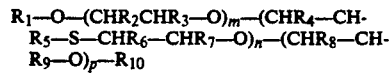

$R_1-O-(CHR_2CHR_3-O)_m-(CHR_4-CH-R_5-S-CHR_6-CHR_7-O)_n-(CHR_8-CH-R_9-O)_p-R_{10}$ wherein $R_1$ and $R_{10}$ are linear or branched alkyl radicals of 1 to 22 carbons and $R_2$ through $R_9$ represent hydrogen and/or the same or different linear or branched alkyl radicals with 1 to 12 carbon atoms. While m, n and p are whole numbers from 1 to 10. The process disclosed in this patent is carried out at elevated temperatures on the order of 100°-220° C., preferably between 140° and 200° C., in the presence of from about 0.01 to 5 wt. %, preferably 0.1 to 1.5 wt. %, of compounds of trivalent phosphorous, such as phosphorous acid or its salts and esters of phosphorous acid or their salts, or phosphonous acid or its salts, esters, amides or the like. The sole example in this patent discusses the lubricating characteristics of the polyether-thioethers.

U.S. Pat. No. 3,446,738 discloses an ester base lubricating composition comprising an aromatic amine and an organic thiophosphite or thiophosphonate having the formula:

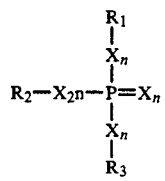

wherein X is O or S, at least one X being S; n is 0 or 1, but at least three n's being 1; and $R_1$, $R_2$ and $R_3$ are alkyl or aromatic groups. The organic thiophosphite or thiophosphonate functions as an anti-oxidant.

U.S. Pat. No. 3,426,075 relates to mixed polyphenyl ethers-thioethers useful as synthetic lubricants. These compounds are prepared by reacting sodium or potassium salts of thiophenols with halogen containing diphenyl ethers to produce compounds of the structure:

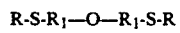

R-S-R$_1$—O—R$_1$-S-R wherein R and $R_1$ are phenyl or substituted phenyl i.e. containing phenoxy or thiophenyl substituents. R and $R_1$ are limited to phenyl.

U.S. Pat. No. 3,450,771 describes the process for producing organic sulfides from the reaction of mercaptans with alcohols. The process consists of reacting mercaptans of the formula R-SH with alcohols of the formula R'—OH at a temperature of 100° to 300° C. in the presence of an alkali metal hydroxide to produce organic sulfides of the formula R-S-R' wherein R and R' are hydrocarbyl radicals.

U.S. Pat. No. 3,660,497 discloses dodecylethermethyl sulfides of the general formula:

$$C_{12}H_{25}(OCH_2CH_2)_x\text{-}S\text{-}R$$

wherein R is a methyl radical when x=1 or 2, and R is a monovalent acetonyl radical when x=0.

U.S. Pat. No. 4,031,023 relates to the use of hydroxy thioethers as oxidation inhibitors and anti-wear agents for lubricating oils. The hydroxy thioethers are of the formula:

$$(HS)_q\text{-}R\left[\text{-}S\text{-}\underset{(R')_2}{\underset{|}{C_x}}\text{-}(OC\underset{(R')_2}{\underset{|}{y}})_z\text{-}OH\right]_m$$

wherein R is a hydrocarbon group of from $C_1$ to $C_{30}$; R' is independently selected from hydrogen or $C_1$ to $C_{20}$ hydrocarbyl; x and y are independently 2 to 5; z is from zero to 5; q is from zero to 4 and m is from 1 to 5 with the proviso that m+q is from 1 to 6.

The materials are prepared by reacting mercaptans with alkylene oxides or by reacting alpha-olefins with hydroxy containing mercaptans.

U.S. Pat. No. 4,081,387 discloses lubricating compositions comprising a major proportion of lubricating oil and a minor proportion of at least one phosphorous- and sulfur-containing additive of the formula:

$$Y^a\text{-}S\text{-}Y^b$$

wherein $Y^a$ is $$R_1\text{-}\underset{R_2}{\underset{|}{\overset{\overset{X}{\|}}{P}}}\text{-}X\text{-}\underset{R_3}{\underset{|}{CH}}\text{-}Z$$

and wherein Z is a saturated or unsaturated hydrocarbyl group; each $R_1$ and $R_2$, independently, is a hydrocarbyl, hydrocarbyloxy or hydrocarbylmercapto group having from 1 to 10 carbon atoms; $R_3$ is hydrogen or a $C_1$-$C_{30}$ hydrocarbyl group; X is S or O; and $Y^b$ is -$R_4$H or -$R_4$-S-$R_5$, wherein $R_4$ is a $C_1$-$C_{30}$ divalent hydrocarbyl group and $R_5$ is H or $Y^a$. The disclosed lubricating compositions exhibit increased resistance to oxidative degradation and anti-wear properties.

U.S. Pat. No. 4,217,233 describes the use of epithio compounds as lubricant additives useful as extreme pressure or anti-wear agents. The compounds may be characterized by the formula:

$$R\text{-}X\text{-}CH_2\text{-}\underset{SY}{\underset{|}{CH}}\text{-}\underset{Z}{\underset{|}{CH}}\text{-}Q$$

wherein X is oxygen or sulfur; Y and Z are together a direct bond; Q is hydrogen; and R is branched or unbranched alkyl of from 8 to 22 carbon atoms (claim 1).

U.S. Pat. No. 4,704,217 describes the use of friction modifiers of the formula:

$$R\text{-}(O\text{-}R')_a\text{-}N\underset{\diagdown(OR'')_yH}{\overset{\diagup(OR'')_xH}{}}$$

in gasoline crankcase oils wherein R is a ($C_1$-$C_{20}$) hydrocarbyl radical; R' and R'' are divalent ($C_1$-$C_{10}$) alkylene groups; a is an integer of about 1 to about 10 and x+y is a value of about 1 to about 20.

U.S. Pat. No. 4,511,480 discloses phosphite esters of oxyalkylated thiols as corrosion inhibitors for ferrous metals in deep gas wells. The disclosed esters have the formula:

$$[R_1S(R_2O)_x]_m\text{-}\overset{\overset{O}{\|}}{P}(OH)_n$$

where $R_1$ represents alkyl, cycloalkyl, aryl, aralkyl and heterocyclic; $R_2$ represents alkyl; x is 1–4, m is 1 or 2; n is 1 when m is 2 and n is 2 when m is 1.

U.S. Pat. No. 4,579,672 discloses lubricating compositions comprising a major portion of lubricating oil and a minor proportion of an oil soluble alkoxypolyethyleneoxy acid phosphite ester providing improved water tolerance properties to the oil. The claimed phosphites are of the structure:

$$R_1O(CH_2CH_2O)_x\underset{R_2}{\underset{|}{P}}OH$$

wherein, $R_1$ is alkyl or alkenyl; $R_2$ is OH, alkoxy or oxyalkenyl or $R_1O(CH_2CH_2O)_x$ in which the total number of carbon atoms is 8 to 36 and x is in the range 2 to 4.

U.S. Pat. No. 4,776,969 relates to cyclic phosphates, such as 1,3-dioxa-2-phospha-6-thiocyclooctane-2-(dodecylthiodiethyleneoxy)-2-oxide, and their use as an anti-wear, anti-oxidant, and/or friction modifying agent for oleaginous compositions such as fuels and lubricating oils, particularly automatic transmission fluids. The cyclic phosphates can be represented by the formula:

$$R\text{-}(S)_n\text{-}(R_1\text{-}O)_{n'}\text{-}\overset{\overset{O}{\|}}{P}\underset{\diagdown X'\text{-}R_3\diagup}{\overset{\diagup X\text{-}R_2\diagdown}{}}(Y)_{n''}$$

where R can represent alkyl, alkenyl, cycloalkyl, aralkyl, alkaryl; n is a number which can vary from 1 to about 3; $R_1$ is alkylene, n' is a number which can vary from about 1 to about 12; X and X' which may be the same or different can independently represent —O—, —NH— or —S—; $R_2$ and $R_3$ which may be the same or different can independently represent substituted or unsubstituted alkylene; n'' can represent the number 0 or 1; and Y can represent —O—, —NH—, —S—, —S—S— or $CH_2$ when n'' is 1; said $R_2$ and $R_3$ being joined together and constituting part of a cyclic hetero ring structure when n'' is 0. The cyclic phosphates may be prepared by reacting an organo phosphorous oxy dichloride and a cyclizing agent such as thiobisethanol. The non-cyclic portion of the cyclic phosphates typically is derived from a hydrocarbyl thioether alcohol which, in turn, can be prepared by reacting a mercaptan and appropriate alkylene oxide or by reacting a terminal olefin with a compound of the formula HS-($R_1$—O)$_{n'}$H.

The article "The Condensation of 2-Hydroxyethyl Sulfides with Alcohols and Phenols" by F. Richter, F. B. Augustine, E. Kroft and E. E. Reid, published in Journal of Polymer Science, Vol. XLI, pp 4076–4079, discusses the preparation of ethers by the condensation of alcohols and phenols with 2-hydroxyethyl sulfides using p-toluenesulfonic acids as catalysts.

The article "Thioglycol Polymers I Hydrochloric Acid-Catalyzed Auto Condensation of Thiodiglycol", by Woodward, Journal of Polymer Science, Vol. XLI, pp 219–223 (1959), describes the homopolymerization of thiobisethanol with acid or dehydrating catalyst.

The article "Thioglycol Polymers II Copolymerization of Thiodiglycol and Similar Thioglycols with Aliphatic Hydroxy Compounds", by Andrews et al, Journal of Polymer Science, Vol. XLI, pp 231–239 (1959), describes the acid catalyzed polymerization of thiobisethanol with an alkyl hydroxy or polyhydroxy compound.

U.S. Pat. No. 2,290,880 discloses ethers of alcohol amines which may be used as interface modifying agents in a wide variety of arts. The compounds are said to be useful in lubricating oils and the like, thus enabling the production of effective boring oils, cutting oils, drilling oils, wire drawing oils, extreme pressure lubricants and the like.

U.S. Pat. No. 3,034,907 discloses agents which are effective for hindering or retarding rust formation on iron surfaces and ice formation in the intake system of internal combustion engines. The agents which are disclosed are characterized by a content of (a) a hydrophobic organic carrier, (b) a carboxylic acid amide monocarboxylic acid, and (c) an at least equivalent amount of a hydroxyalkylated nitrogen base which contains at least one lipophilic radical. The hydroxyalkylated nitrogen base corresponds to the general formula:

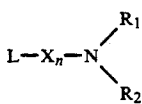

wherein L represents a lipophilic radical; X can represent lower —O-alkylene, —S-alkylene, —O-hydroxyalkylene or —S-hydroxyalkylene, wherein n represents the integer 0 or 1; $R_1$ represents hydrogen, a lower alkyl or lower hydroxyalkyl or lower aminoalkyl radical; and $R_2$ is the same as $(L-X_n)$ and $R_1$. In one embodiment, L represents an aliphatic $C_{12}$–$C_{18}$ hydrocarbon radical, n is 0, and at least one of $R_1$ and $R_2$ is a low molecular weight hydroxyalkyl or hydroxyalkylaminoethyl radical.

U.S. Pat. No. 3,235,501 discloses foam-inhibited oil compositions which comprise a oleaginous material, a detergent additive, a silicone anti-foamant, and a small amount of a polyalkyl oxylated aliphatic amine which conforms to one of the following formulas (a) or (b) depending on whether the amine from which they are prepared is a mono- or diamine:

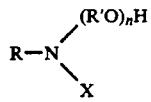

where R is an aliphatic radical of from about 4 to about 24 carbon atoms, R'O is an alkylene oxide radical selected from the group consisting of the ethylene oxide and propylene oxide radicals, n is an integer from 1 to about 25, and X is selected from hydrogen, R and -(R'O)$_n$H radicals, and

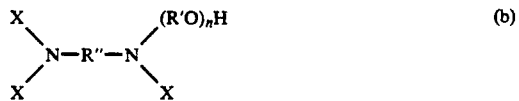

where R" is an aliphatic radical having from 2 to about 6 carbon atoms, R'O, n and X are the same as in formula (a), but at least one X is an R radical.

U.S. Pat. No. 3,705,139 discloses alkyl sulfide compounds of the formula:

where $R_1$ represents a hydrocarbyl radical having 6 to 22 carbon atoms, $R_2$ and $R_3$ each represents a hydrocarbyl radical having 1 to 4 carbon atoms, A can represent nitrogen, n represents an integer in the range of 0–100, and Z can represent hydrogen. The alkyl sulfide compounds are disclosed as being anti-static agents.

U.S. Pat. No. 3,933,659 discloses lubricating oil composition which comprise a major amount of an oil of lubricating viscosity, and an effective amount of each of the following: (1) an alkenyl succinimide, (2) a Group II metal salt of a dihydrocarbyl dithiophosphoric acid, (3) a compound selected from the group consisting of (a) fatty acid esters of dihydric and other polyhydric alcohols, and oil soluble oxyalkylated derivatives thereof, (b) fatty acid amides of low molecular weight amino acids, (c) N-fatty alkyl-N,N diethanol amines, (d) N-fatty alkyl-N,N-di(ethoxyethanol) amines, (e) N-fatty alkyl-N,N-di-poly(ethoxy) ethanol amines, and (f) mixtures thereof, and (4) a basic sulfurized alkaline earth metal alkyl phenate. Such lubricating compositions are useful as functional fluids in systems requiring fluid coupling, hydraulic fluid and/or lubrication of relatively moving parts, particularly as automatic transmission fluids.

U.S. Pat. No. 4,201,684 relates to lubricating oil compositions adapted for use as a crankcase lubricant in internal combustion engines containing a friction reducing amount of a sulfurized fatty acid amide, ester or ester-amide of an oxyalkylated amine.

U.S. Pat. No. 4,231,883 relates to the use of an alkoxylated hydrocarbyl amine in a lubricating oil or fuel to reduce the friction of an internal combustion engine in which the lubricating oil or fuel is used. An example of the alkoxylated hydrocarbyl amine compounds that are disclosed in this patent is N,N-bis(2-hydroxyethyl) oleylamine.

U.S. Pat. No. 4,129,508 relates to lubricant and fuel compositions characterized by improved demulsifying properties. The patent discloses an automatic transmission fluid which includes a number of additives including a dialkyl phosphite, the reaction product of a polyisobutenyl-substituted succinic anhydride, commercial tetraethylene pentamine, and boric acid prepared as set forth in U.S. Pat. No. 3,254,025, and a conventional friction modifier based on polyoxyethylene tallow amine (Ethomeen T/12), the reaction product of polyisobutenyl succinic anhydride and an ethylene polyamine, and Ethomeen C/15. The Ethomeen compounds are available commercially from the Armak Chemical Division of Akzo Chemie.

U.S. Pat. No. 4,170,560 discloses additive compositions for use in crankcase lubricating oils comprising a mixture of an oil soluble anti-oxidant and an oil soluble hydroxyl amine which includes both Ethomeens and Ethoduomeens, which are trade names for compounds available commercially from the Armak Chemical Division of Akzo Chemie.

U.S. Pat. No. 4,382,006 discloses a lubricating composition containing a friction reducing portion of a borated adduct of compounds which include Ethomeens.

U.S. Pat. No. 3,509,052 relates to lubricating compositions containing a lubricating oil, a dispersant which is a derivative of a substituted succinic acid, and a demulsifier. The demulsifier may comprise, for example, an Ethomeen, but the preferred demulsifiers are polyoxyalkylene polyols and derivatives thereof.

U.S. Pat. No. 3,254,025 relates to boron containing acylated amines and lubricating compositions containing them, the amines are produced by reacting a polymer substituted succinic anhydride containing at least about 50 aliphatic carbon atoms with an amine and then reacting this acylated amine product with boron.

U.S. Pat. No. 3,502,677 relates to substituted polyamines which are useful as additives in lubricating compositions, fuels, hydrocarbon oils and power-transmitting fluids. The substituted polyamines are prepared by reacting an alkylene polyamine with a substantially hydrocarbon-substituted succinic acid-producing compound and a phosphorous acid-producing compound.

U.S. Pat. No. 4,615,818 describes oil-soluble sulfurized organic compounds represented by the formula:

$$RS_xR_1$$

wherein R and $R_1$ are organic groups. Examples of these organic groups include hydrocarbon groups or substituted hydrocarbon groups containing alkyl, aryl, aralkyl, alkaryl, alkanoate, thiazole, imidazole, phosphorothionate, betaketoalkyl groups, etc. The substantially hydrocarbon groups may contain other substituents such as halogen, amino, hydroxyl, mercapto, alkoxy, aryloxy, thio, nitro, sulfonic acid, carboxylic acid, carboxylic acid ester, etc.

U.S. Pat. No. 4,664,826 relates to metal salt esters of hydrocarbyl substituted succinic acid or anhydride, such as octadecenyl succinic anhydride, and alkanols, such as thiobisethanol, which are capable of exhibiting friction modification, oxidation inhibition, and corrosion inhibition properties in power transmitting fluids such as automatic transmission fluids.

U.S. Pat. No. 4,681,694 discloses a crankcase lubricating oil composition comprising (a) a major portion of a lubricating oil which contains at least one over based calcium alkylphenolate or sulfurized calcium alkylphenolate, a zinc dithiophosphate, and dinonyldiphenylamine, and (b) a rust-inhibiting amount of a dialkoxylated alkylpolyoxyalkyl tertiary amine of the formula:

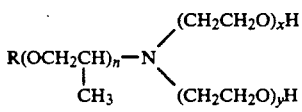

where R is $C_1$-$C_{30}$ alkyl, n is an integer of about 1 to 6, and x+y is about 2 to 30 where neither x nor y is zero.

U.S. Pat. No. 4,702,850 relates to mineral based power transmitting fluids such as automatic transmission fluid which contain an ester of thiobisalkanol and a $C_{12}$-$C_{50}$ hydrocarbon succinic acid or anhydride. The ester functions as a multifunctional additive providing friction modification, corrosion inhibition, anti-wear, oxidation inhibition and extreme pressure properties to the fluids. U.S. Pat. No. 4,664,826 discloses metal salt derivatives of such ester additives.

U.S. Pat. No. 4,764,299 deals with compositions containing sulfur and oxygen which are useful in lubricants and automatic transmission fluids. The compositions are prepared by reacting at least two equivalents of a mercaptan containing at least five carbon atoms and at least two equivalents of a beta-dialkanol. The sulfur and oxygen containing compositions may be illustrated by the formula:

$$RS(AS_xAO)_yAS_xASR_1$$

wherein x is 1 or greater; y is zero or greater; R and $R_1$ are hydrocarbyl groups; A is an alkylene group; and at least one of R and $R_1$ contains at least five carbon atoms.

In an article "Nucleophilic Substitution of Hydroxyl Groups in 2-Alkyl (Aryl)-Thioethanols", published by Fokin et al in the Bull. Acad. Sci. U.S.S.R. Div. Chem. Sci. 1982, Page 1667, there is described the homocondensation of 2-alkylthioethanols. It is also disclosed in the Fokin article that the 2-alkylthioethanol may be reacted with an alcohol under catalysis by strong mineral acids, to give a product containing both sulfur and ether linkages. The mineral acid catalysts disclosed in the Fokin article include HCl, $H_3PO_4$, $H_2SO_4$, 4-$CH_3C_6H_4SO_3H$, $HBF_2$, $HClO_4$ and $HOSO_2F$. Aromatic sulfur-containing compounds containing beta-hydroxy groups and their reaction properties are also discussed in the Fokin article. The Fokin paper does not discuss any particular utility or special advantage for the compositions described therein.

PCT application WO 88/03554 relates to phosphorous- and/or nitrogen-containing derivative compositions which are useful in fuels, and in lubricating and functional fluid compositions. The derivative compositions comprise a phosphorous- and/or nitrogen-containing derivative composition of sulfur-containing compounds prepared by reacting at least one sulfur composition with either a di- or trihydrocarbyl phosphite, an amine compound containing at least one NH or $NH_2$ group, or a combination of such phosphite and amine. The sulfur compositions which may be reacted with the phosphite, amine or a combination of phosphite and amine may be characterized by the formula

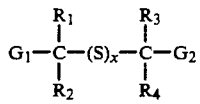

wherein $R_1$, $R_2$, $R_3$ and $R_4$ are each independently H or hydrocarbyl groups; $R_1$ and/or $R_3$ may be $G_1$ or $G_2$; $R_1$ and $R_2$ and/or $R_3$ and $R_4$ together may be alkylene groups containing about four to about seven carbon atoms; $G_1$ and $G_2$ are each independently C(X)R, COOR, C≡N, $R_5$-C=$NR_6$, or $NO_2$, and $G_1$ may be $CH_2OH$; X is S or O; and each of R, $R_5$ and $R_6$, independently, is H or a hydrocarbyl group. The compositions of this patent also may include at least on carboxylic dispersant composition.

SUMMARY OF THE INVENTION

Figure 1:
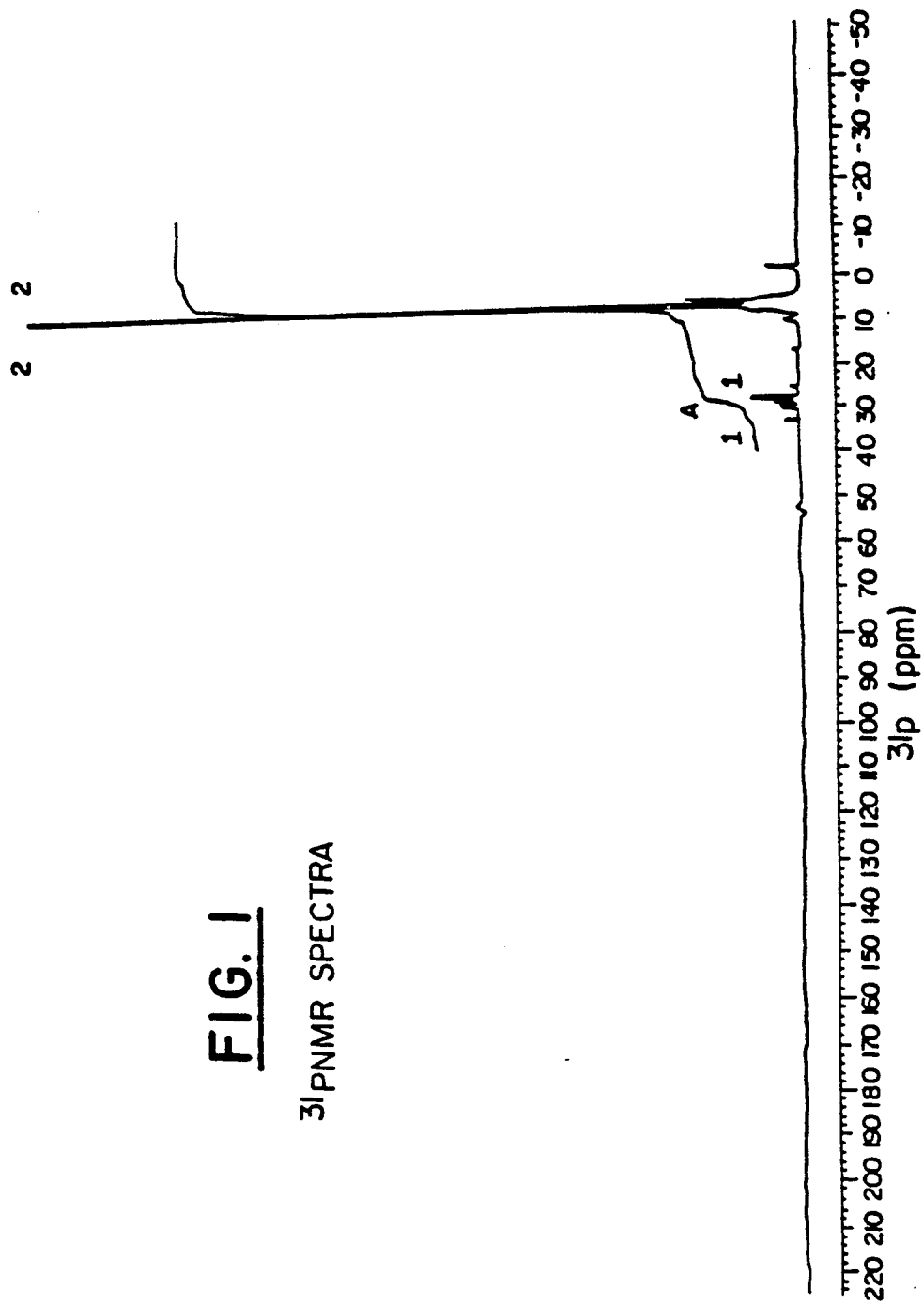
FIG. 1 is a $^{31}P$ NMR spectra for a single phase phosphorous-and sulfur-containing reaction product mixture formed by reacting equal molar ratios of tributyl phosphite, hydroxyethyl-n-dodecyl sulfide and thiobisethanol.

The present invention is based in part on the discovery that the phosphorous- and sulfur-containing product mixture formed by the reaction, preferably simultaneous reaction, of a beta-hydroxy thioether reactant, an organic phosphite ester reactant and, optionally, a nucleophilic reactant selected for its ability to react with an episulfonium cation of the formula

to form mixtures of non-phosphorous-containing thioether-containing species and organo phosphorous-containing species which are very effective in enhancing the anti-wear and anti-oxidation characteristics of oleaginous compositions such as fuels and lubricating oils to which they are added. An added feature of this invention is that the sulfur- and phosphorous-containing product mixtures do not reduce the effectiveness of certain associated friction modifiers when they are used in combination therewith in oleaginous compositions such as ATF's.

The product mixture may be prepared under conditions which favor the formation of a stable single phase mixture which is compatible with oleaginous compositions. The product mixture may also be prepared under conditions which favor the formation of a mixture which separates on standing into a top phase, which is rich in thioether-containing species, and a bottom phase, which is rich in phosphorous-containing species, although both phases contain mixtures of species found in each phase. In such cases, both the top phase mixture and the bottom phase mixture are stable, compatible with oleaginous compositions, and do not adversely affect friction stability of automatic transmission fluids. In short, each of the single phase phosphorous- and sulfur-containing product mixtures, the thioether enriched top phase mixture, and the organo phosphorous enriched bottom phase mixture of this invention, independently, is considered to be a desirable additive for use in oleaginous compositions, particularly in power transmission fluids.

In one aspect of the present invention, a mixed reaction product is prepared by simultaneously reacting (1) beta-hydroxy thioether reactant, (2) a phosphorous-containing reactant, and (3) optionally, a nucleophilic reactant. The beta-hydroxy thioether reactant (BHTE) is characterized by the formula I:

$$R(SCH_2CH_2OH)_x \qquad I$$

wherein R represents an unsubstituted or substituted hydrocarbyl group or a substituted hydrocarbyl, and x is a number from 1 to about 3.

The phosphorous-containing reactant may comprise an organic phosphite esters.

The optional nucleophilic reactant in this aspect of the invention would be a reactant that could react with the episulfonium cation

to form at least non-phosphorous thioether-containing species. Preferably the nucleophilic reactant would be free from any mercapto groups.

In yet another aspect of the invention, the reaction is conducted so as to induce phase separation of the mixed reaction product. The mixed reaction product is separated into a top phase mixture and a bottom phase mixture. The top phase mixture is enriched in non-phosphorous thioether-containing species and contains relatively minor amounts of phosphorous-containing species, whereas the bottom phase mixture is enriched in phosphorous-containing species. The majority of the phosphorous-containing product species are found in the bottom phase mixture. The phase separation preferably is accomplished by completely or partially distilling the alcohol by-product derived from phosphite reactant and allowing the resulting distalland to stand exposed to air at room temperature or elevated temperature (up to about 40°–50° C.) for a period of from about 1 to about 10 days.

In still another aspect of the invention, the above single phase mixture, top phase mixture and/or bottom phase mixture, independently or in admixture, is employed as an anti-wear and anti-oxidation additive in an oleaginous composition. The reaction product mixtures, when used in combination with an ashless dispersant and a friction modifier, and preferably also with a seal swellant and supplemental anti-oxidant, are particularly suited to meeting the stringent ATF requirements from the standpoint of the proper balance of anti-wear, static and dynamic friction coefficients, friction stability, dispersancy, sludge inhibition and anti-oxidation properties.

In a still further embodiment of the present invention, there is provided a lubricating oil composition concentrate adaptable for use as an automatic transmission fluid comprising the above-described single phase, top phase or bottom phase mixtures of mixed reaction products, preferably in combination with at least a dispersant and a friction modifier.

In another embodiment of the present invention, there is provided a lubricating oil composition concentrate adaptable for use as a power transmitting fluid which comprises a lubricating oil having dissolved or dispersed therein the above-described single phase mixture, top phase mixture and/or bottom phase mixture of reaction products, together with an ashless dispersant, and a hydroxyl amine friction modifier such as depicted in formulas XI and XII hereinafter.

In another embodiment of the present invention there is provided a process for improving the anti-wear and anti-oxidation properties of a lubricating oil composition which is adapted for use as a power transmitting fluid which comprises adding to said lubricating oil composition the phosphorous- and sulfur-containing mixtures of reaction products disclosed herein, in addition to an ashless dispersant and a friction modifier.

In still another embodiment of the present invention there is provided a process for preparing a multifunctional lubricating oil additive by reacting together, preferably simultaneously, (1) a beta-hydroxy thioether reactant, (2) an organic phosphite ester, and, optionally, (3) a nucleophilic reactant.

In another aspect of the invention, there is provided a hydrocarbon soluble or dispersible sulfur-containing composition containing a plurality of thioether-containing species, wherein at least one of the species is characterized by the formula XIII described hereinafter.

DESCRIPTION OF PREFERRED EMBODIMENTS

In one preferred embodiment, the phosphorous- and sulfur-containing anti-wear additives of the present invention comprise a mixture of compounds which are formed by reacting in admixture, preferably in simultaneous admixture, the following components, namely: (1) beta-hydroxy thioether reactant, (2) organic phosphite reactant, and, optionally, (3) nucleophilic reactant.

The beta-hydroxy thioether reactant is characterized by the formula I:

$$R(SCH_2CH_2OH)_x \qquad \text{I}$$

wherein R represents an unsubstituted hydrocarbyl or a substituted hydrocarbyl group, and x is a number from 1 to about 3, preferably 1 to 2.

As used in this specification and claims, the term "substituted hydrocarbyl group" is meant to include hydrocarbyl groups which contain at least one pendant or internal hetero-atom containing species selected from the group consisting of hydroxy, oxy, thio, oxyalkylene and oxyalkylenethio groups. Thus, the term "substituted hydrocarbyl group" is intended to exclude from within its scope $-C(X)R_{2'}$, $-COOR_{2'}$, $-C\equiv N$, $-R_{3'}C=NR_{4'}$, $-CON(R_{2'})_2$ or $-NO_2$ groups, wherein X is O or S, and wherein $R_2$, $R_3$ and $R_4$, independently, represent H or a hydrocarbyl group.

Typically, R will be a $C_1-C_{30}$ (e.g. $C_1-C_5$), preferably $C_8$ to about $C_{18}$, saturated or unsaturated, straight or branched chain (preferably straight chain) aliphatic hydrocarbyl radical; an aromatic radical, preferably a $C_6-C_{14}$ aromatic radical or a mixed alkaryl or aralkyl radical having from 1 to about 30 typically 1 to about 22, and preferably 1 to about 10 carbon atoms in the alkyl portion thereof; the radical;

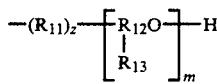

an $-R_1OH$ radical or an $-SR_1OH$ radical. In the above radicals, $R_1$ and $R_{11}$, independently are described as in connection with R as aliphatic, aromatic, and mixed aliphatic/aromatic; z is 0 or 1; m is a number of from about 1 to about 6, preferably 1 to 3; $R_{12}$ is $C_2-C_3$ (e.g. $C_2$ alkanetriyl, and $R_{13}$ is H or $C_1-C_{18}$, preferably $C_1-C_5$ aliphatic, preferably saturated aliphatic hydrocarbyl.

It will be appreciated, of course, that the groups identified in formula I as $-(SCH_2CH_2OH)_x$ are not a block of repeating units. Rather, each $-(SCH_2CH_2OH)_x$ group is a single group bonded appropriately to the hydrocarbyl backbone of the R group in the thioether reactant.

In one preferred aspect, the beta-hydroxy thioether reactant comprises a mixture of compounds of formula I wherein at least one compound has only one $-SCH_2CH_2OH$ group (i.e. x=1) and at least one compound has two $-SCH_2CH_2OH$ groups (i.e. x=2).

Representative examples of suitable R, $R_1$, and $R_{11}$ groups included methyl, ethyl, n-propyl, i-propyl, n-butyl, i-butyl, t-butyl, n-butenyl, hexyl, 2-ethyl hexyl, n-octyl, decyl, dodecyl, dodecenyl, octadecyl octadecenyl, oleyl, stearyl, i-stearyl, hydroxystearyl, benzyl, phenyl, p-methylphenyl, p-propylphenyl, o-butylphenyl, p-butylphenyl, p-dodecylphenyl, p-dodecenylphenyl p-octadecylphenyl, p-octadecenylphenyl, naphthyl, ethoxyethyl, ethoxythioethyl, or the like.

The more preferred R groups include octyl, decyl, dodecyl and octadecyl.

The more preferred $R_1$ or $R_{11}$ groups include methyl, ethyl n-propyl, i-propyl, n-butyl, i-butyl, and n-pentyl.

In more preferred embodiments the value of x in formula I is from 1 to 2, and most preferably is one.

Methods for preparing the beta-hydroxy thioether reactant are known in the art and are discussed, for example, in Reed, Organic Chemistry of Bivalent Sulfur, Vol. II (1960), published by Chemical Publishing Co., Inc., and in U.S. Pat. No. 4,031,023, the disclosures of which are incorporated herein by reference. The beta-hydroxy thioether reactant may be prepared, for example, by heating together at a temperature of from about 140° to about 160° C. an alkyl mercaptan and an epoxide compound in the presence of a basic catalyst, e.g. NaOH. Alternatively, the beta-hydroxy thioether reactant can be prepared by heating together in the presence of a free radical generator, such as benzoyl peroxide, an alkyl mercaptan such as 2-mercaptoethanol and an alpha-olefin such as 1-decene.

The phosphorous-containing reactant may comprise an organic phosphite ester characterized by at least one of the following formulas II or III:

$$P(OR_5)_3 \qquad \text{II}$$

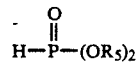

wherein $R_5$, independently, represents the same or different $C_1-C_{30}$ (typically $C_1-C_5$) saturated or unsaturated, straight or branched chain aliphatic hydrocarbyl radical or the radical

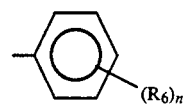

wherein $R_6$, independently, represents the same or different $C_1-C_{24}$ (typically $C_1-C_4$) hydrocarbyl radical or H; wherein n is an integer from 1 to 3; and wherein $R_5$ and $R_6$ may be inertly substituted.

Representative examples of suitable $R_5$ groups include methyl, ethyl, n-propyl, i-propyl, n-butyl, i-butyl, t-butyl, n-propenyl, n-butenyl, n-hexyl, nonylphenyl, n-dodecyl, n-dodecenyl, hexadecyl, octadecenyl, stearyl, i-stearyl, hydroxystearyl, phenyl, p-methyl phenyl, 3,5-dimethylphenyl, p-propylphenyl, o-butylphenyl, 2,3,5-butylphenyl, dodecylphenyl, stearylphenyl, p-octadecylphenyl and p-octadecenylphenyl and the like.

The more preferred $R_5$ groups included methyl, ethyl, n-propyl, n-butyl and phenyl. Although not required, it is preferred that the $R_5$ groups are the same for any given organic phosphite ester. The most preferred phosphite esters are trihydrocarbyl phosphites, such as trimethyl phosphite, triethyl phosphite, tributyl phosphite, and the like, and dihydrocarbyl hydrogen phosphites, such as dimethyl hydrogen phosphite, dibutyl hydrogen phosphite, and the like. The organic phosphites can be obtained by the direct esterification of phosphorous acid or reaction of a phosphorous trihalide with an alcohol or a mixture of alcohols. The methods for preparing the organic phosphite ester reactant are known in the art and are discussed, for example, in U.S. Pat. No. 3,513,093, the disclosure of which is incorporated herein by reference.

The nucleophilic reactant by definition, does not include an $-SCH_2CH_2OH$ group and hence is not believed to be capable of forming an episulfonium cation as described herein. However, it may be employed in minor amounts in the reaction mixture because it is believed to be capable of reacting with an episulfonium cation, i.e.

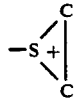

to form a non-phosphorous thioether-containing species and is defined herein to be free from mercapto groups or any other groups which would otherwise interfere with the desired reaction. The nucleophilic reactant is an optional component of the reaction mixture, and it may be added as a separate component or it may be formed in situ during the overall reaction scheme.

In one preferred aspect, the nucleophilic reactant may be characterized by the formulas IV, IV' or IV":

$R_7(LH)_{n'}$      IV

      IV'

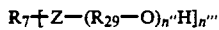      IV"

wherein $R_7$ represents an inertly substituted or unsubstituted aliphatic hydrocarbyl group, typically a $C_1$-$C_{30}$, preferably $C_6$-$C_{22}$, saturated or unsaturated (preferably saturated), straight or branched chain (preferably straight chain) aliphatic hydrocarbon radical; L represents at least one member selected form the group consisting of oxy (preferably oxy), alkylene, polyoxyalkylene, and poly(oxyalkylene)thio (i.e., wherein sulfur is bonded directly to the $R_7$ and the structure is terminated with a hydroxyl group); n' is number which can vary from 1 to 3, typically 1 to 2, and preferably 1, and represents the number of -LH groups attached to $R_7$; n" is a number which can vary from 2 to 4; n'" is a number which can vary from 1 to 3, typically 1 to 2, preferably 1, and represents the number of $[Z-(R_{29}O)_{n''}H]$ groups attached to $R_7$; $R_{29}$, independently, is an alkylene radical, typically a $C_1$-$C_5$ alkylene radical, and preferably a $C_2$-$C_4$ alkylene radical; Z is selected from —S—, —S—S— (preferably —S— or —S—S—), —O—, >$NR_{10}$ wherein $R_{10}$ is H, alkyl, typically $C_1$-$C_{22}$, preferably $C_1$-$C_{18}$ alkyl or monohydroxy alkyl, typically $C_1$-$C_{18}$, preferably $C_1$-$C_{12}$, and (b) and (d), independently, are from 1 to 3, with the proviso that the identity of $R_{29}$, b, d, n" and n'" is selected such that the compound represented by formulas IV' and IV" do not contain the $-SCH_2CH_2OH$ group.

In another aspect, the nucleophilic reactant can be characterized by the formula V:

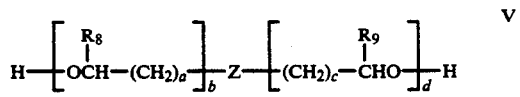      V wherein $R_8$ and $R_9$, each independently, represent H or an alkyl group, typically $C_1$-$C_{12}$ (e.g. $C_1$-$C_5$) alkyl; Z is the same as described above in connection with formulas IV' and IV"; and a, b, c, and d, each, independently, represents the same or different number of from about 1 to about 3 with the proviso that a+b and c+d, are each at least 3. Preferably $R_8$ and $R_9$ are the same, the numbers represented by b and d are the same, and the numbers represented by a and c are the same, thus resulting in the nucleophilic reactant being a bisalkanol.

When L is oxy, i.e., oxygen, formula IV can represent alkanols having from 1 to 3 hydroxyl groups and derivatives thereof; when L is oxyalkylene or polyoxyalkylene, formula IV can represent alkoxylated alkanols having from 1 to 3 hydroxyl terminated oxyalkylene or polyoxyalkylene side chains; and when L is poly(oxyalkylene)thio, formula IV can represent a hydroxyl terminated polyether-thioether.

The preferred nucleophilic reactants of formula IV are alkanols, most preferably monohydroxy alkanols having from about 6 to about 22 carbons atoms. Representative examples of nucleophilic reactants in accordance with formula IV include n-hexanol, n-octanol, oleyl alcohol, 1,2-dihydroxydodecane, trimethylol propane, 1-hydroxy-3-oxy-decane, 1-hydroxy-3,6-dioxydodecane, 1-hydroxy-3-oxy-6-thiadodecane, 1-hydroxy-3-oxy-6,7-dithiaundecane and mixtures thereof.

When Z is —O—, formulas IV' and V can represent ethylene glycol and derivatives thereof; when Z is >$NR_{10}$, and $R_{10}$ is alkyl or hydrogen, formulas IV' and V can represent a diethanolamine and derivatives thereof; when $R_{10}$ is a monohydroxy-substituted alkyl, such as $-(CH_2)2OH$, formulas IV' and V can represent triethanolamine and derivatives thereof.

If b or d are greater than 1, then formulas IV' and V are meant to express alkoxylated derivatives of heterodialkanols, such as ethoxylated derivatives.

The preferred nucleophilic reactants are thiodialkanols, wherein in formulas IV' and V, Z is —S— or —S—S—, and $R_8$ and $R_9$ are, independently, hydrogen, ethyl or methyl.

In the more preferred nucleophilic reactants of formulas IV' and V, a, b, c and d are each 1 or 2, $R_8$ is hydrogen or methyl, $R_9$ is hydrogen, methyl or ethyl, and Z is sulfur, with the proviso that a, b, c and d are selected such that the reactants do not contain any $-SCH_2CH_2OH$ groups.

Representative nucleophilic reactants which are thiodialkanols include 3,3'-thiodipropanol; thio-bis ethoxyethanol; thiobisisopropoxyisopropanol; and mixtures thereof.

When Z is sulfur, the nucleophilic reactants may be prepared, for example, in accordance with the following equation:

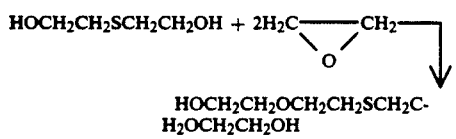

Eq. 1

When Z is —O—, formula IV''' can represent an alkoxylated alkanol having from 1 to 3 repeating alkoxy groups with terminal hydroxyl groups; when Z is —S—, formula IV''' can represent hydroxyl terminated alkylether-thioether compounds; and when Z is $>NR_{10}$, formula IV''' can represent an alkoxylated, e.g., ethoxylated, alkanolamine and derivatives thereof.

In the more preferred nucleophilic reactants of formula IV''', Z is sulfur, n'' is 2, n''' is 1, $R_7$ is normal $C_{12}$ alkyl, and $R_{29}$ is ethyl or propyl.

Representative nucleophilic reactants of formula IV''' include 1-hydroxy-3-oxy-6-thianonadecane, 1-hydroxy-3,6-dioxy-nonadecane, 1-hydroxy-3-oxy-6,7-dithiaeicosane, di-(5-hydroxy-ethoxyethyl) octadecylamine and mixtures thereof.

The reaction of the beta-hydroxy thioether and the phosphorous-containing reactant, and the nucleophilic reactant, if such nucleophilic reactant were to be employed, is performed, for example, by mixing the reactants and heating the reaction mixture under distillation conditions (to remove by-product alcohol as it is evolved) at a reaction temperature of typically from about 75° to about 130° C., (e.g. 85° to about 120° C.) preferably from about 90° to about 118° C., (e.g. 95° to 115° C.), and most preferably from about 100° to about 115° C. for a period of time of typically from about 1 to about 24 hours, preferably from about 4 to about 18 hours, and most preferably from about 7 to about 12 hours. The reaction could also be carried out continuously in a suitable vessel.

It will be noted that a portion of the by-product alcohol, as illustrated hereinafter in equation 2, may function as a nucleophilic reactant that is prepared in situ, since the alcohol may react with the episulfonium cation, to yield thioether-containing species. Preferably, however, the by-product alcohol is continuously removed during the course of reaction, e.g., from the overhead using a nitrogen sweep. Typically, the identity of $R_5$ of the phosphite reactant is selected to facilitate alcohol removal.

A convenient way to determine completion of the reaction is to periodically monitor the reaction mixture by removing samples therefrom and subjecting the samples to infrared analysis. As the reaction proceeds, a hydrogen phosphite peak will appear (at 4.1 micron on the IR spectra) and its height will continue to grow over the course of the reaction. At the same time, the height of the hydroxyl peak (at 2.9 microns on the IR spectra) attributable to alcohol by-product and any hydroxyl-containing reactants will diminish. Accordingly, at some point in time during the reaction, the height of the hydrogen phosphite peak will exceed the height of the hydroxyl peak.

The reaction is terminated at any time after this point, and preferably before the point at which the hydroxyl peak disappears altogether. If the reaction is continued beyond the point at which the hydroxyl peak disappears, phase separations can occur.

Under certain conditions, e.g. continuing the reaction beyond its intended end point, removing all of the alcohol by-product and/or conducting the reaction at higher than the prescribed temperatures or prolonged exposure of the product mixture to air, the resulting product mixture tends to separate into two separate phases. The reason for this subsequent phase separation is not entirely understood. However, it is believed that at least in certain circumstances, such as introduction of small amounts of water, some of the species in the product mixture undergo hydrolysis, thereby becoming more dense and more polar and increasing the tendency toward phase separation.

When such phase separation occurs, it has been found that the top phase generally will contain a mixture enriched (relative to the bottom phase) in non-phosphorous- thioether-containing species, and that the bottom phase will contain a mixture enriched (relative to the top phase) in phosphorous-containing species. Typically, the top phase will comprise from about 30 to about 80 weight percent of the reaction mixture, and will contain less than about 20 weight percent, typically less than about 15 weight percent of the phosphorous-containing species, as determined by elemental phosphorous analysis.

The phosphorous-containing species typically found in the bottom phase include phosphorous acid and a mixture of organo phosphorous species. The organo phosphorous species, as discussed more fully hereinbelow, comprise organo phosphite compounds which do not contain any sulfur in their structure, as well as organo phosphite compounds which contain sulfur within their structure. The various phosphorous- and sulfur-containing species found in the top and bottom phase are illustrated below.

The reaction between the beta-thioether reactant and the phosphorous-containing reactant (and optional nucleophilic reactant) may be performed with or without a catalyst, however, it is preferable to perform the reaction in the presence of a basic catalyst such as sodium methoxide to decrease the reaction time. Other suitable basic catalysts which may be employed include, for example, sodium phenate, tertiary amines such as triethylamine or pyridine, and metal carbonates such as potassium carbonate, sodium carbonate or magnesium carbonate.

In a less preferred embodiment, the reactive components can be added and mixed sequentially, provided that the mixing is complete prior to attaining the reaction temperatures specified above.

The reaction may be illustrated generically by the following equation 2:

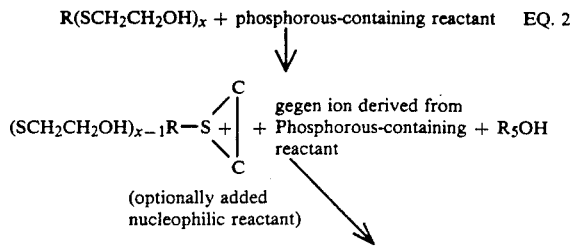

-continued

Product Mixture
(thioether-containing species,
phosphorous-containing species)

With reference to the above equation 2, it is believed that the alcohol, i.e. R₅OH, generated during the reaction can react with the episulfonium cation group,

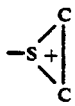

and be incorporated into the thioether-containing species. From an analysis of the thioether-containing and phosphorous-containing species in the product mixture, it appears that other species in the reaction mass react with the episulfonium cation

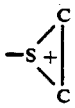

group as well. These other species include, for example, R(SCH₂CH₂OH)ₓ reactant, species derived from the phosphorous-containing reactant, the optionally added nucleophilic reactant and mixtures of these species.

It will be appreciated that during the course of the reactions of this invention, the hydroxyl groups contained in the sulfur-containing reactants (including substituent hydroxyl groups other than those forming part of an -SCH₂CH₂OH group), as well as the hydroxyl groups contained in the nucleophilic reactant, are capable of undergoing reaction with the phosphorous-containing reactant and episulfonium cation. It will be appreciated, further, that both the hereindescribed beta-hydroxy thioether reactant and the optional nucleophilic reactants can have multiple hydroxyl substituents. Thus, the amount of each reactant employed is influenced by the number of reactive functional groups present on each reactant. It has been found the increases in the number of hydroxyl groups on the non-phosphorous containing reactant desirably are accompanied by an increased in the amount of phosphorous-containing reactant.

Accordingly, it is contemplated that typically at least about 10, preferably at least about 15 (e.g. at least about 20) mole percent, of phosphorous containing reactant, based on the total moles of reactants, will be employed. More specifically, such amounts can vary typically from about 10 to about 60, preferably from about 20 to about 50, and most preferably from about 25 to about 40 mole % of phosphorous-containing reactant, based on the total moles of reactants.

Moreover, since the nucleophilic reactant is not believed to be capable of forming the episulfonium cation, it is contemplated that such reactant will comprise typically not greater than about 50, preferably not greater than about 25, and most preferably not greater than about 10 mole %, based on the total number of moles of reactants employed.

In one preferred embodiment, a product mixture of non-phosphorous thioether-containing species and phosphorous-containing species is prepared by reacting in admixture, preferably simultaneous admixture, (a) organic phosphite reactant, and (b) organic sulfur-containing reactant comprising (i) hydrocarbyl thioalkanol component, and (ii) heterodialkanol component, with the proviso that at least one of the hydrocarbyl thioalkanol or heterodialkanol components contains at least one -SCH₂CH₂OH group thereby qualifying the same as a preferred species of beta-hydroxy thioether.

The organo phosphite component (a) is the same as phosphorous-containing reactant of formulas II or III described above.

The hydrocarbyl thioalkanol reactant (b)(ii) is characterized by at least one of the following formulas VI' and VI":

$$R_{11}-S-(R_{12}O)_mH \qquad \text{VI'}$$
$$\phantom{R_{11}-S-}|$$
$$\phantom{R_{11}-S-}R_{13}$$

$$R_{11}-S-R_{14}-OH \qquad \text{VI"}$$

wherein $R_{11}$ represents a saturated or unsaturated, straight or branched chain hydrocarbyl radical having at most two unsaturated linkages, (preferably straight chain alkyl) typically about $C_8$–$C_{30}$, preferably about $C_8$–$C_{20}$, and most preferably about $C_{10}$–$C_{14}$ alkyl; $R_{12}$ represents a $C_2$–$C_3$ alkanetriyl radical, preferably $C_2$ alkanetriyl; $R_{13}$ represents H (most preferred) or a saturated or unsaturated, straight or branched chain hydrocarbyl radical (preferably straight chain alkyl), typically about $C_1$–$C_{18}$, preferably $C_1$–$C_{14}$, and most preferably $C_1$–$C_{12}$ alkyl; $R_{14}$ represents a saturated or unsaturated, straight or branched chain hydrocarbyl radical, (preferably straight chain alkylene), typically $C_2$–$C_{30}$, preferably $C_2$–$C_{20}$, and most preferably $C_2$–$C_{16}$ alkylene; and m represents a number from 1 to about 6, preferably 1 to about 3. Typically, m is 1 when $R_{12}$ is $C_3$ alkanetriyl and can vary from 1 to about 6, preferably 1 to about 3 when $R_{12}$ is $C_2$ alkanetriyl. When m is greater than 1, formula VI' is meant to express alkoxylated derivatives of thioalkanols, such as ethoxylated derivatives.

Representative examples of suitable compounds falling within the scope of the above structural formulas VI' and VI" are shown below in Tables 1 and 2, in chart form, wherein each of the variable groups is associated with specific compounds. In selecting suitable compounds from Tables 1 and 2, collectively, at least one such compound must contain at least one -SCH₂CH₂OH group if the heterodialkanol of formula V does not contain any -SCH₂CH₂OH groups. In cases where the heterodialkanol of formula V does not contain any -SCH₂CH₀H groups, the selected compounds from Tables 1 and 2 which contain at least one -SCH₂CH₂OH group are employed to form episulfonium cations which are necessary for the desired reaction to occur. When the hydrocarbyl thioalkanol does not contain, an -SCH₂CH₂OH group, it represents a preferred species of nucleophilic reactant.

TABLE 1

| Formula | $R_{11}-S-(R_{12}O)_mH$ | | | VI' |
| | | $R_{13}$ | | |
| --- | --- | --- | --- | --- |
| $R_{11}$ | $R_{12}$ | $R_{13}$ | m | |
| $C_8H_{17}-$ | $-CH_2-CH-$ | $CH_3-$ | 1 | |
| $C_{10}H_{20}-$ | $-CH_2-CH-CH_2-$ | $C_2H_5-$ | 1 | |
| $C_{12}H_{25}-$ | $-CH_2-CH-$ | $H-$ | 1 | |
| $C_{14}H_{29}-$ | $-CH_2-CH-$ | $C_2H_5-$ | 2 | |
| $C_{15}H_{31}-$ | $-CH_2-CH-$ | $C_3H_7-$ | 3 | |

TABLE 1-continued

| Formula | $R_{11}-S-(R_{12}O)_mH$<br>$\quad\quad\quad\mid$<br>$\quad\quad\quad R_{13}$ | | | VI' |
|---|---|---|---|---|
| $R_{11}$ | $R_{12}$ | | $R_{13}$ | m |
| $C_{20}H_{40}-$ | $-CH_2-CH-$ | | $C_6H_{13}-$ | 3 |
| $C_{25}H_{51}-$ | $-CH_2-CH-$ | | $C_{12}H_{25}-$ | 1 |
| $C_{30}H_{61}-$ | $-CH_2-CH-CH_2-$ | | $C_{18}H_{37}-$ | 1 |

TABLE 2

| Formula $R_{11}-S-R_{14}-OH$ | | VI'' |
|---|---|---|
| $R_{11}$ | $R_{14}$ | |
| $C_8H_{17}-$ | $-C_2H_4-$ | |
| $C_{10}H_{20}-$ | $-C_3H_6-$ | |
| $C_{12}H_{25}-$ | $-C_4H_8-$ | |
| $C_{14}H_{27}-$ | $-C_{10}H_{20}-$ | |
| $C_{15}H_{31}-$ | $-C_{10}H_{20}-$ | |
| $C_{20}H_{40}-$ | $-C_2H_4-$ | |
| $C_{25}H_{51}-$ | $-C_5H_{10}-$ | |
| $C_{30}H_{61}-$ | $-C_{10}H_{20}-$ | |

When $R_{12}$ is $C_2$ alkanetriyl, the hydrocarbyl thioalkanol reactants of formula VI' may be prepared, for example, by heating together at a temperature of about 140° to about 160° C. an alkyl mercaptan and an epoxide compound in accordance with the following equation:

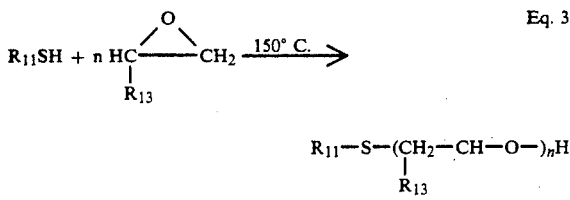

Eq. 3 where $R_{11}$ and $R_{13}$ are described above.

When $R_{12}$ is $C_3$ alkanetriyl, the hydrocarbyl thioalkanol reactant of formula VI' may be prepared, for example, by heating together in the presence of a free radical generator, such a benzoyl peroxide, an alkyl mercaptan and an alkenol in accordance with the following equation:

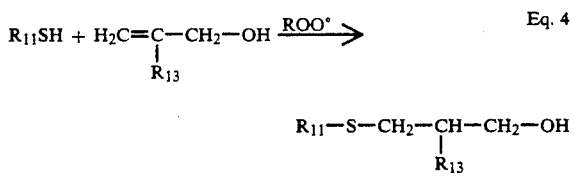

Eq. 4 where $R_{11}$ and $R_{13}$ are described above and ROO. represents an organic peroxide free radical initiator.

The hydrocarbyl thioalkanol reactant of formula VI'' may be prepared, for example, by mixing together in the presence of an alkaline catalyst, such as sodium hydroxide, an alkyl halide and a hydroxy alkyl mercaptan in accordance with the following equation:

Eq. 5

The heterodialkanol reactant (b)(ii) is characterized by the formula:

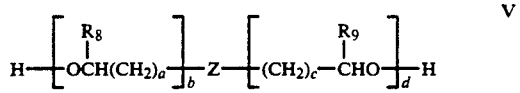

V where $R_8$ and $R_9$ each independently can represent hydrogen, and $C_1$ to about $C_{12}$ alkyl (preferably straight chain alkyl), preferably $C_1$ to about $C_6$ alkyl, and most preferably $C_1$ to about $C_3$ alkyl; Z is a linking group selected from $-S-$ (preferably $-S-$), $-S-S-$, $-O-$, and $>NR_{10}$, wherein $R_{10}$ is hydrogen, $C_1-C_{22}$ alkyl, preferably $C_1$ to about $C_{18}$ alkyl, and monohydroxy-substituted alkyl, preferably a terminal monohydroxy-substituted alkyl, the alkyl being as described above in connection with $R_8$ and $R_9$; a, b, c, and d each independently represent numbers which can vary from 1 to about 3, preferably 1 or 2. Preferably, $R_8$ and $R_9$ are the same, the numbers represented by b and d are the same, and the numbers represented by a and c are the same, thereby resulting in formula V defining a bisalkanol. Preferably the heterodialkanol reactant (b) (ii) contains at least one -SCH$_2$CH$_2$OH group; however, it is only necessary that at least one of the heterodialkanol reactant (b) (ii) or the hydrocarbyl thioalkanol reactant (b) (i) contain at least one -SCH$_2$CH$_2$OH. When the heterodialkanol does not contain an -SCH$_2$CH$_2$OH group, it constitutes another species of preferred nucleophilic reactant.

When Z is $-O-$, formula V can represent ethylene glycol and derivatives thereof; when Z is $>NR_{10}$, and $R_{10}$ is alkyl or hydrogen, formula V can represent a diethanolamine and derivatives thereof; when $R_{10}$ is a monohydroxy-substituted alkyl, such as $-(CH_2)_2OH$, formula V can represent triethanolamine and derivatives thereof.

If b or d are greater than 1, then formula V is meant to express alkoxylated derivatives of the heterodialkanols, such as ethoxylated derivatives.

The preferred heterodialkanols are thiodialkanols, wherein in formula V, Z is $-S-$, and $R_8$ and $R_9$ are, independently, hydrogen, ethyl or methyl.

In the most preferred thiodialkanols of formula V, a, b, c and d are each 1 or 2 (preferably 1), $R_8$ is hydrogen or methyl, $R_9$ is hydrogen, methyl or ethyl, and Z is sulfur.

Representative thiodialkanols include 2,2'-thiodiethanol; 3,3'-thiodipropanol; thio-bis ethoxyethanol; thiobisisopropoxyisopropanol; bis-(3-hydroxypropyl)disulfide; and mixtures thereof.

When Z is sulfur, the thiodialkanol reactants may be prepared, for example, in accordance with the above equation 1.

It will be appreciated that it is possible for both the hydrocarbyl thioalkanol component (b)(i) and the heterodialkanol component (b)(ii) to satisfy the above-described formula I for the beta-hydroxy thioether component.

The reaction of the organic phosphite ester reactant and the sulfur-containing reactant, is performed, for example, by mixing at least one member from each of the components (a), (b)(i) and (b)(ii), and heating the reaction mixture under reflux conditions in a suitable vessel at a reaction temperature of typically from about 75° to about 130° C., (e.g. 85° to about 120° C.) preferably from about 90° to about 118° C., (e.g. 95° to 115° C.), and most preferably from about 100° to about 115° C. for a period of time of typically from about 1 to about 24, preferably from about 4 to about 18, and most preferably from about 7 to about 12 hours.

During the course of reaction, organic alcohol derived from $R_5$ of formula II (i.e. the organic phosphite reactant) will be evolved. This alcohol by-product is not believed to contribute significantly to the desired properties of the final product mixture and preferably is continuously removed during the course of reaction, e.g., from the overhead using a nitrogen sweep. Typically, the identity of $R_5$ of the phosphite reactant is selected to facilitate alcohol removal.

The reaction may be monitored periodically to determine whether it has gone to completion by removing samples from the reaction mixture and subjecting the samples to infrared analysis. As the reaction proceeds, a hydrogen phosphite peak will appear (at 4.1 micron on the IR spectra) and its height will continue to grow over the course of the reaction. At the same time, the height of the hydroxyl peak (at 2.9 microns on the IR spectra) attributable to alcohol by-product, beta-hydroxy thioether, heterodialkanol, and hydrocarbyl thioalkanol will diminish. Accordingly, at some point in time during the reaction, the height of the hydrogen phosphite peak will exceed the height of the hydroxyl peak.

The reaction is terminated at any time after this point, and preferably before the point at which the hydroxyl peak disappears altogether.

The reaction product mixture can be stripped of low molecular weight alcohols, typically derived from the phosphite reactant, for safety reasons related to the flash point of such alcohols. In addition, the presence of low molecular weight alcohol in the product mixture typically results in eventual evaporation of the alcohol over time. This can induce phase separation, which in certain instances may not be desired, e.g., if one wants to use the entire product mixture. To avoid this occurrence, it is advantageous to replace the stripped alcohol with a higher molecular weight alcohol (e.g., $C_8$ to $C_{18}$ alcohol), such as tridecylalcohol. However, the addition of the higher molecular weight alcohol generally should not be conducted until the product mixture has cooled to below reaction temperature and typically is conducted at temperatures of from 20° to about 40° C. Otherwise, the higher molecular weight alcohol can enter into reaction with the product which may not be desirable.

Typically, the higher molecular weight alcohol is added to achieve a weight ratio of Product:Alcohol of from about 80:20 to about 95:5, preferably 90:10.

Under certain conditions, e.g. continuing the reaction beyond its intended end point, removing all of the alcohol by-product, or conducting the reaction at higher than the prescribed temperatures, the resulting product mixture tends to be present in two separate phases. Upon such phase separation, there is formed a top phase mixture enriched in non-phosphorous thioether-containing species and a bottom phase mixture enriched in phosphorous-containing species. Typically, the top phase comprises from 80 to 20 weight percent of the total mixture of reaction products and the bottom phase comprises about 20 to 80 weight percent of the total product mixture. The amount of phosphorous-containing species found in the bottom phase, based on the number of moles of phosphorous-containing reactant added to the reaction mixture, typically is from about 70 to about 95 mole percent.

It should be noted that both the top phase and bottom phase will each comprise at least some phosphorus-containing species and at least some non-phosphorous thioether-containing species.

The two phase mixture may be employed as such. However, it has been found that both the top phase mixture and the bottom phase mixture, independently, posses characteristics which render the separate phases useful as lubricant and fuel additives, and particularly useful as additives for automatic transmission fluids.

If phase separation does occur, the phases may be homogenized as described above with, for example, a suitable cosolvent such as tridecyl alcohol. However, the separate phases can be, and often are, used independently from one another.

In a less preferred embodiment, the reactive components can be added and mixed sequentially, provided that the mixing is complete prior to attaining the reaction temperatures specified above.

The ratio of total molar equivalents of hydroxy groups in the sulfur-containing reactants (b)(i) and (b)(ii) collectively to the moles of phosphorous contained in the phosphite reactant in the reaction mixture is controlled to be typically about 1 to 5:1, preferably about 2 to 4:1, and most preferably about 2.5 to 3.5:1. In one preferred aspect, the ratio of molar equivalents of $-SCH_2CH_2OH$ groups to moles of phosphorous in the phosphorous-containing reactant is from about 0.1 to 2:1 (e.g. 0.5 to 1.5:1), preferably about 1:1.

The top phase can be conveniently separated form the bottom phase by decanting, using a separatory funnel, or any other means commonly known in the art for separating a heterogeneous two phase mixture.

The single phase mixture of reaction products prepared in accordance with the invention comprises:

(i) non-phosphorous containing compounds having within their structure at least one group represented by the formula:

$$-S-CH_2CH_2-Q- \qquad I'''$$

wherein Q is independently selected from the group consisting of oxygen or sulfur, said Q constituting a portion of the residue derived from: (1) beta-hydroxy thioether reactant (the $-SCH_2CH_2OH$ group-containing reactant or reactants), (2) the hydrocarbyl portion of the organic phosphite reactant, (3) when present, the nucleophilic reactant, and (4) mixtures of (1) to (3); and wherein the remainder of Structure I''', exclusive of Q, contains residue of beta-hydroxy thioether reactant; and;

(ii) phosphorous containing compounds comprising phosphorous acid and organic phosphites having within their structure at least one group represented by the formula:

$$R-SCH_2CH_2O- \qquad I'$$

bonded directly to the phosphorous atom of the organic phosphite, said $R-SCH_2CH_2O-$ group representing a residue of beta-hydroxy thioether.

As indicated above, the single phase mixture of reaction products may separate into a top phase mixture and a bottom phase mixture. The top phase consists primarily of a mixture of thioether-containing species and contains relatively small quantities of phosphorous-containing species.

It should be noted that the terms non-phosphorous-containing species or thioether containing species (sometimes referred to as non-phosphorous thioether-containing species) as used herein, for example, in conjunction with the top phase, are intended to collectively represent a material which contains at least the —S— (i.e. thioether species) but also the —O— (i.e. oxyether species) in the same molecule. For example when an -SCH$_2$CH$_2$OH group reacts, via the episulfonium cation intermediate, with a hydroxyl group of another reactant molecule the species -SCH$_2$CH$_2$O— is formed. Thus, the complexity of product mixture constituting the thioether containing species is a function of the complexity of the initial starting reactants. In all instances, however, the thioether product will always contain at least one -SCH$_2$CH$_2$-Q- product where Q is S or most preferably —O—. Difunctional reactants (e.g. those which contain two hydroxyl groups (including the hydroxyl group present on an -SCH$_2$CH$_2$OH group) will contain at least two -SCH$_2$CH$_2$Q- groups, and so forth.

For example, the top phase produced in accordance with Example 9 (Additive 9B) was analyzed and characterized by capillary (GC) and GC/Mass spectra (GC/MS). GC/MS spectra were obtained in both electron-impact (EI) mode at 70 eV for fragmentation patterns and chemical ionization (CI) mode, using methane as reagent gas, for molecular weight information.

Because reference materials could not be obtained for most of the compounds identified in this sample quantitation was estimated using capillary GC/Flame ionization detector (FID) area percent. Results of these analyses are summarized in Table 3.

TABLE 3

| Top Phase Products | |
|---|---|
| Formula | Relative % Normalized to 100% |
| $\overset{O}{\underset{\|}{H-P}}-(OC_4H_9)_2$ | 0.3 |
| C$_4$H$_9$OCH$_2$CH$_2$SCH$_2$CH$_2$OC$_4$H$_9$ | 7.2 (Comp.-2C) |
| C$_{12}$H$_{25}$SCH$_2$CH$_2$OC$_4$H$_9$ | 37.2 (Comp.-2A) |
| (C$_4$H$_9$OCH$_2$CH$_2$SCH$_2$CH$_2$)$_2$O | 3.9 |
| C$_{12}$H$_{25}$SCH$_2$CH$_2$SCH$_2$CH$_2$OC$_4$H$_9$ | 2.2 |
| C$_{12}$H$_{25}$SCH$_2$CH$_2$OCH$_2$CH$_2$SCH$_2$CH$_2$OC$_4$H$_9$ | 18.6 (Comp.-1) |
| C$_{12}$H$_{25}$SCH$_2$CH$_2$SC$_{12}$H$_{25}$ | 3.0 |
| (C$_{12}$H$_{25}$SCH$_2$CH$_2$)$_2$O | 17.2 (Comp.-2B) |
| Unknown | 10.4 |

As can be seen from the above, the major components of the analyzed top phase have been labeled Components-1, 2A, 2B, and 2C. It will be noted further that each component in the top phase contains at least one group corresponding, to -SCH$_2$CH$_2$Q- as defined herein.

Generalizing from this data, the following generic formula XIII was constructed, although other representations will be possible depending on the nature of starting reactants:

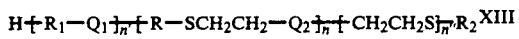

$$H + R_1 - Q_1 \}_{n'} + R - SCH_2CH_2 - Q_2 \}_{n} + CH_2CH_2S \}_{n''} R_2 \quad XIII$$

wherein R$_1$ and R$_2$ independently represent inertly substituted or unsubstituted C$_1$ to C$_{30}$ aliphatic hydrocarbyl, C$_6$-C$_{14}$ aromatic hydrocarbyl, mixed aromatic/aliphatic hydrocarbyl wherein the aromatic and aliphatic portions thereof are as described above; each R independently represents C$_1$ to C$_{30}$ aliphatic hydrocarbyl, aromatic hydrocarbyl, and mixed aromatic/aliphatic hydrocarbyl, independently as described in connection with R$_1$; Q$_1$ and Q$_2$ independently represent oxygen or sulfur; n is a number of from 1 to about 4; n' is an integer of zero or 1 ; and n" is an integer of zero or one subject to the provisos that:

(1) n" is zero when:
  (a) n' is 1; or
  (b) n' is zero and n is greater than 1;
(2) when n" is zero:
  (a) and n' is 1, at least one of Q$_1$ and the terminal Q$_2$ bound directly to R$_2$ is oxygen; and
  (b) n' is zero, and n is greater than 1, Q$_2$ is oxygen; and
  (c) n is 1, Q$_2$ can represent sulfur or oxygen; and
(3) said composition is comprised of a mixture of a first Component-1 and at least one second component selected from Component-2A and Component-2B, and optionally Component-2C wherein:
  (i) said Component-1 is represented by formula XIII wherein n' is 0, n is greater than 1 and n" is zero;
  (ii) said Component-2A is represented by formula XIII wherein n' is zero, n is 1, n" is zero and Q$_2$ is oxygen;
  (iii) said Component-2B is represented by formula XIII wherein n' is zero, n is 1 and n" is 1; and
  (iv) said Component-2C is represented by formula XIII wherein n' is 1, n is 1 and n" is 0.

In one preferred embodiment the top phase mixture of thioether-containing species comprises at least Component-1 and Component-2A; in another preferred embodiment the top phase mixture comprises at least Component-1 and Component-2B; in another preferred embodiment the top phase mixture comprises Component-1, Component-2A and Component 2-B; and in yet another preferred embodiment the top phase mixture comprises all of the Components 1, 2A, 2B and 2C.

Typically thioether-containing species characterized as Component-1 include those wherein in formula XIII, n' is 0, n is 3; n" is 0; R$_1$ is C$_{10}$ to C$_{14}$ alkylene, R is C$_1$ to C$_{30}$ alkylene (typically C$_2$–C$_{14}$ alkylene); and R$_2$ is selected from the group consisting of C$_1$ to C$_{30}$ straight chain aliphatic hydrocarbyl (preferably C$_1$–C$_{10}$ alkyl), C$_6$ aryl, alkaryl wherein the alkyl potion thereof represents C$_1$ to C$_{24}$ alkyl and the aryl portion is as described above. An example of Component-1 is C$_{12}$H$_{25}$SCH$_2$CH$_2$OCH$_2$CH$_2$SCH$_2$CH$_2$OC$_4$H$_9$.

Typical thioether-containing specie characterized as Component-2A include those wherein in formula XIII n' and n" are zero; n is 1; R is C$_2$ to C$_{14}$ alkylene, typically C$_{10}$–C$_{14}$ alkylene; and R$_2$ is C$_1$ to C$_{10}$ alkyl. An example of Component-2A is C$_{12}$H$_{25}$SCH$_2$CH$_2$OC$_4$H$_9$.

Representative species characterized as Component-2B include those wherein in formula XIII n' is 0; n is 1; n" is 1; R$_2$ is C$_{10}$ to C$_{14}$ alkyl; and R is C to C$_{14}$ alkylene. An example of Component-2B is C$_{12}$H$_{25}$SCH$_2$CH$_2$OCH$_2$CH$_2$SC$_{12}$H$_{25}$.

Representative species characterized as Component-2C include those in which Q$_1$ and Q$_2$ are oxygen; R$_1$ is C$_1$ to C$_{10}$ alkylene; R$_2$ is C$_1$–C$_{10}$ alkyl; and R is C$_2$ to C$_{14}$ alkylene. An example of Component-2C is C$_4$H$_9$OCH$_2$CH$_2$SCH$_2$CH$_2$OC$_4$H$_9$.

Typically, the relative amounts of the major Components 1, 2A, 2B and 2C in typical top phase mixtures prepared in accordance with the invention will vary depending upon the choice of reactants and reaction conditions. Normally, however, Component-1 is present in an amount up to about 50% by weight, based upon the total composition. Similarly, Component-2A is present in an amount up to about 60% by weight, typically about 25 to 75% by weight; Component-2B is present in an amount up to about 60% by weight, typically about 10 to 40% by weight; and Component-2C is present in an amount up to about 25% by weight, typically from 5 to 15% by weight.

As a generalization from the data provided in the examples, the constituents of the product mixture of the bottom phase can be divided into three categories, namely: (1) organic phosphorous-containing species, (2) phosphorous acid, and (3) non-phosphorous containing thioether-containing species.

The organic phosphorous containing species comprise those characterized by the presence within their structure of at least one group represented by the formula I':

$$R\text{-}SCH_2CH_2O- \qquad \text{I'}$$

bonded directly to the phorphorous atom of the organic phosphorous species, wherein the R-SCH$_2$CH$_2$O— group represents a residue of beta-hydroxy thioether.

While not all of the organic phosphorous containing species present in the bottom phase must possess hydrocarbyl groups conforming to the R-SCH$_2$CH$_2$O— formula, at least some of said species must possess at least one hydrocarbyl group containing residue of beta-hydroxy thioether.

Those hydrocarbyl groups present in the organic phosphorous containing species of the bottom phase not derived from beta-hydroxy thioether will comprise those derived from the optional nucleophilic reactant and/or the hydrocarbyl group originally present in the organic phosphite reactant.

The organic phosphorous-containing species in turn can be categorized as comprising (a) organic phosphites, e.g., monohydrocarbyl phosphites and dihydrocarbyl hydrogen phosphites; (b) organic phosphonates and (c) alkyl thylphosphites.

Such organic phosphorous-containing species can be represented by the following structural formulas:

$$\begin{array}{c} HO\diagdown \;\; O \\ \phantom{HO}\diagdown \|\phantom{O} \\ \phantom{HOO}P-H \\ \diagup \\ "R" \end{array} \qquad \text{VII}$$

(monohydrocarbyl phosphite)

$$\begin{array}{c} HO\diagdown \;\; O \\ \phantom{HO}\diagdown \|\phantom{O} \\ \phantom{HOO}P-H \\ \diagup \\ HO \end{array} \qquad \text{VII'}$$

(phosphorous acid)

$$\begin{array}{c} "R"\diagdown \;\; O \\ \phantom{"R"}\diagdown \|\phantom{O} \\ \phantom{"R"O}P-H \\ \diagup \\ "R" \end{array} \qquad \text{VIII}$$

(dihydrocarbyl hydrogen phosphite)

-continued $$\begin{array}{c} "R"\diagdown \;\; O \\ \phantom{"R"}\diagdown \|\phantom{O} \\ \phantom{"R"O}P-S-R \\ \diagup \\ H \end{array} \qquad \text{IX}$$

(hydrocarbylthyl phosphite)

$$\begin{array}{c} "R"\diagdown \;\; O \\ \phantom{"R"}\diagdown \|\phantom{O} \\ \phantom{"R"O}P-R" \\ \diagup \\ "R" \end{array} \qquad \text{X}$$

(phosphonate)

wherein each "R", independently, represents the same or different residue form (i) beta hydroxy thioether reactant, i.e., R-SCH$_2$CH$_2$O—, (ii) nucleophilic reactant, when employed, e.g., R$_7$-O— and (iii) the hydrocarbyl oxy residue from the starting phosphite reactant, e.g., R$_5$-O—; and R" represents residue of any of the reactants, as defined in connection with "R" with the exception that the bridging oxy group linking said "R" residue to phosphorous is absent.

When "R" represents a residue of beta-hydroxy thioether reactant, it can be depicted as follows:

$$(HOCH_2CH_2S)_{x-1}\text{-}R\text{-}SCH_2CH_2O- \qquad I_1$$

wherein R is as described in connection with formula I, and wherein x is a number of from 1 to 3 and x-1 identifies the number of additional -SCH$_2$CH$_2$OH groups which may be attached directly to R.

When "R" represents beta-hydroxy thioether derived from heterodialkanol represented by formula V, it can be depicted as follows:

$$H\!-\!\!\left[\!OCH\!-\!(CH_2)_a\!\underset{R_8}{|}\right]_b\!\!-\!Z\!-\!\!\left[\!(CH_2)_c\!-\!CHO\!\underset{R_9}{|}\right]_d\!\!- \qquad V_1$$

wherein R$_8$, R$_9$, a, b, c, d, and Z are as described in connection with formula V.

When "R" represents residue of beta-hydroxy thioether derived form formulas VI' and VI", it can be depicted as follows:

$$R_{11}\!-\!S\!-\!\!\left[\!\begin{array}{c}R_{12}O\\ |\\ R_{13}\end{array}\!\right]_m\!\!- \qquad VI_{1'}$$

or $$R_{11}\!-\!S\!-\!R_{14}\!-\!O- \qquad VI_{1''}$$

wherein R$_{11}$, R$_{12}$, R$_{13}$, R$_{14}$ and m are as described in connection with formulas VI' and VI".

When "R" represents residue of nucleophilic reactant derived form formulas IV, IV' and IV", it can be depicted by the following formulas respectively:

$$(HL)_{\overline{n'-1}}R_7\text{-}L \qquad IV_1$$

$$H\!+\!O\!-\!R_{29}\!\!\underset{\overline{b}}{\,}Z\!+\!R_{29}\!-\!O\!\underset{\overline{d}}{\,} \qquad IV_{1'}$$

$$[H\!-\!(O\!-\!R_{29})_{n'''}\!-\!Z\!\underset{\overline{n'''-1}}{\,}R_7\!-\!Z\!-\!(R_{29}\!-\!O)_{n'''}- \qquad IV_{1''}$$

wherein $R_7$, $R_{29}$, L, n', n", n"' and Z are as described above in connection with formulas IV, IV', and IV".

Of the species constituting the organic phosphorous-containing species, the hydrocarbyl phosphites predominate. However, with regard to all phosphorous-containing species in the bottom phase, phosphorous acid predominates.

It is the combined presence of the complex mixture of organic phosphorous-containing species and non-phosphorous-containing thioether species which are believed to be responsible for the anti-wear performance observed to be present in the single phase product mixture as well as the separate top and bottom phase mixtures.

The collective amounts of material represented by formulas VII through X and VII' described above have been deduced from $^{31}$P NMR analysis of the product mixture.

The most accurate measurements were taken at 40° C. on a JEOL GSX-400 NMR Spectrometer operating at 161.70 MHz. Samples were all prepared to be between 20 and 30% wt/wt in $CDCl_3$. Standard single pulse experiments were used with a preacquisition pulse delay of 6 sec and 45° observe flip angle. All broadband $^1$H decoupling was gated off during preacquisition and evolution and on during data acquisition. These conditions assure that the observed signals are relatively quantitative.

Chemical shifts reported are referenced to concentrated $H_3PO_4$ contained externally in a capillary tube. The spectral observation window was selected to be 35211.3 Hz or 2 times the normal chemical shift range with 32K data points per scan. All fast Fourier transforms were done with a normal gaussian line broadening of 1-4 Hz. Integration intensities were digitally measured and the values were normalized to mole percents.

In view of the $^{31}$P NMR analysis, is believed that essentially all of the hydrocarbyloxy groups of the original phosphite reactant are replaced with hydrogen, OH, R", and/or "R", groups. During the course of this replacement, the phosphorous valence changes from +3 to +5 to form the compounds of formulas VII to X. It will be observed, also, that each organo phosphorous-containing species of the depicted product mixture must contain some "R" groups derived from the sulfur-containing reactant and/or the nucleophilic reactant, although not necessarily on the same molecule.

Figure 2:
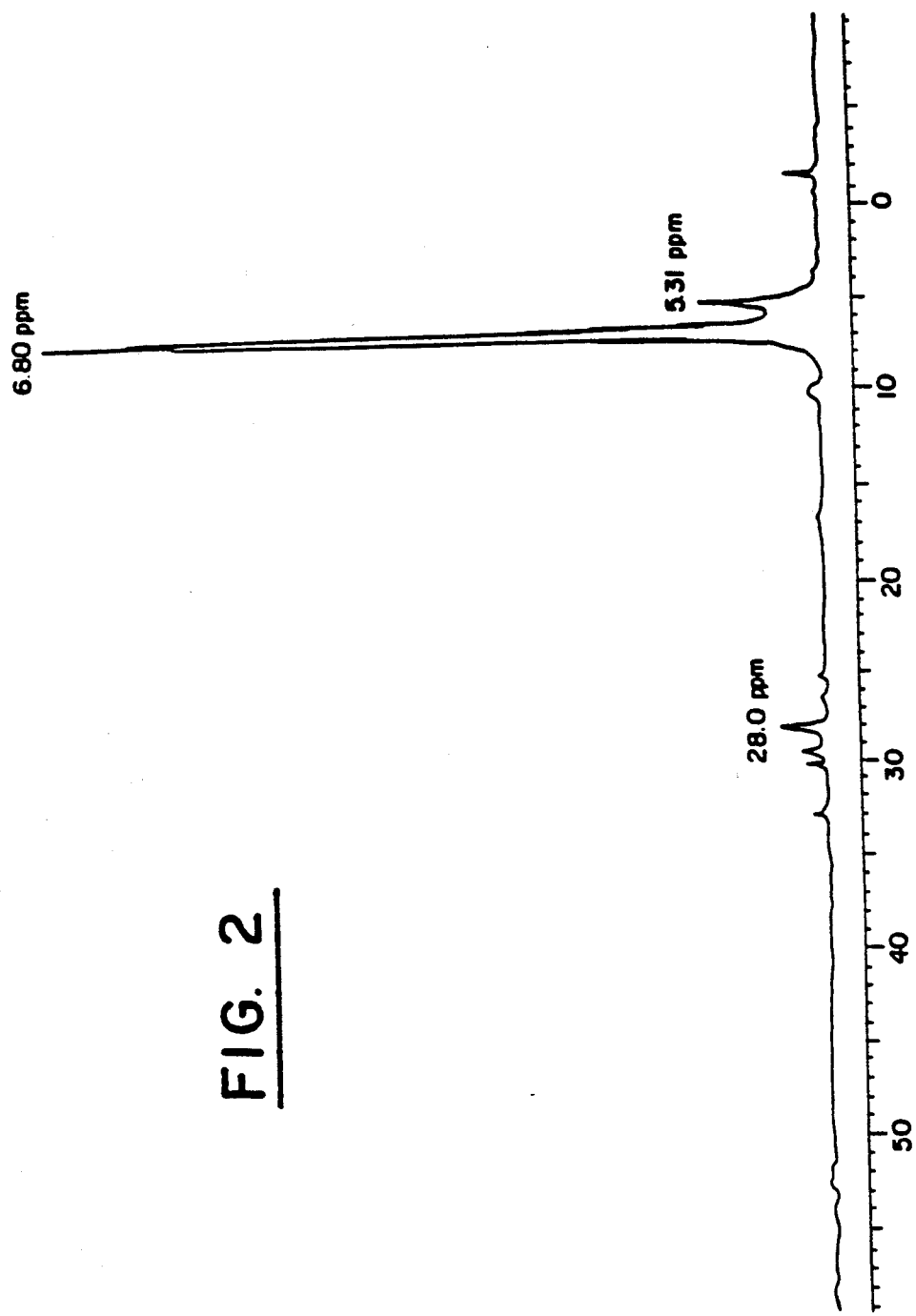
FIG. 2 is an enlarged view of a portion of FIG. 1.

FIGS. 1 and 2 (an enlargement of FIG. 1) illustrate a typical $^{31}$P NMR spectral data tracing for products formed by the reacting tributyl phosphite, 2-n-dodecylthioethanol and thiobisethanol, generally in accordance with the procedure described in the EXAMPLES hereinafter. With reference to the Figures, there is shown a spectral peak in region A (defined by the arrows 1—1 in FIG. 1) at 28.0 ppm (FIG. 2) relative to the externally contained $H_3PO_4$ reference and dual peaks in Region B (defined by the arrows 2—2 in FIG. 1) at 6.80 ppm (FIG. 2) and 5.31 ppm (FIG. 2) respectively. The peak at 28.0 ppm is attributable to the presence in the test sample of reaction products of formula X, whereas the peaks at 6.80 ppm and 5.31 ppm are attributable to reaction products of formulas VII and VIII. As indicated by the arrows 1—1, Region A covers the delta $^{31}$P scale range of from 39.2 ppm to 23.4 and has an integrated area intensity of 1.00; and Region B, covers the delta $^{31}$P scale range of from 14.2 ppm to −3.0 ppm and has an integrated area intensity of 8.93. The integrated area intensity values, which represent the digital values as determined by the spectrometer for the given frequency ranges, are used to calculate the mole % of the various reaction products The mole % is calculated by dividing the integrated area intensity in each of Regions A and B by the sum of the integrated area intensities, and then multiplying each fraction by 100%.

Figure 3:
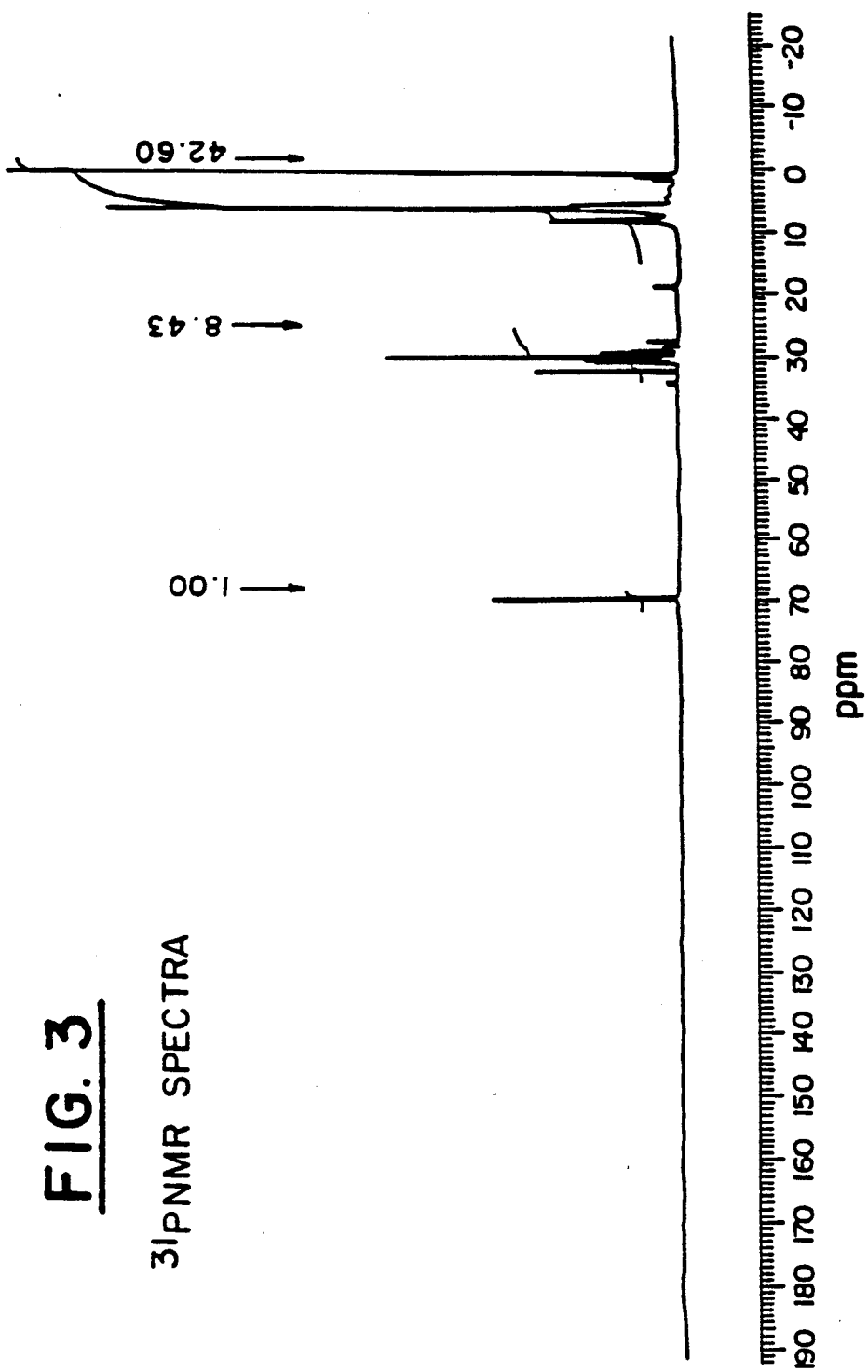
FIG. 3 is a $^{31}P$ NMR spectra for the top phase mixture obtained by reacting equal molar ratios of tributylphosphite hydroxyethyl n-dodecyl sulfide and thiobisethanol at a temperature on the order of about 95°–115° C. and then permitting the reaction products to separate into a top phase mixture and a bottom phase mixture.
Figure 4:
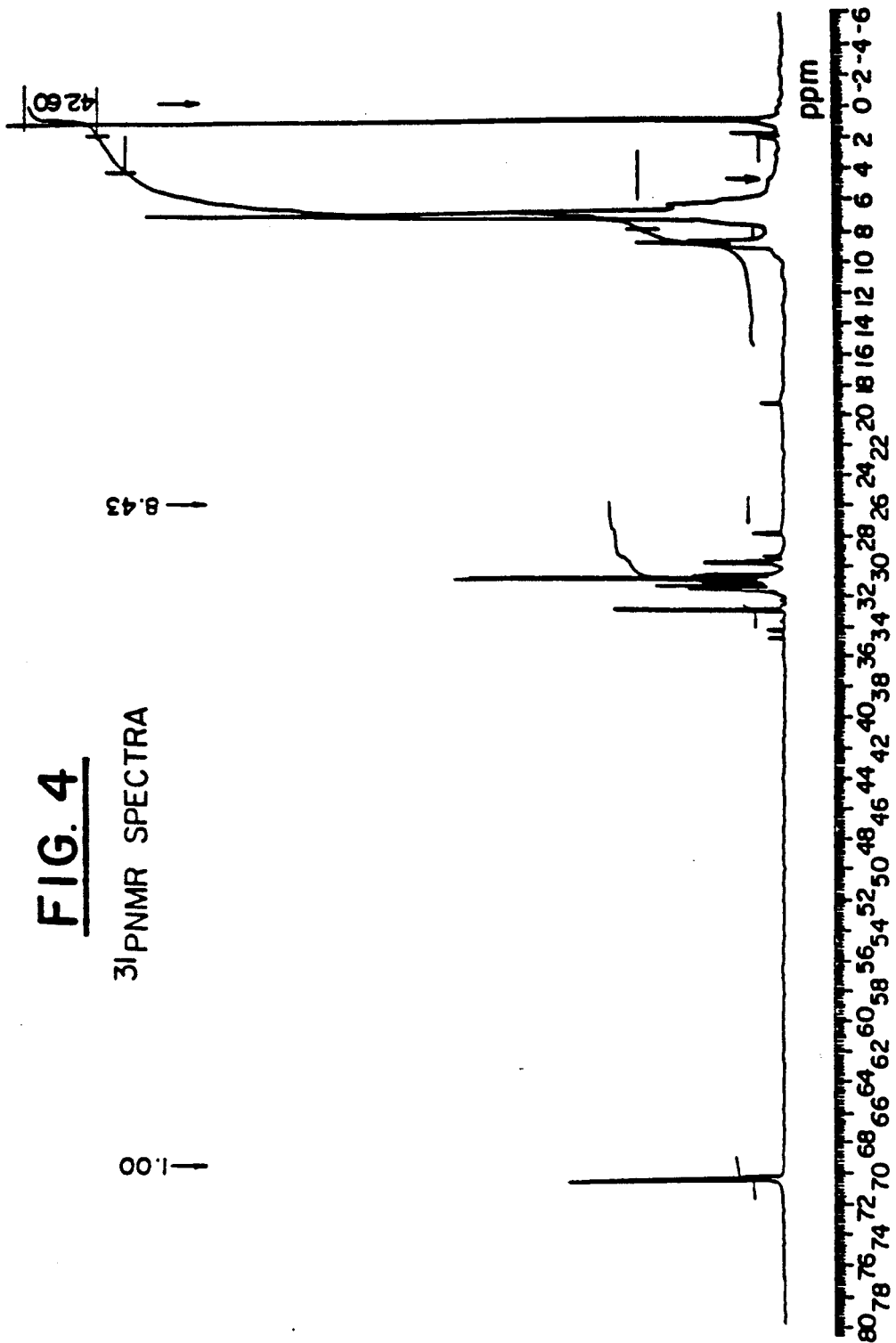
FIG. 4 is an enlarged view of a portion of FIG. 3.
Figure 5:
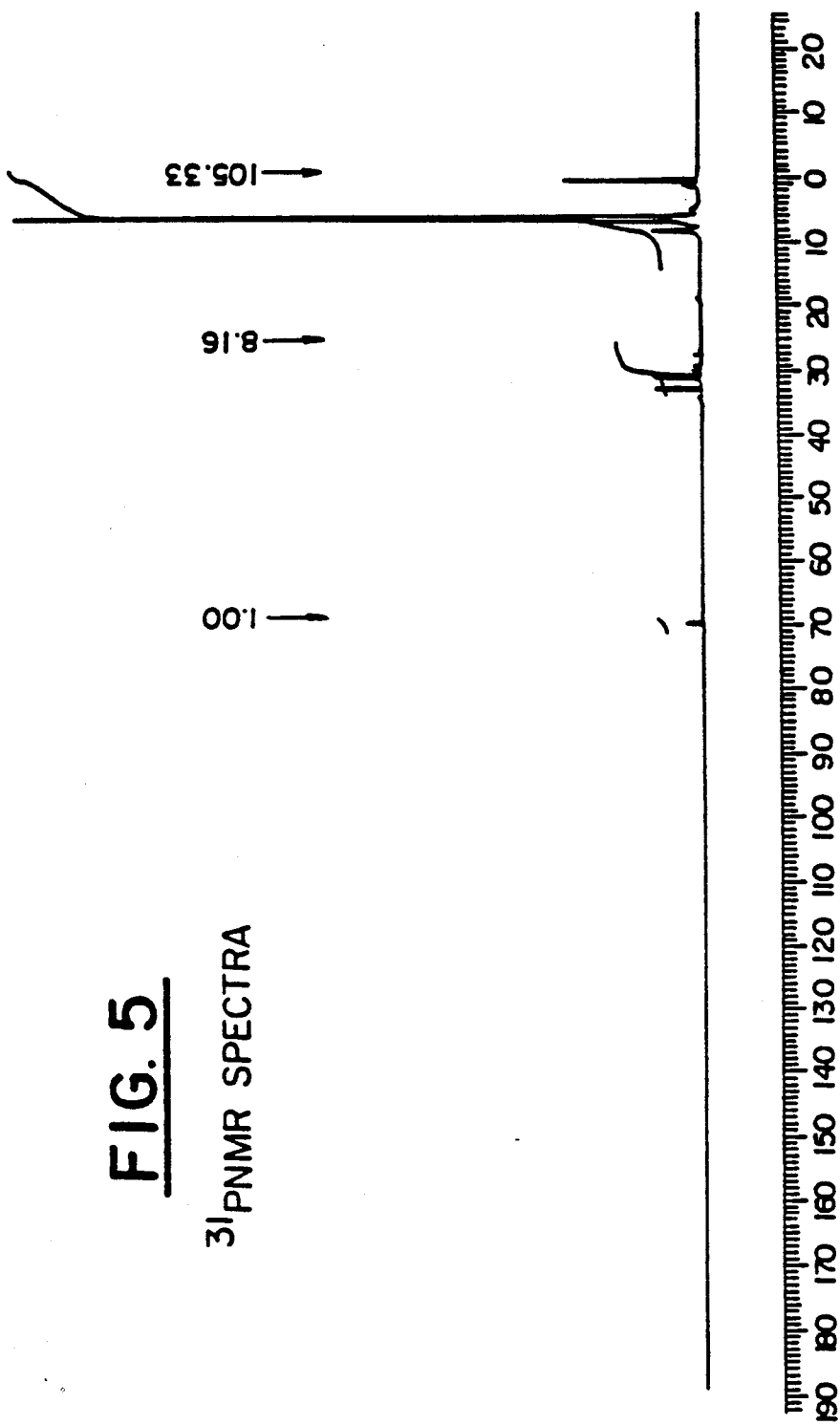
FIG. 5 is a $^{31}P$ NMR spectra for the bottom phase mixture obtained by reacting equal molar ratios of tributyl phosphite hydroxyethyl n-dodecyl sulfide and thiobisethanol at a temperature on the order of 95°–115° C., and then permitting the reaction products to separate into a top phase and a bottom phase mixture.
Figure 6:
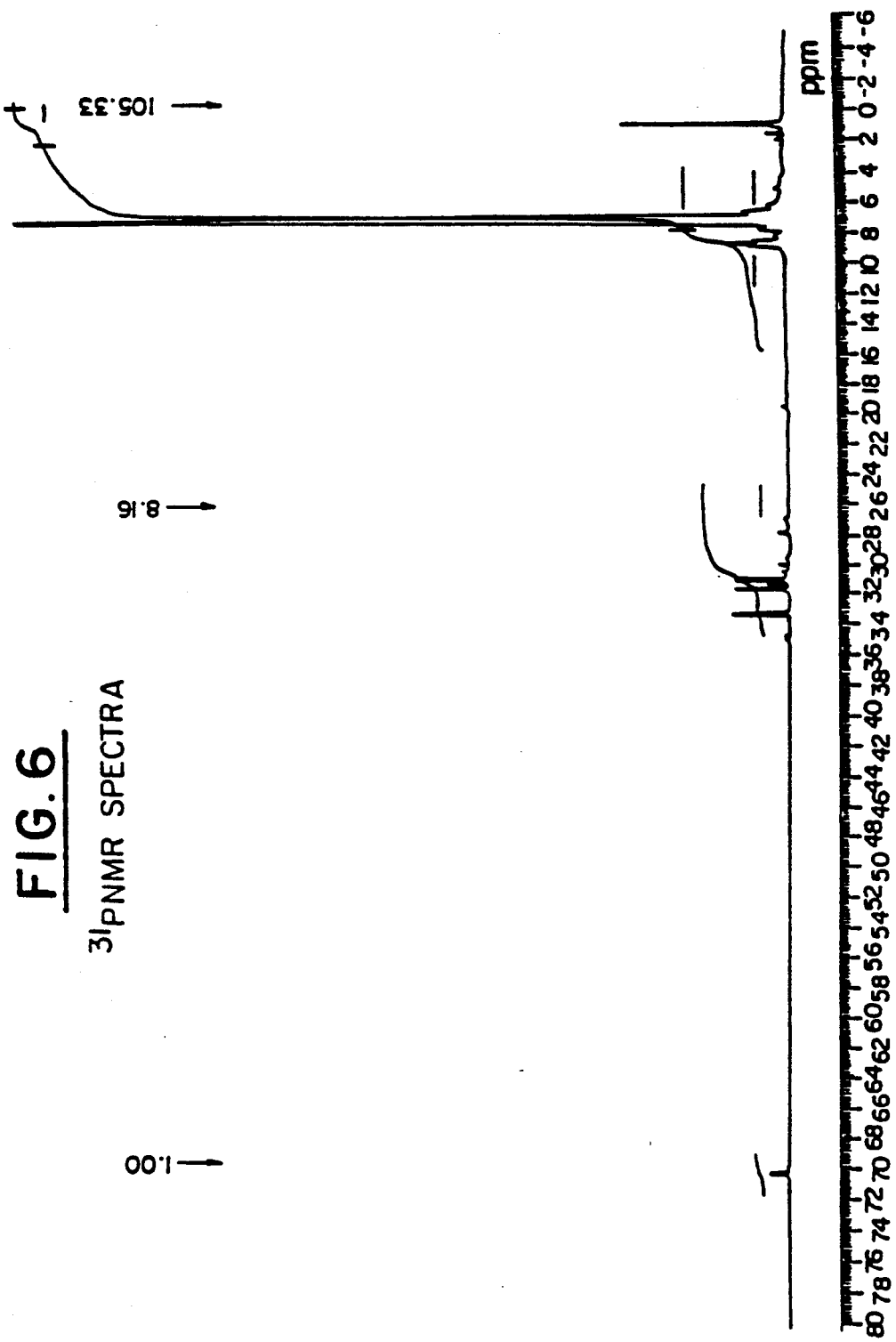
FIG. 6 is an enlarged view of a portion of FIG. 5.

FIGS. 3, 4, 5 and 6 are $^{31}$P NMR spectral tracings for products formed by reacting dibutyl hydrogen phosphite, thiobisethanol and 1-hydroxy-3-thiapentadecane as described in EXAMPLE 10. With reference to the Figures, FIGS. 3 and 4 are tracings of the top phase derived from allowing the reaction product to separate. FIG. 3 is a tracing of the entire spectral region 0 to 190 ppm shift and FIG. 4 is an expansion of the 0 to 80 ppm region. In FIG. 4 (and FIG. 3 as well) the sharp singlet peak at approximately 1 ppm is a small amount of unidentified phosphorous-containing material. The large peak at approximately 7 ppm is attributed to Formula VII and the small shoulder closer to 6 ppm is a minor amount of phosphorous acid (Formula VII'). This small shoulder in FIG. 4, when compared to the analogous peak in FIG. 6, shows that most of the phosphorous acid product resides in the bottom phase.

Referring again t FIGS. 3 and 4 (top phase tracings), the peak at 9 ppm is attributed to Formula VIII. The group of peaks at 28 to 34 ppm are attributable to structures of the type X while the sharp spike at 70 ppm is believed to caused by structure IX. Digital integration of the peak areas gives the relative mole percents of the various phosphorous-containing species in the top phase product as shown below:

| Phosphorous Species | Mole % |
| --- | --- |
| VII | 57 |
| VII | 4 |
| VIII | 13 |
| IX | 2 |
| X | 16 |

FIGS. 5 and 6 are $^{31}$P NMR tracings of the bottom phase derived from allowing the reaction product of EXAMPLE 10 to separate. FIG. 5 is a tracing of the entire spectral region 0 to 190 ppm shift, and FIG. 6 is an expansion of the 0 to 80 ppm region. In FIG. 6 (and FIG. 5 as well) the small spike at about 1 ppm is an unidentified phosphorous containing species. The large peak at about 7 ppm is attributable to phosphorous acid, Formula VII'. A small shoulder at 7.5 ppm is most likely due to Formula VII and the peak at 8.5 ppm is attributable to Formula VIII. The complex group of peaks form 28 to 34 ppm are attributable to Formula X and the small spike at 70 ppm is most likely due to Formula IX. Digital integration of the peak areas gives the relative mole percents of the phosphorous-containing species in the bottom phase as follows:

| Phosphorous Species | Mole % |
| --- | --- |
| VII | 8 |
| VII | 80 |
| VIII | <1 |
| IX | <1 |
| X | 7 |

It has been found that the mixed or single phosphorous- and sulfur-containing reaction product mixture of this invention, as well as the separate top phase and bottom phase mixtures, possess excellent anti-wear and anti-oxidation properties.

Accordingly, the various reaction product mixtures of the invention are used by incorporation and dissolution or dispersion into an oleaginous material such as fuels and lubricating oils.

The additives produced in accordance with the present invention have been found to be useful in fuel oils and lubricating oils. The normally liquid fuel oils are generally derived from petroleum sources, e.g., normally liquid petroleum distillate fuels, though they may include those produced synthetically by the Fischer-Tropsch and related processes, the processing of organic waste material or the processing of coal, lignite or shale rock. Such fuel compositions have varying boiling ranges, viscosities, cloud and pour points, etc., according to their end use as is well know to those of skill in the art. Among such fuels are those commonly known as diesel fuels, distillate fuels e.g., gasoline, heating oils, residual fuels, bunker fuels, etc., which are collectively referred to herein as fuel oils. The properties of such fuels are well known to skilled artisans as illustrated, for example, by ASTM Specification D #396-73, available from the American Society for Testing Materials, 1916 Race street, Philadelphia, Pa. 19103.

Middle distillate fuel oils include distillates boiling from about 120° to 725° F. (e.g., 375° to 725° F.), including kerosene, diesel fuels, home heating fuel oil, jet fuels, etc., and most preferably whose 20% and 90% distillation points differ by less than 212° F., and/or whose 90% to final boiling point range is between about 20° and 50° F. and/or whose final boiling point is in the range of 600° to 700° F.

The present reaction product mixtures, whether the single or mixed phase mixture, the top phase mixture, or the bottom phase mixture find their primary utility in lubricating oil compositions which employ a base oil in which one or more of the mixtures are dissolved or dispersed.

Such base oils may be natural or synthetic although the natural base oils will derive a greater benefit.

Thus, base oils suitable for use in preparing lubricating compositions of the present invention include those conventionally employed a crankcase lubricating oils for spark-ignited and compression-ignited internal combustion engines, such as automobile and truck engines, marine and railroad diesel engines, and the like. Particularly advantageous results are achieved by employing at least one of the phosphorous- and sulfur-containing product mixtures of the present invention in base oils conventionally employed in power transmitting fluids such as automatic transmission fluids, tractor fluids, universal tractor fluids and hydraulic fluids, heavy duty hydraulic fluids, power steering fluids and the like. Gear lubricants, industrial oils, pump oils and other lubricating oil compositions can also benefit from the incorporation therein of the phosphorous- and sulfur-containing reaction product mixtures of the present invention.

Thus, the reaction product mixtures of the present invention may be suitably incorporated into synthetic base oils such as alkyl esters of dicarboxylic acids, polyglycols and alcohols; polyalphaolefins, alkyl benzenes, organic esters of phosphoric acids, polysilicone oil, etc.

Natural base oils include mineral lubricating oils which may vary widely as to their crude source, e.g. whether paraffinic, naphthenic, mixed paraffinic-naphthenic, and the like; as well as to their formation, e.g. distillation range, straight run or cracked, hydrofined, solvent extracted and the like.

More specifically, the natural lubricating oil based stocks which can be used in the compositions of this invention may be straight mineral lubricating oil or distillates derived from paraffinic, naphthenic, asphaltic, or mixed base crudes, or, if desired, various blended oils may be employed as well as residuals, particularly those from which asphaltic constituents have been removed. The oils may be refined by conventional methods using acid, alkali, and/or clay or other agents such as aluminum chloride, or they may be extracted oils produced, for example, by solvent extraction with solvents such as phenol, sulfur dioxide, furfural, dichlorodiethyl ether, nitrobenzene, crotonaldehyde, etc.

The lubricating oil base stock conveniently has a viscosity of typically about 2.5 to about 12, and preferably about 3.5 to about 9 cst. at 100° C.

Thus the reaction product mixtures of the present invention can be employed in a lubricating oil composition which comprises lubricating oil, typically in a major amount, and a reaction product mixture typically in a minor amount, which is effective to impart enhanced anti-wear and friction stability properties relative to the absence of the additive mixture. Additional conventional additives selected to meet the particular requirements of a selected type of lubricating oil composition can be included as desired.

The reaction product mixtures of this invention are oil soluble, dissolvable in oil with the aid of a suitable solvent, or are stably dispersible in oil. Oil soluble, dissolvable, or stably dispersible, as that terminology is used herein, does not necessarily indicate that the materials are soluble, dissolvable, miscible, or capable of being suspended in oil in all proportions. It does mean, however, that the respective components of the mixture are soluble or stably dispersible in oil to an extent sufficient to exert their intended effect in the environment in which the oil is employed. Moreover, the incorporation of a dispersant, friction modifier and/or other additives may also permit incorporation of higher levels of a particular reaction product mixture if desired.

A phosphorous- and sulfur-containing reaction product mixture additive of the present invention can be incorporated into the lubricating oil in any convenient way. Thus, a product mixture can be added directly to the oil by dispersing, or dissolving the same in the oil at the desired level of concentration typically with the aid of the suitable solvent such as dodecylbenzene or naphthalene base stock. Such blending can occur at elevated temperatures of 60°-100° C.

The lubricating oil base stock for the additive mixtures of the present invention typically is adapted to perform a selected function by the incorporation of additives therein to form lubricating oil compositions (i.e., formulations).

As indicated above, one broad class of lubricating oil compositions suitable for use in conjunction with the additives of the present invention are power steering fluids, tractor fluids, tractor universal oils, and the like.

The benefits of the additives of the present invention are particularly significant when employed in a lubricating oil adapted for use as an automatic transmission fluid.

Power transmitting fluids, such as automatic transmission fluids, as well as lubricating oils in general, are typically compounded from a number of additives each useful for improving chemical and/or physical properties of the same. The additives are usually sold as a concentrate package in which mineral oil or some other base oil is present. The mineral lubricating oil in automatic transmission fluids typically is refined hydrocarbon oil or a mixture of refined hydrocarbon oils selected according to the viscosity requirements of the particular fluid, but typically would have a viscosity range of 2.5–9, e.g. 3.5–9 cst. at 100° C. Suitable base oils include a wide variety of light hydrocarbon mineral oils, such as naphthenic base oils, paraffin base oils, and mixtures thereof.

Representative additives which can be present in such packages as well as in the final formulation include viscosity index (V.I.) improvers, corrosion inhibitors, oxidation inhibitors, friction modifiers, lube oil flow improvers, dispersants, anti-foamants, anti-wear agents, detergents, metal rust inhibitors and seal swellants.

Viscosity modifiers impart high and low temperature operability to the lubricating oil and permit it to maintain sufficient viscosity at elevated temperatures and also exhibit acceptable viscosity or fluidity at low temperatures.

V.I. improvers are generally high molecular weight hydrocarbon polymers or more preferably polyesters. The V.I. improvers may also be derivatized to include other properties or functions, such as the addition of dispersancy properties.

These oil soluble V.I. polymers will generally have number average molecular weights of from $10^3$ to $10^6$, preferably $10^4$ to $10^6$, e.g. 20,000 to 250,000, as determined by gel permeation chromatography or membrane osmometry.

Examples of suitable hydrocarbon polymers include homopolymers and copolymers of two or more monomers of $C_2$ to $C_{30}$, e.g. $C_2$ to $C_8$ olefins, including both alpha-olefins and internal olefins, which may be straight or branched, aliphatic, aromatic, alkyl-aromatic, cycloaliphatic, etc. Frequently they will be of ethylene with $C_3$ to $C_{30}$ olefins, particularly preferred being the copolymers of ethylene and propylene. Other polymers can be used such as polyisobutylenes, homopolymers and copolymers of $C_6$ and higher alpha-olefins, atactic polypropylene, hydrogenated polymers and copolymers and terpolymers of styrene, e.g. with isoprene and/or butadiene.

More specifically, other hydrocarbon polymers suitable as viscosity index improvers in the present invention include those which may be described as hydrogenated or partially hydrogenated homopolymers, and random, tapered, star, or block interpolymers (including terpolymers, tetrapolymers, etc.) of conjugated dienes and/or monovinyl aromatic compounds with, optionally, alpha-olefins or lower alkenes, e.g., $C_3$ to $C_{18}$ alpha-olefins or lower alkenes. The conjugated dienes include isoprene, butadiene, 2,3-dimethylbutadiene, piperylene and/or mixtures thereof, such as isoprene and butadiene. The monovinyl aromatic compounds include vinyl di- or polyaromatic compounds, e.g., vinyl naphthalene, or mixtures of vinyl mono-, di- and/or polyaromatic compounds, but are preferably monovinyl monoaromatic compounds, such as styrene or alkylated styrenes substituted at the alpha-carbon atoms of the styrene, such as alpha-mehtylstyrene, or at ring carbons, such as o-, m-, p-methylstyrene, ethylstyrene, propylstyrene, isopropylstyrene, butylstyrene isobutylstyrene, tert-butylstyrene (e.g., p-tert-butylstyrene). Also included are vinylxylenes, methylethylstyrenes and ethylvinylstyrenes. Alpha-olfins and lower alkenes optionally included in these random, tapered and block copolymers preferably include ethylene, propylene, butene, ethylene-propylene copolymers, isobutylene, and polymers and copolymers thereof. As is also known in the art, these random, tapered and block copolymers may include relatively small amounts, that is less than about 5 mole %, of other copolymerizable monomers such as vinyl pyridines, vinyl lactams, methacrylates, vinyl chloride, vinylidene chloride, vinyl acetate, vinyl stearate, and the like.

Specific examples include random polymers of butadiene and/or isoprene and polymers of isoprene and/or butadiene and styrene. Typical block copolymers include polystyrene-polyisoprene, polystyrene-polybutadiene, polystyrene-polyethylene, polystyrene-ethylene propylene copolymer, polyvinyl cyclohexane-hydrogenated polyisoprene, and polyvinyl cyclohexane-hydrogenated polybutadiene. Tapered polymers include those of the foregoing monomers prepared by methods known in the art. Star-shaped polymers typically comprise a nucleus and polymeric arms linked to said nucleus, the arms being comprised of homopolymer or interpolymer of said conjugated diene and/or monovinyl aromatic monomers. Typically, at least about 80% of the aliphatic unsaturation and about 20% of the aromatic unsaturation of the star-shaped polymer is reduced by hydrogenation.

Representative examples of patents which disclose such hydrogenated polymers or interpolymers include U.S. Pat. Nos. 3,312,621, 3,318,813, 3,630,905, 3,668,125, 3,763,044, 3,795,615, 3,835,053, 3,838,049, 3,965,019, 4,358,565, and 4,557,849, the disclosures of which are herein incorporated by reference.

The polymer may be degraded in molecular weight, for example by mastication, extrusion, oxidation or thermal degradation, and it may be oxidized and contain oxygen. Also included are derivatized polymers such as post-grafted interpolymers of ethylene-propylene with an active monomer such as maleic anhydride which may be further reacted with an alcohol, or amine, e.g. an alkylene polyamine or hydroxy amine, e.g. see U.S. Pat. Nos. 4,089,794, 4,160,739, 4,137,185, or copolymers of ethylene and propylene reacted or grafted with nitrogen compounds such as shown in U.S. Pat. Nos. 4,068,056, 4,068,058, 4,146,489 and 4,149,984.

Suitable hydrocarbon polymers are ethylene copolymers containing from 15 to 90 wt % ethylene, preferably 30 to 80 wt. % of ethylene and 10 to 85 wt. %, preferably 20 to 70 wt. % of one or more $C_3$ to $C_{28}$, preferably $C_3$ to $C_{18}$, more preferably $C_3$ to $C_8$, alpha-olefins. While not essential, such copolymers preferably have a degree of crystallinity of less than 25 wt. %, as determined by X-ray and differential scanning calorimetry. Copolymers of ethylene and propylene are most preferred. Other alpha-olefins suitable in place of propylene to form the copolymer, or to be used in combination with ethylene and propylene, to form a terpolymer, tetrapolymer, etc., include 1-butene, 1-pentene, 1-hexene, 1-heptene, 1-octene, 1-nonene, 1-decene, etc.; also branched chain alpha-olefins, such as 4-methyl-1-pentene, 4-methyl-1-hexene, 5-methylpentene-1, 4,4-dimethyl-1-pentene, and 6-methyl-heptene-1, etc., and mixtures thereof.

Terpolymers, tetrapolymers, etc., of ethylene, said $C_{3-28}$ alpha-olefin, and non-conjugated diolefin or mixtures of such diolefins may also be used. The amount of the non-conjugated diolefin generally ranges from about 0.5 to 20 mole percent, preferably from about 1 to about 7 mole percent, based on the total amount of ethylene and alpha-olefin present.

The preferred V.I. improvers are polyesters, most preferably polyesters of ethylencially unsaturated $C_3$ to $C_8$ mono- and dicarboxylic acids such as methacrylic and acrylic acids, maleic acid, maleic anhydride, fumaric acid, etc.

Examples of unsaturated esters that may be used include those of aliphatic saturated mono alcohols of at least 1 carbon atom and preferably of from 12 to 20 carbon atoms, such as decyl acrylate, lauryl methacrylate, cetyl methacrylate, stearyl methacrylate, and the like and mixtures thereof.

Other esters include the vinyl alcohol esters of $C_2$ to $C_{22}$ fatty or monocarboxylic acids, preferably saturated such as vinyl acetate, vinyl laurate, vinyl palmitate, vinyl stearate, vinyl oleate, and the like and mixtures thereof. Copolymers of vinyl alcohol esters with unsaturated acid esters such as the copolymer of vinyl acetate with dialkyl fumarates, can also be used.

The esters may be copolymerized with still other unsaturated monomers such as olefins, e.g. 0.2 to 5 moles of $C_2$-$C_{20}$ aliphatic or aromatic olefin per mole of unsaturated ester, or per mole of unsaturated acid or anhydride followed by esterification. For example, copolymers of styrene with maleic anhydride esterified r with alcohols and amines are known, e.g. see U.S. Pat. No. 3,702,300.

Such ester polymers may be grafted with, or the ester copolymerized with, polymerizable unsaturated nitrogen-containing monomers to impart dispersancy to the V.I. improvers. Examples of suitable unsaturated nitrogen-containing monomers to impart dispersancy include those containing 4 to 20 carbon atoms such as amino substituted olefins as p-(beta-diethylaminoethyl)styrene; basic nitrogen-containing heterocycles carrying a polymerizable ethylenically unsaturated substituent, e.g. the vinyl pyridines and the vinyl alkyl pyridines such as 2-vinyl-5-ethyl pyridine, 2-methyl-5-vinyl pyridine, 2-vinyl-pyridine, 3-vinyl-pyridine, 4-vinyl-pyridine, 3-methyl-5-vinyl-pyridine, 4-methyl-2-vinyl-pyridine, 4-ethyl-2-vinyl-pyridine, and 2-butyl-5-vinyl-pyridine and the like.

N-vinyl lactams are also suitable, e.g. N-vinyl pyrrolidones or N-vinyl piperidones.

The vinyl pyrrolidones are preferred and are exemplified by N-vinyl pyrrolidone, N-(1-methyl-vinyl) pyrrolidone, N-vinyl-5-methyl pyrrolidone, N-vinyl-3,3-dimethylpyrrolidone, N-vinyl-5-ethyl pyrrolidone, etc.

Corrosion inhibitors, also known as anti-corrosive agents, reduce the degradation of the non-ferrous metallic parts in contact with the fluid. Illustrative of corrosion inhibitors are phosphosulfurized hydrocarbons and the products obtained by reaction of a phosphosulfurized hydrocarbon with an alkaline earth metal oxide or hydroxide, preferably in the presence of an alkylated phenol or of an alkylphenol thioether, and also preferably in the presence of carbon dioxide. As discussed hereinabove, the phosphosulfurized hydrocarbons are prepared by reacting a suitable hydrocarbon such as a terpene, a heavy petroleum fraction of a $C_2$ to $C_6$ olefin polymer such as polyisobutylene, with from 5 to 30 weight percent of a sulfide of phosphorous for ½ to 15 hours, at a temperature in the range of 150° to 400° F. Neutralization of the phosphosulfurized hydrocarbon may be effected in the manner taught in U.S. Pat. 2,969,324.

Other suitable corrosion inhibitors include copper corrosion inhibitors comprising hydrocarbylthio-disubstitutued derivatives of 1, 3, 4-thiadiazole, e.g., $C_2$ to $C_{30}$; alkyl, aryl, cycloalkyl, aralkyl and alkaryl-mono-, di-, tri-, or tetra- or thio-disubstituted derivatives thereof.

Representative examples of such materials included 2,5-bis(octylthio) 1,3,4-thiadiazole; 2,5-bis(octyldithio)-1,3,4-thiadiazole; 2,5-bis(octyltrithio)-1,3,4-thiadiazole; 2,5-bis(octyltetrathio)-1,3,4-thiadiazole; 2,5-bis(nonylthio)-1,3,4-thiadiazole; 2,5-bis(dodecyldithio)-1,3,4-thiadiazole; 2-dodecyldithio-5-phenyldithio-1,3,4-thiadiazole; 2,5-bis(cyclohexyl dithio)-1,3,4-thiadiazole; and mixtures thereof.

Preferred copper corrosion inhibitors are derivatives of 1,3,4-thiadiazoles such as those described in U.S. Pat. Nos. 2,719,125, 2,719,126, and 3,087,932; especially preferred is the compound 2,5-bis(t-octyldithio)-1,3,4-thiadiazole commercially available as Amoco 150, and 2, 5-bis(t-nonyldithio)-1,3,4-thiadiazole, commerically available as Amoco 158.

The preparation of such materials is further described in U.S. Pat. Nos. 2,719,125, 2,719,126, 3,087,932, and 4,410,436, the disclosures of which are hereby incorporated by reference.

Oxidation inhibitors reduce the tendency of mineral oils to deteriorate in service which deterioration is evidenced by the products of oxidation such as sludge and varnish-like deposits on the metal surfaces and by an increase in viscosity. Such oxidation inhibitors include alkaline earth metal salts of alkylphenol thioethers having preferably $C_5$ to $C_{12}$ alkyl side chains, e.g. calcium nonylphenol sulfide, barium t-octylphenol sulfide; aryl amines, e.g. dioctylphenylamine, phenyl-alpha-naphthylamine; phosphosulfurized or sulfurized hydrocarbons, etc.

Friction modifiers serve to impart the proper friction characteristics to an ATF as required by the automotive industry.

Representative examples of suitable friction modifiers are found in U.S. Pat. No. 3,933,659, which discloses fatty acid esters and amides; U.S. Pat. No. 4,176,074, which describes molybdenum complexes of polyisobutenyl succinic anhydride-amino aklanols; U.S. Pat. No. 4,105,571, which discloses glycerol esters of dimerized fatty acids; U.S. Pat. No. 3,779,928, which discloses alkane phosphonic acid salts; U.S. Pat. No. 3,778,928, which discloses alkane phosphonic acid salts; U.S. Pat. No. 3,778,375, which discloses reaction products of a phosphonate with an oleamide; U.S. Pat. No. 3,852,205, which discloses S-carboxy-alkylene hydrocarbyl succinamic acid and mixtures thereof; U.S. Pat. No. 3,879,306, which discloses N-(hydroxyalkyl)alkenyl succinamic acids or succinimides; U.S. Pat. No. 3,932,290, which discloses reaction products of di-(lower alkyl) phosphites and epoxides; and U.S. Pat. No. 4,028,258, which discloses the alkylene oxide adduct of phosphosulfurized N-(hydroxyalkyl) alkenyl succinimides; all for use as friction modifiers in automatic transmission fluids. The disclosures of the above patents are herein incorporated by reference. Among the more preferred friction modifiers is a class of succinate esters or metal salts thereof as described in U.S.

Pat. Nos. 4,664,826 and 4,702,085, the disclosures of which are incorporated herein by reference.

Other preferred friction modifiers which may be used in combination with the phosphorous- and sulfur-containing anti-wear additives of this invention include the hydroxyl amine compounds characterized by one of the following formulas:

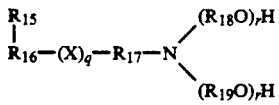

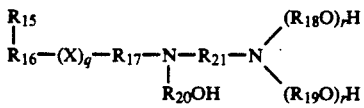

wherein $R_{15}$ represents H or $CH_3$, $R_{16}$ represents a $C_3$ to $C_{27}$, preferably $C_8$ to $C_{22}$, and most preferably $C_{10}$ to $C_{20}$ saturated or unsaturated aliphatic hydrocarbyl radical; $R_{17}$ and $R_{20}$ independently, represent the same or different straight or branched chain $C_1$ to $C_6$, preferably $C_2$ to $C_4$, alkylene radical; $R_{18}$ and $R_{19}$, independently, represent the same or different straight or branched chain $C_1$ to $C_5$, preferably $C_2$ to $C_4$ alkylene radical; $R_{21}$ represents a straight or branched chain $C_1$ to $C_5$, preferably $C_2$ to $C_3$, alkylene radical; X represents O or S; p represents 0 or 1; and q, independently, represents the same or different number of from about 1 to about 4, preferably 1 to 2. In a particularly preferred embodiment, the hydroxyl amine friction modifier would be characterized by the formula XI wherein X represents O, $R_{15}$ and $R_{16}$ contain a combined total of 18 carbon atoms, $R_{17}$ represents $C_3$ alkylene, $R_{18}$ and $R_{19}$ represent $C_2$ alkylene, q is 1, and each r is 1. It is preferred that the hydroxyl amine compounds contain a combined total of from about 18 to about 30 carbon atoms.

When the hydroxyl amine compounds are characterized by the formula XII and when X is O and q is 1, the hydroxyl amine compounds can be prepared, for example, by a multi-step process wherein an alkanol is first reacted, in the presence of a catalyst, with an unsaturated nitrile such as acrylonitrile to form an ether nitrile intermediate. The intermediate is then hydrogenated, preferably in the presence of a conventional hydrogenation catalyst such as platinum black or Raney nickel to form an ether amine. The ether amine is then reacted with an alkylene oxide, such as ethylene oxide in the presence of an alkaline catalyst by a conventional method at a temperature in the range of about 90°–150° C. The overall process for preparing the desired hydroxyl amine compounds can be illustrated by the following equations:

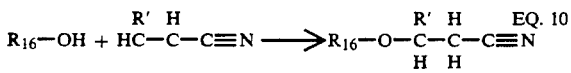

EQ. 10

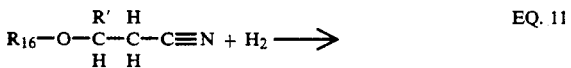

EQ. 11

EQ. 12

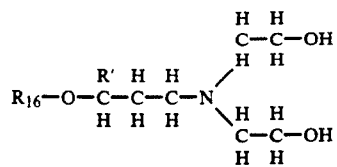

where $R_{16}$ represents straight or branched chain alkyl as described above and R' represents hydrogen or a $C_1$ to $C_3$ alkyl branch of the alkylene radical constituting $R_{17}$ in formula XI.

Another method of preparing the present hydroxyl amine compounds, when X is O and q is 1, is by reacting a fatty acid with ammonia or an alkanol amine, such as ethanolamine, to form an intermediate which can be further oxyalkylated by reaction with an alkylene oxide, such as ethylene oxide or propylene oxide. A process of this type is discussed, for example, in U.S. Pat. No. 4,201,684, the disclosure of which is incorporated herein by reference.

When X is S and q is 1, the hydroxyl amine friction modifying compounds can be formed, for example, by effecting a conventional free radical reaction between a long chain alpha-olefin with a hydroxyalkyl mercaptan, such as beta-hydroxyethyl mercaptan, to produce a long chain alkyl hydroxyalkyl sulfide. The long chain alkyl hydroxyalkyl sulfide is then mixed with thionyl chloride at a low temperature and thereafter heated to about 40° C. to form a long chain alkyl chloroalkyl sulfide. The long chain alkyl chloroalkyl sulfide is then caused to react with a dialkanolamine, such as diethanolamine, and, if desired, with an alkylene oxide, such as ethylene oxide, in the presence of an alkaline catalyst and at a temperature on the order of about 100° C. to form the desired hydroxyl amine compounds. Processes of the above type are known in the art and are discussed, for example, in U.S. Pat. No. 3,705,139, the disclosure of which is incorporated herein by reference.

In cases when q is 0, the present hydroxyl amine friction modifiers are well known in the art and are described, for example, in U.S. Pat. Nos. 3,186,946, 4,170,560, 4,231,883, 4,409,000 and 3,711,406, the disclosures of these patents being incorporated herein by reference. Such hydroxyl amine compounds are available commercially, from the Armak Chemical Division of Akzo Chemie, for example, under the trade names Ethomeen, Ethomeen T/12, Ethomeen C/15, Ethoduomeen T/12, Ethoduomeen T/15, etc.

Examples of suitable hydroxyl amine compounds include but are not limited to the following N,N-bis(2-hydroxyethyl)-n-dodecylamine
N,N-bis(2-hydroxyethyl)-1-methyl-tridecenylamine
N,N-bis(2-hydroxyethyl)-hexadecylamine
N,N-bis(2-hydroxyethyl)-octadecylamine
N,N-bis(2-hydroxyethyl)-octadecenylamine
N,N-bis(2-hydroxyethyl)-oleylamine
N,N-bis(2-hydroxyethyl)-stearylamine
N,N-bis(2-hydroxyethyl)-undecylamine
N-(2-hydroxyethyl)-N-(hydroxyethoxyethyl)-n-dodecylamine
N,N-bis(2-hydroxyethyl)-1-methyl-undecylamine
N,N-bis(2-hydroxyethoxyethoxyehtyl)-1-ethyloctadecylamine
N,N-bis(2-hydroxyethyl)-cocoamine N,N-bis(2-hydroxyethyl)-tallowamine
N,N-bis(2-hydroxyethyl)-n-dodecyloxyethylamine
N,N-bis(2-hydroxyethyl)-lauryloxyethylamine
N,N-bis(2-hydroxyethyl)-stearyloxyethylamine
N,N-bis(2-hydroxyethyl)-n-dodecyloxypropylamine
N,N-bis(2-hydroxyethyl)-stearyloxypropylamine
N,N-bis(2-hydroxyethyl)-dodecylthioethylamine
N,N-bis(2-hydroxyethyl)-dodecylthiopropylamine
N,N-bis(2-hydroxyethyl)-hexadecylthioethylamine
N,N-bis(2-hydroxyethyl)-hexadecylthiopropylamine
N-2-hydroxyethyl,N-[N',N'-bis(2-hydroxyethyl) ethylamine]-octadecylamine
N-2-hydroxyethyl,N-[N',N'-bis(2-hydroxyethyl) ethylamine]-stearylamine The hydroxyl amine compounds may be used as such. However they may also be used in the form of an adduct or reaction product with a boron compound, such as a boric oxide, a boron halide, a metaborate, boric acid, or a mono-, di-, or triorgano borate, such as a mono-, di-, and trialkyl borate. Such adducts or derivatives may be illustrated with reference to formula XI, for example, by the following structural formula

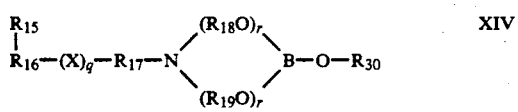

XIV wherein $R_{15}$, $R_{16}$, $R_{17}$, $R_{18}$, $R_{19}$, X, q, and r are the same as defined above, and wherein $R_{30}$ is either H or a hydrocarbyl, e.g., alkyl radical.

Representative examples of alkyl borates which may be used to borate the alkanol amine compounds include mono-, di-, and tributyl borates, mono-, di-, and trihexyl borates, and the like. The borated adducts may be prepared simply by heating a mixture of the hydroxyl amine compound and the boron compound, preferably in the presence of a suitable solvent or solvents, preferably an alcoholic or hydrocarbon solvent. The presence of a solvent is not essential, however, if one is used it may be reactive or non-reactive. Suitable non-reactive solvents include benzene, toluene, xylene and the like. Suitable reactive solvents include isopropanol, butanol, the pentanols and the like. Reaction temperatures suitably may be on the order of about 100° to about 280° C., preferably from about 125° to 175° C. Reaction time is not critical and, depending on the temperature, etc., it may vary from about 1-2 hours up to about 15 hours, e.g., 2 to 6 hours until the desired amount of water is removed. Suitable boration procedures and materials contemplated within the scope of $R_{20}$ are well known in the art and are described, for example, in U.S. Pat. Nos. 4,382,006, 4,400,284, 4,529,528, 4,594,171, and 4,595,514, the disclosures of which are incorporated herein by reference.

Dispersants maintain oil insolubles, resulting from oxidation during use, in suspension in the fluid thus preventing sludge flocculation and precipitation. Suitable dispersants include, for example, dispersants of the ash-producing or ashless type, the latter type being preferred.

The ash-producing detergents are exemplified by oil-soluble neutral and basic salts of alkali or alkaline earth metals with sulfonic acids, carboyxlic acids, or organic phosphorus acids characterized by at least one direct carbon-to-phosphorus linkage such as those prepared by the treatment of an olefin polymer (e.g. polyisobutene having a molecular weight of 1,000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichimetrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature of about 50° C. and filtering the resulting mass. The use of a "promoter" in the neutralization step t aid the incorporation of a large excess of metal likewise is know. Examples of compounds useful as the promoter include phenolic substance such as phenol, naphthol, alkylphenol, thiophenol, sulfurized alkylphenol, and condensation products of formaldehyde with a phenolic substance; alcohols such as methanol, 2-propanol, octyl alcohol, cellosolve, ethylene glycol, stearyl alcohol, and cyclohexyl alcohol; and amines such as aniline, phenylenediamine, phenyl-beta-naphthylamine, and dodecylamine. A particularly effective method for preparing the basic salts comprises mixing an acid with an excess of a basic alkaline earth metal neutralizing agent and a least one alcohol promoter, and carbonating the mixture at an elevated temperature such as 60°-200° C. This class of materials is discussed further hereinabove in connection with detergents and metal rust inhibitors.

The most preferred ash-producing detergents include the metal salts of sulfonic acids, alkyl phenols, sulfurized alkyl phenols, alkyl salicylates, naphthenates and other oil soluble mono- and dicarboxylic acids. Highly basic (viz, overbased) metal salts, such as highly basic alkaline earth metal sulfonates (especially Ca and Mg salts) are frequently used as detergents. They are usually produced by heating a mixture comprising an oil-soluble sulfonate or alkaryl sulfonic acid, with an excess of alkaline earth metal compound above that required for complete neutralization of any sulfonic acid present, and thereafter forming a dispersed carbonate complex by reacting the excess metal with carbon dioxide to provide the desired overbasing. The sulfonic acids are typically obtained by the sulfonation of alkyl substituted aromatic hydrocarbons such as those obtained from the fractionation of petroleum by distillation and/or extraction or by the alkylation of aromatic hydrocarbons as for example those obtained by alkylating benzene, toluene, xylene, naphthalene, diphenyl and the halogen derivatives such as chlorobenzene, chlorotoluene and chloronaphthalene. The alkylation may be carried out in the presence of a catalyst with alkylating agents having from about 3 to more than 30 carbon atoms such as for example haloparaffins, olefins that may be obtained by dehydrogenation of paraffins, polyolefins as for example polymers from ethylene, propylene, etc. The alkaryl sulfonates usually contain from about 9 to about 70 more carbon atoms, preferably from about 16 to about 50 carbon atoms per alkyl substituted aromatic moiety.

The alkaline earth metal compounds which may be used in neutralizing these alkaryl sulfonic acids to provide the sulfonates includes the oxides and hydroxides, alkoxides, carbonates, carboxylate, sulfide, hydrosulfide, nitrate, borates and ethers of magnesium, calcium, and barium. Examples are calcium oxide, calcium hydroxide, magnesium acetate and magnesium borate. As noted, the alkaline earth metal compound is used in excess of that required to complete neutralization of the alkaryl sulfonic acids. Generally, the amount ranges from about 100 to about 220%, although it is preferred to use at least 125%, of the stoichiometric amount of metal required for complete neutralization.

Various other preparations of basic alkaline earth metal alkaryl sulfonates are known, such as those described in U.S. Pat. Nos. 3,150,088 and 3,150,089, wherein overbasing is accomplished by hydrolysis of an alkoxide-carbonate complex with the alkaryl sulfonate in a hydrocarbon solvent/diluent oil.

Ashless dispersants, which are the preferred dispersant for use in connection with this invention, are so called despite the fact that, depending on their constitution, the dispersant may upon combusiton yield a non-volatile material such as boric oxide or phosphorus pentoxide; however, they ordinarily do not contain metal and therefore do not yield a metal-containing ash on combustion. Many types of ashless dispersants are known in the art, and any of them are suitable for use in the lubricant compositions of this invention. The following are illustrative:

1. Reaction products of carboxylic acids (or derivatives thereof) containing at least about 30 and preferably at least about 50 carbon atoms with nitrogen containing compounds such as amine, organic hydroxy compounds such as phenols and alcohols, and/or basic inorganic materials. Examples of these "carboxylic dispersants" are described, for example, in British Patent No. 1,306,529 and in U.S. Pat. Nos. 3,272,746, 3,341,542, 3,454,607 and 4,654,403.

More, specifically, nitrogen- or ester-containing ashless dispersants comprise members selected from the group consisting of oil soluble salts, amides, imides, oxazolines and esters, or mixtures thereof, of long chain hydrocarbyl-substituted mono- and dicarboxylic acids or anhydride or ester derivatives thereof wherein said long chain hydrocarbyl group is a polymer, typically of a $C_2$ to $C_{10}$, e.g., $C_2$ to $C_5$, monoolefin, said polymer having a number average molecular weight of from about 700 to 5000.

The long chain hydrocarbyl-substituted dicarboxylic acid material which can be used to make the dispersant includes the reaction product of long chain hydrocarbon polymer, generally a polyolefin, with (i) monounsaturated $C_4$ to $C_{10}$ dicarboxylic acid wherein (a) the carboxyl groups are vicinyl, (i.e. located on adjacent carbon atoms) and (b) at least one, preferably both, of said adjacent carbon atoms are part of said mono unsaturation; or with (ii) derivatives of (i) such as anhydrides or $C_1$ to $C_5$ alcohol derived mono- or diesters of (i). Upon reaction with the hydrocarbon polymer, the monounsaturation of the dicarboxylic acid material becomes saturated. Thus, for example, maleic anhydride becomes a hydrocarbyl-substituted succinic anhydride.

Typically, from about 0.7 to about 4.0 (e.g., 0.8 to 2.6), preferably from about 1.0 to about 2.0, and most preferably from about 1.1 to about 1.7 moles of said unsaturated $C_4$ to $C_{10}$ dicarboxylic acid material are charged to the reactor per mole of polyolefin charged.

Normally, not all of the polyolefin reacts with the unsaturated acid or derivative and the hydrocarbyl-substituted dicarboxylic acid material will contain unreacted polyolefin. The unreacted polyolefin is typically not removed from the reaction mixture (because such removal is difficult and would be commercially infeasible) and the product mixture, stripped of any unreacted monounsaturated $C_4$ to $C_{10}$ dicarboxylic acid material, is employed for further reaction with the amine or alcohol as described hereinafter to make the dispersant.

Characterization of the average number of moles of dicarboxylic acid, anydride or ester which have reacted per mole of polyolefin charged to the reaction (whether it has undergone reaction or not) is defined herein as functionality. Said functionality is based upon (i) determination of the saponification number of the resulting product mixture using potassium hydroxide; and (ii) the number average molecular weight of the polymer charged using techniques well known in the art. Functionality is defined solely with reference to the resulting product mixture. Consequently, although the amount of said reacted polyolefin contained in the resulting product mixture can be subsequently modified, i.e., increased or decreased by techniques known in the art, such modifications do not alter functionality as defined above. The term hydrocarbyl-substituted dicarboxylic acid material is intended to refer to the product mixture whether it has undergone such modification or not.

Accordingly, the functionality of the hydrocarbyl-substituted dicarboxylic acid material will be typically at least about 0.5, preferably at least about 0.8, and most preferably at least about 0.9, and can vary typically from about 0.5 to about 2.8 (e.g., 0.6 to 2), preferably from about 0.8 to about 1.4, and most preferably from about 0.9 to about 1.3.

Exemplary of such unsaturated mono and dicarboxylic acids, or anhydrides and esters thereof are fumaric acid, itaconic acid, maleic acid, maleic anhydride, chloromaleic acid, chloromaleic anhydride, acrylic acid, methacrylic acid, crotonic acid, cinnamic acid, etc.

Preferred olefin polymers for reaction with the unsaturated dicarboxylic acids or derivatives thereof are polymers comprising a major molar amount of $C_2$ to $C_{10}$, e.g. $C_2$ to $C_5$ monoolefin. Such olefins include ethylene, propylene, butylene, isobutylene, pentene, octene-1, styrene, etc. The polymers can be homopolymers such as polyisobutylene, as well as copolymers of two or more of such olefins such as copolymers of: ethylene and propylene; butylene and isobutylene; propylene and isobutylene; etc. Other copolymers include those in which a minor molar amount of the copolymer monomers, e.g., 1 to 10 mole %, is a $C_4$ to $C_{18}$ non-conjugated diolefin, e.g., a copolymer of isobutylene and butadiene: or a copolymer of ethylene, propylene and 1,4-hexadiene; etc.

In some cases, the olefin polymer may be completely saturated, for example an ethylene-propylene copolymer made by a Ziegler-Natta synthesis using hydrogen as a moderator to control molecular weight.

The olefin polymers used in the dispersants will usually have number average molecular weights within the range of about 700 and about 5,000, more usually between about 800 and about 3000. Particularly useful olefin polymers have number average molecular weights within the range of about 900 and about 2500 with approximately one terminal double bond per polymer chain. An especially useful starting material for highly potent dispersant additives is polyisobutylene. The number average molecular weight for such polymers can be determined by several known techniques.

A convenient method for such determination is by ge permeation chromatography (GPC) which additionally provides molecular weight distribution information, see W. W. Yau, J. J. Kirkland and D. D. Bly, "Modern Size Exclusion Liquid Chromatography", John Wiley and Sons, New York, 1979.

Processes for reacting the olefin polymer with the $C_{4-10}$ unsaturated dicarboxylic acid, anhydride or ester are known in the art. For example, the olefin polymer and the dicarboxylic acid or derivative may be simply heated together as disclosed in U.S. Pat. Nos. 3,361,673 and 3,401,118 to cause a thermal "ene" reaction to take place. Or, the olefin polymer can be first halogenated, for example, chlorinated or brominated to about 1 to 8 wt. %, preferably 3 to 7 wt. % chlorine, or bromine, based on the weight of polymer, by passing the chlorine or bromine through the polyolefin at a temperature of 60° to 250° C., e.g. 120° to 160° C., for about 0.5 to 10, preferably 1 to 7 hours. The halogenated polymer may then be reacted with sufficient unsaturated acid or derivative at 100° to 250° C., usually about 180° to 235° C., for about 0.5 to 10, e.g. 3 to 8 hours, so the product obtained will contain the desired number of moles of the unsaturated acid or derivative per mole of the halogenated polymer. Processes of this general type are taught in U.S. Pat. Nos. 3,087,936, 3,172,892, 3,272,746 and others.

Alternatively, the olefin polymer, and the unsaturated acid or derivative are mixed and heated while adding chlorine to the hot material. Processes of this type are disclosed in U.S. Pat. Nos. 3,215,707, 3,231,587, 3,912,764, 4,110,349, and in U.K. 1,440,219.

By the use of halogen, about 65 to 95 wt. % of the polyolefin, e.g. polyisobutylene will normally react with the dicarboxylic acid or derivative. Upon carrying out a thermal reaction without the use of halogen or a catalyst, then usually only about 50 to 75 wt. % of the polyisobutylene will react. Chlorination helps increase the reactivity.

At least one hydrocarbyl-substituted dicarboxylic acid material is mixed with at least one of amine, alcohol, including polyol, aminoalcohol, etc., to form the dispersant additives. When the acid material is further reacted, e.g., neutralized, then generally a major proportion of at least 50 percent of the acid producing units up to all the acid units will be reacted.

Amine compounds useful as nucleophilic reactants for neutralization of the hydrocarbyl-substituted dicarboxylic acid materials include mono- and (preferably) polyamines, most preferably polyalkylene polyamines, of about 2 to 60, preferably 2 to 40 (e.g. 3 to 20), total carbon atoms and about 1 to 12, preferably 3 to 12, and most preferably 3 to 9 nitrogen atoms in the molecule. These amines may be hydrocarbyl amines or may be hydrocarbyl amines including other groups, e.g, hydroxy groups, alkoxy groups, amide groups, nitriles, imidazoline groups, and the like. Hydroxyl amines with 1 to 6 hydroxy groups, preferably 1 to 3 hydroxy groups are particularly useful. Preferred amines are aliphatic saturated amines, including those of the general formulas:

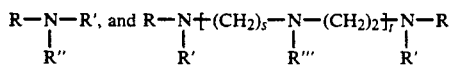

XV    XVI wherein R, R', R" and R''' are independently selected from the group consisting of hydrogen; $C_1$ to $C_{25}$ straight or branched chain alkyl radicals; $C_1$ to $C_{12}$ alkoxy $C_2$ to $C_6$ alkylene radicals; $C_2$ to $C_{12}$ hydroxy amino alkylene radicals; and $C_1$ to $C_{12}$ alkylamino $C_2$ to $C_6$ alkylene radicals; and wherein R''' can additionally comprise a moiety of the formula:

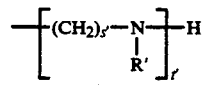

XVII wherein R' is as defined above, and wherein s and s' can be the same or a different number of from 2 to 6, preferably 2 to 4; and t and t' can be the same or different and are numbers of from 0 to 10, preferably 2 to 7, and most preferably about 3 to 7, with the proviso that the sum of t and t' is not greater than 15. To assure a facile reaction, it is preferred that R, R', R", R''' s, s', t and t' be selected in a manner sufficient to provide the compounds of formulas XV and XVI with typically at least one primary or secondary amine group, preferably at least two primary or secondary amine groups. This can be achieved by selecting at least one of said R, R', R" or R''' groups to be hydrogen or by letting t in formula XVI be at least one when R''' is H or when the XVII moiety possesses a secondary amino group. The most preferred amine of the above formulas are represented by formula XVI and contain at least two primary amine groups and at least one, and preferably at least three, secondary amine groups.

Non-limiting examples of suitable amine compounds include: 1,2-diaminoethane; 1,3-diaminopropane; 1,4-diaminobutane; 1,6-diaminohexane; polyethylene amines such as diethylene triamine; triethylene tetramine; tetraethylene pentamine; polypropylene amines such as 1,2- propylene diamine; di-(1,2-propylene)triamine; di-(1,3- propylene) triamine; N,N-dimethyl-1,3-diaminopropane; N,N- di-(2-aminoethyl) ethylene diamine; N,N-di(2-hydroxyethyl)-1,3-propylene diamine; 3-dodecyloxypropylamine; N-dodecyl- 1,3-propane diamine; trishydroxymethylaminomethane (THAM); diisopropanol amine; diethanol amine; triethanol amine; mono-, di-, and tri-tallow amines; amino morpholines such as N-(3-aminopropyl)morpholine; and mixtures thereof.

Other useful amine compounds include: alicyclic diamines such as 1,4-di(aminomethyl) cyclohexane, and heterocyclic nitrogen compounds such as imidazolines, and N-aminoalkyl piperazines of the general formula XVIII:

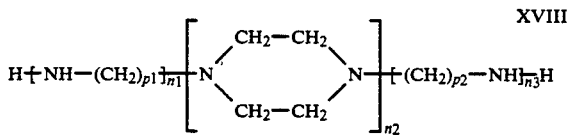

XVIII wherein p1 and p2 are the same or different and are same or different and are each integers of from 1 to 3. Non-limiting examples of such amines include 2-pentadecyl imidazoline; N-(2-aminoethyl) piperazine; etc. Commercial mixtures of amine compounds may advantageously be used. For example, one process for preparing alkylene amines involves the reaction of an alkylene dihalide (such as ethylene dichloride or propylene dichloride) with ammonia, which results in a complex mixture of alkylene amines wherein pairs of nitrogens are joined by alkylene groups, forming such compounds as diethylene triamine, triethylenetetramine, tetraethylene pentamine and isomeric piperazines. Low cost poly(ethyleneamines) compounds averaging about 5 to 7 nitrogen atoms per molecule are available commercially under trade names such as "Polyamine H", "Polyamine 400", "Dow Polyamine E-300", etc.

Useful amines also include polyoxyalkylene polyamines such as those of the formulas:

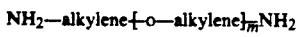   XIX where m has a value of about 3 to 70 and preferably 10 to 35; and

   XX where "n" has a value of about 1 to 40 with the provision that the sum of all the n's is from about 3 to about 70 and preferably from about 6 to about 35, and R is a polyvalent saturated hydrocarbon radical of up to ten carbon atoms wherein the number of substituents on the R group is represented by the value of "a", which is a number of from 3 to 6. The alkylene groups in either formula XIX or XX may be straight or branched chains containing about 2 to 7, and preferably about 2 to 4 carbon atoms.

The polyoxyalkylene polyamines of formulas XIX or XX above, preferably polyoxyalkylene diamines and polyoxyalkylene triamines, may have average molecular weights ranging from about 200 to about 4000, and preferably from about 400 to about 2000. The preferred polyoxyalkylene polyamines include the polyoxyethylene and polyoxypropylene diamines and the polyoxypropylene triamines having average molecular weights ranging from about 200 to 2000. The polyoxyalkylene polyamines are commercially available and may be obtained, for example, from the Jefferson Chemical Company, Inc. under the trade name "Jeffamines D-230, D-400, D-1000, D- 2000, T-403", etc.

The amine is readily reacted with the selected hydrocarbyl-substituted dicarboxylic acid material, e.g. alkenyl succinic anhydride, by heating an oil solution containing 5 to 95 wt. % of said hydrocarbyl-substituted dicarboxylic acid material to about 100° to 250° C., preferably 125° to 175° C., generally for 1 to 10, e.g. 2 to 6 hours until the desired amount of water is removed. The heating is preferably carried out to favor formation of imides or mixtures of imides and amides, rather than amides and salts. Reaction ratios of hydrocarbyl-substituted dicarboxylic acid material to equivalents of amine as well as the other nucleophilic reactants described herein can vary considerably, depending on the reactants and type of bonds formed. Generally from 0.1 to 1.0, preferably from about 0.2 to 0.6, e.g., 0.4 to 0.6, equivalents of dicarboxylic acid unit content (e.g., substituted succinic anhydride content) is used per reactive equivalent of nucleophilic reactant, e.g., amine. For example, about 0.8 mole of a pentamine (having two primary amino groups and five reactive equivalents of nitrogen per molecule) is preferably used to convert into a mixture of amides and imides, a composition, having a functionality of 1.6, derived from reaction of polyolefin and maleic anhydride; i.e., preferably the pentamine is used in an amount sufficient to provide about 0.4 equivalents (that is, 1.6 divided by (0.8×5) equivalents) of succinic anhydride units per reactive nitrogen equivalent of the amine.

The ashless dispersant esters are derived from reaction of the aforesaid long chain hydrocarbyl-substituted dicarboxylic acid material and hydroxy compounds such as monohydric and polyhydric alcohols or aromatic compounds such as phenols and naphthols, etc. The polyhydric alcohols are the most preferred hydroxy compound and preferably contain from 2 to about 10 hydroxy radicals, for example, ethylene glycol, diethylene glycol, triethylene glycol, tetraethylene glycol, dipropylene glycol, and other alkylene glycols in which the alkylene radical contains from 2 to about 8 carbon atoms. Other useful polyhydric alcohols include glycerol, monooleate of glycerol, monostearate of glycerol, monomethyl ether of glycerol, pentaerythritol, dipentaerythritol, and mixtures thereof.

The ester dispersant may also be derived from unsaturated alcohols such as allyl alcohol, cinnamyl alcohol, propargyl alcohol, 1-cyclohexane-3-ol, and oleyl alcohol. Still other classes of the alcohols capable of yielding the ester of this invention comprise the ether alcohols and amino alcohols including, for example, the oxyalkylene-, oxyarylene-, aminoalkylene-, and aminoarylene-substituted alcohols having one or more oxyalkylene, oxyarylene, aminoalkylene or aminoarylene radicals. They are exemplified by Cellosolve, Carbitol, N,N,N',N'-tetrahydroxy-trimethylene diamine, and ether alcohols having up to about 150 oxyalkylene radicals in which the alkylene radical contains from 1 to about 8 carbon atoms.

The ester dispersant may be diesters of succinic acids or acidic esters, i.e., partially esterified succinic acids; as well as partially esterified polyhydric alcohols or phenols, i.e., esters having free alcohols or phenolic hydroxyl radicals. Mixtures of the above illustrated esters likewise are contemplated within the scope of this invention.

The ester dispersant may be prepared by one of several known methods as illustrated for example in U.S. Pat. Nos. 3,381,022 and 3,836,471.

Hydroxy amines which can be reacted with the aforesaid long chain hydrocarbyl-substituted dicarboxylic acid materials to form dispersants include 2-amino-1-butanol, 2-amino-2-methyl-1-propanol, p-(beta-hydroxyethyl)-aniline, 2-amino-1-propanol, 3-amino-1-propanol, 2-amino-2-methyl-1,3-propanediol, 2-amino-2-ethyl-1,3-propanediol, N-(beta-hydroxypropyl)-N'-(beta-aminoethyl)-piperazine, tris(hydroxymethyl) aminomethane (also known as trismethylolaminomethane), 2-amino-1-butanol, ethanolamine, beta-(beta-hydroxyethoxy)ethylamine, and the like. Mixtures of these or similar amines can also be employed. The above description of nucleophilic reactants suitable for reaction with the hydrocarbyl-substituted dicarboxylic acid material includes amines, alcohols, and compounds of mixed amine and hydroxy containing reactive functional groups, i.e., amino-alcohols.

A preferred group of ashless dispersants are those derived from polyisobutylene substituted with succinic anhydride groups and reacted with said polyethylene amines, e.g. tetraethylene pentamine, pentaethylene hexamine, polyoxyethylene and polyoxypropylene amines, e.g. polyoxypropylene diamine, trismethylolaminomethane, or said above-described alcohols such as pentaerythritol, and combinations thereof. One class of particularly preferred dispersants includes those derived from polyisobutene substituted with succinic anhydride groups and reacted with (i) a hydroxy compound, e.g. pentaerythritol, (ii) a polyoxyalkylene polyamine, e.g. polyoxypropylene diamine, and/or (iii) a polyalkylene polyamine, e.g. polyethylene diamine or tetraethylene pentamine. Another preferred dispersant class includes those derived from polyisobutenyl succinic anhydride reacted with (i) a polyalkylene polyamine, e.g. tetraethylene pentamine, and/or (ii) a polyhydric alcohol or polyhydroxy-substituted aliphatic primary amine, e.g. pentaerythritol or trismethylolaminomethane.

2. Reaction products of relatively high molecular weight aliphatic or alicyclic halides with amines, preferably polyalkylene polyamines. These may be characterized as "amine dispersants" and examples thereof are described for example, in the U.S. Pat. Nos. 3,275,554, 3,454,555 and 3,565,804.

3. Reaction products of alkyl phenols in which the alkyl group contains at least about 30 carbon atoms with aldehydes (especially formaldehyde) and amines (especially polyalkylene polyamines), which may be characterized as "Mannich dispersants." The materials described in the following U.S. Patents are illustrative:
   U.S. Pat. No. 3,725,277
   U.S. Pat. No. 3,725,480
   U.S. Pat. No. 3,726,882
   U.S. Pat. No. 3,980,569

4. Products obtained by post-treating the carboxylic, amine or Mannich dispersants with such reagents as urea, thiourea, carbon disulfide, phosphosulfurized hydrocarbons, aldehydes, ketones, carboxylic acids, hydrocarbon-substituted succinic anhydrides, nitriles, epoxides, boron compounds, phosphorus compounds or the like. Exemplary materials of this type are described in the following U.S. Patents:
   U.S. Pat. No. 2,805,217
   U.S. Pat. No. 3,087,936
   U.S. Pat. No. 3,254,025
   U.S. Pat. No. 3,394,179
   U.S. Pat. No. 3,511,780
   U.S. Pat. No. 3,703,536
   U.S. Pat. No. 3,704,308
   U.S. Pat. No. 3,708,422
   U.S. Pat. No. 3,850,822
   U.S. Pat. No. 4,113,639
   U.S. Pat. No. 4,116,876

More specifically, the nitrogen and ester containing dispersants preferably are further treated by boration as generally taught in U.S. Pat. Nos. 3,087,936 and 3,254,025 (incorporated herein by reference). This is readily accomplished by treating the selected nitrogen dispersant with a boron compound selected from the class consisting of boron oxide, boron halides, boron acids and esters of boron acids in an amount to provide from about 0.1 atomic proportion of boron for each mole of said nitrogen dispersant to about 20 atomic proportions of boron for each atomic proportion of nitrogen of said nitrogen dispersant. Usefully borated dispersants contain from about 0.05 to 2.0 wt. %, e.g. 0.05 to 0.7 wt. % boron based on the total weight of said borated nitrogen dispersant. The boron, which appears to be in the product as dehydrated boric acid polymers (primarily $(HBO_2)_3$), is believed to attach to the dispersant imides and diimides as amine salts, e.g., the metaborate salt of said diimide. Treating is readily carried out by adding from about 0.05 to 4, e.g. 1 to 3 wt. % (based on the weight of said nitrogen dispersant) of said boron compound, preferably boric acid which is most usually added as a slurry to said nitrogen dispersant and heating with stirring at from about 135° to 190° C., e.g. 140°–170° C., for from 1 to 5 hours followed by nitrogen stripping at said temperature ranges. Or, the boron treatment can be carried out by adding boric acid to the hot reaction mixture of the dicarboxylic acid material and amine while removing water.

5. Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Patents:
   U.S. Pat. No. 3,329,658
   U.S. Pat. No. 3,519,565
   U.S. Pat. No. 3,666,730
   U.S. Pat. No. 3,702,300

All of the above-noted patents are incorporated by reference herein for their disclosures of ashless dispersants.

In using the phosphorous-acid sulfur-containing product mixture in a power transmitting fluid which contains a dispersant, it is preferred to pre-mix said product mixture with the dispersant, which dispersant typically contains a major proportion of diluent oil, and to heat the resulting mixture at a temperature of typically from about 120° to about 160° F., and preferably from about 140° to about 150° F. for a period of typically from about 0.5 to about 1.5, preferably 0.75 to about 1.2 hours.

Lubricating oil flow improvers (LOFI) include all those additives which modify the size, number, and growth of wax crystals in lube oils in such a way as to impart improved low temperature handling, pumpability, and/or vehicle operability as measured by such tests as pour point and mini rotary viscometry (MRV). The majority of lubricating oil flow improvers are polymers or contain polymers. These polymers are generally of two types, either backbone or sidechain.

The backbone variety, such as the ethylene-vinyl acetates (EVA), have various lengths of methylene segments randomly distrubuted in the backbone of the polymer, which associate or cocrystallize with the wax crystals inhibiting further crystal growth due to branches and non-crystalizable segments in the polymer.

The sidechain type polymers, which are the predominant variety used as LOFI's, have methylene segments as the side chains, preferably as straight side chains. These polymers work similarly to the backbone type except the side chains have been found more effective in treating isoparaffins as well as n-paraffins found in lube oils. Representative of this type of polymer are $C_8$–$C_{18}$ dialkylfumarate/vinyl acetate copolymers, polyacrylates, polymethacrylates, and esterified styrene-maleic anhydride copolymers.

Foam control can be provided by an anti-foamant of the polysiloxane type, e.g. silicone oil and polydimethyl siloxane.

Anti-wear agents, as their name implies, reduce wear of moving metallic parts. Representative of conventional anti-wear agents which may be used to supplement the present phosphorous- and sulfur-containing reaction product mixture are the zinc dialkyl dithiophosphates, and the zinc diaryl dithiophosphates. However, it is an important advantage of the present invention that supplemental anti-wear agents do not have to be employed and, in fact, can be excluded from the compositions of this invention.

Seal swellants include mineral oils of the type that provoke swelling, including aliphatic alcohols of 8 to 13 carbon atoms such as tridecyl alcohol, with a preferred seal swellant being characterized as an oil-soluble, saturated, aliphatic or aromatic hydrocarbon ester of from 10 to 60 carbon atoms and 2 to 4 linkages, e.g. dihexyl phthalate, as are described in U.S. Pat. No. 3,974,081.

Some of these numerous additives can provide a multiplicity of effects e.g. a dispersant oxidation inhibitor. This approach is well known and need not be further elaborated herein.

Compositions, when containing these additives, typically are blended into the base oil in amounts which are effective to provide their normal attendant function. Representative effective amounts of such additives are illustrated as follows:

| Compositions | (Broad) Wt % | (Preferred) Wt % |
|---|---|---|
| V.I. Improver | 1-12 | 1-4 |
| Corrosion Inhibitor | 0.01-3 | 0.01-1.5 |
| Oxidation inhibitor | 0.10-5 | 0.01-1.5 |
| Dispersant | 0.1-10 | 0.1-5 |
| Lube Oil Flow Improver | 0.01-2 | 0.01-1.5 |
| Detergents and Rust Inhibitors | 0.01-6 | 0.01-3 |
| Anti-Foaming Agents | 0.001-0.1 | 0.001-0.01 |
| Anti-wear Agents | 0.001-5 | 0.001-1.5 |
| Seal Swellant | 0.1-8 | 0.1-4 |
| Friction Modifiers | 0.01-3 | 0.01-1.5 |
| Lubricating Base Oil | Balance | Balance |

In broad sense therefore, the phosphorous- and sulfur-containing reaction product mixture additive of the present invention, when employed in a lubricating oil composition, typically in a minor amount, is effective to impart at least one of enhanced anti-wear and anti-oxidant, relative to the same composition in the absence of the present additive. Additional conventional additives, particularly dispersants and friction modifiers, selected to meet the particular requirements of a selected type of lubricating oil composition also can be included as desired.

Accordingly, while any effective amount of the phosphorous- and sulfur-containing mixed reaction product additive can be incorporated into a lubricating oil composition, it is contemplated that such effective amount be sufficient to provide a given composition with an amount of the additive of typically from about 0.01 to about 25, preferably from about 0.1 to about 5.0, and most preferably from about 25 to about 1.0 wt. %, based on the weight of said composition. Similarly, while any effective amount of a friction modifier additive can be incorporated into an oil composition, it is contemplated that such effective amount be sufficient to provide said composition with an amount of the friction modifier additive of typically from about 0.05 to about 1, preferably from about 0.08 to about 0.8 and most preferably from about 0.1 to about 0.50 wt. %, based on the weight of said composition, and it is contemplated that an effective amount of the a dispersant material typically will be in the range of from about 1 to about 10, preferably from 2 to about 8, and most preferably from 3 to about 6 wt. % based on the weight of the composition.

When other additives are employed, it may be desirable, although not necessary, to prepare additive concentrates comprising concentrated solutions or dispersions of the single mixed phase of phosphorous- and sulfur-containing reaction products or the top phase mixture, or the bottom phase mixture, together with the other additives (said concentrate additive mixture being referred to herein as an additive package) whereby the several additives can be added simultaneously to the base oil to form the lubricating oil compositions. Dissolution of the additive concentrate into the lubricating oil may be facilitated by solvents and by mixing accompanied with mild heating, but this is not essential. The concentrate or additive package typically will be formulated to contain either the top phase mixture, the bottom phase mixture, or the mixed or single phase mixture of phosporus- and sulfur-containing reaction products of this invention and optional additional additives in proper amounts to provide the desired concentration in the final formulation when the additive package is combined with a predetermined amount of base lubricant. Thus, any of the phosporus- and sulfur-containing reaction product mixtures of this invention can be added to small amounts of base oil or, optionally, to other compatible solvents, along with other desirable additives to form concentrates containing active ingredients in collective amounts of typically from about 25 to about 100, and preferably from about 65 to about 95, and most preferably from about 75 to about 90 wt. % additives in the appropriate proportions, with the remainder being base oil.

The final formulation may employ typically about 10 wt. % of the additive package with the remainder being base oil.

All of said weight percents expressed herein are based on active ingredient (a.i.) content of the additive, and/or upon the total weight of any additive package, or formulation which will be the sum of the a.i. weight of each additive plus the weight of total oil or diluent.

The use of the present phosphorous- and sulfur-containing anti-wear additives permit the formulator to flexibly tailor an ATF in order to achieve the balance of properties required under today's more stringent transmission manufacturers' specifications.

The following examples are given as specific illustrations of the claimed invention. It should be understood, however, that the invention is not limited to the specific details set forth in the examples. All parts and percentages in the examples as well as in the remainder of the specification and claims are by weight unless otherwise specified.

EXAMPLE 1

A phosphorous- and sulfur-containing reaction product mixture was prepared by adding to a 500 ml round bottom 4-neck flask equipped with a reflux condenser, a stirring bar and a nitrogen bubbler 166 grams of triethyl phosphite, 246 grams of hydroxyethyl-n-dodecyl sulfide, 122 grams of thiobisethanol, and 0.05 grams of sodium methoxide. The reaction flask was sealed and flushed with nitrogen, and the contents thereof was heated to 100° C. The reaction temperature was maintained at 100° C. until approximately 2-2½ moles of ethanol were recovered as overhead (about 2¾ hours). Heating at 100° C. was continued until infrared analysis indicated a product rearrangement such that the 4.1 micron hydrogen phosphite peak exceeded the hydroxyl peak, which hydroxyl peak had not yet fully disappeared. This continued heating took about 3 hours, during which time almost no additional ethanol came off. The resulting reaction product was found to contain 6.9 wt % phosphorous and 15.56 wt. % sulfur and existed as a single phase mixture.

EXAMPLE 2

The procedure of EXAMPLE 1 was repeated except that 124 grams of trimethyl phosphite were substituted for the triethyl phosphite. The reactants were heated at 100° C. for a total of 5¾ hours, during which time 51 ml. of methanol were collected and the 4.1 micron hydrogen phosphite IR peak exceeded the hydroxyl peak, but the hydroxyl peak had not yet disappeared. The resulting single phase product mixture was analyzed and found to contain 4.68 wt. % phosphorous and 15.30 wt. % sulfur.

EXAMPLE 3

The procedure of EXAMPLE 1 was followed, except that 250 grams of tributyl phosphite were used in place of triethyl phosphite. The reaction temperature was maintained at 100° C. for a total of 10 hours, during which time 180 ml of butanol were collected and the hydrogen phosphite IR peak exceeded the hydroxyl IR peak. The resulting single phase product mixture was analyzed and found to contain 5.8 wt. % phosphorous and 11.7 wt. % sulfur.

EXAMPLE 4

Part A

A polyisobutenyl succinic anhydride (PIBSA) having an SA:PIB ratio, i.e. functionality, of 1.04, was prepared by heating a mixture of 100 parts of polyisobutylene (PIB) having a number average molecular weight (Mn) of 940 with 13 parts of maleic anhydride to a temperature of about 220° C. When the temperature reached 120° C., chlorine addition was begun and 1.05 parts of chlorine at a constant rate were added to the hot mixture for about 5 hours. The reaction mixture was then heat soaked at 220° C. for about 1.5 hours and then stripped with nitrogen for about 1 hour. The resulting polyisobutenyl succinic anhydride had an ASTM Saponification Number of 112 which calculates to a succinic anhydride (SA) to polyisobutylene (PIB) ratio of 1.04 based upon the starting PIB as follows:

$$\frac{SA:PIB \text{ ratio}}{\text{(Functionality)}} = \frac{SAP \times M_n}{112200 - (96 \times SAP)} = \frac{112 \times 940}{112200 - (96 \times 112)} = 1.04$$

The PIBSA product composition was 90 wt. % active ingredient (a.i.), the remainder being primarily unreacted PIB. The SA:PIB ratio of 1.04 is based upon the total PIB charged to the reactor as starting material, i.e., both the PIB which reacts and the PIB which remains unreacted.

Part B

The PIBSA of Part A was animated as follows: 1500 grams (1.5 moles) of the PIBSA and 1666 grams of S150N lubricating oil (solvent neutral oil having a viscosity of about 150 SSU at 100° C.) were mixed in a reaction flask and heated to about 149° C. Then, 193 grams (1 mole) of a commercial grade of polyethyleneamine which was a mixture of polyethyleneamines averaging about 5 to 7 nitrogen per molecule, hereinafter referred to as PAM, was added and the mixture was heated to 150° C. for about 2 hours; followed by 0.5 hours of nitrogen stripping, then cooling to give the final product (PIBSA-PAM). This product had a viscosity of 140 cs. at 100° C., a nitrogen content of 2.12 wt. % and contained approximately 50 wt. % PIBSA-PAM and 50 wt. % unreacted PIB and mineral oil (S150N).

Part C

The PIBSA-PAM of Part B was borated as follows: 98 parts by weight of the PIBSA-PAM were mixed with 2 parts by weight of boric acid and the mixture was heated to 160° C. while stirring and blowing the reaction mass with nitrogen. The mixture was kept at 160° C. for 2 hours, sparged with nitrogen for 1 hour and filtered. The resulting product was analyzed for 0.35 % boron.

EXAMPLE 5

A hydroxyl amine of the formula:

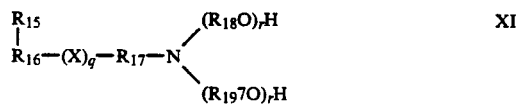

wherein q is 1; X is O; R16 is a $C_{18}$ aliphatic hydrocarbon radical; $R_{15}$ is H; $R_{17}$ is $C_3$ alkylene; $R_{18}$ and $R_{19}$ are $C_2$ alkylene; and each r is 1 was prepared by first reacting 270 parts by weight of octadecyl alcohol with 53 parts by weight of acrylonitrile in the presence of KOH at a temperature in the range of 100° to 110° F. for about 18 hours to form an ether nitrile intermediate. The intermediate was then hydrogenated in the presence of a Raney Nickel catalyst at a temperature in the range of from 270° to 280° F. until 2 moles of hydgrogen had been absorbed. The ether amine was then reacted with 88 parts by weight of ethylene oxide at a temperature in the range of about 280° F. for 12 hours to form the hydroxyl amine product.

EXAMPLE 6

An ATF base fluid, designated hereinafter as the Test Base, was formulated with conventional amounts of seal swell additive, anti-oxidant, viscosity index improver and mineral oil base.

To a sample of the Test Base there was added 4.4 wt. % of the borated PIBSA-PAM dispersant of EXAMPLE 4, Part C, together with 0.5 wt. % of the phosphorous- and sulfur-containing mixture prepared in accordance with EXAMPLE 1 and 0.15 wt. % of a hydroxyl amine friction modifier in accordance with formula XI of EXAMPLE 5 above. The resulting formulation is designated Formulation 1.

To another sample of the Test Base there was added 4.4 wt. % of the borated PIBSA-PAM dispersant of EXAMPLE 4, Part C, 0.5% of the phosphorous- and sulfur-containing mixture prepared in accordance with EXAMPLE 1 and 0.15 wt. % of a hydroxyl amine friction modifier in accordance with formula XI of EXAMPLE 5 above wherein q is 0, $R_{15}$ is hydrogen, $R_{16}$ and $R_{17}$, combined, are a $C_{18}$ aliphatic hydrocarbon radical, $R_{18}$ and $R_{19}$ are $C_2$ alkylene, and each r is 1. The hydroxyl amine compound is a commercial product which is available under the trade designation Ethomeen 18-12 from the Armak Chemical Division of Akzo Chemie. The resulting formulation is designated Formulation 2.

To a sample of the Formulation 1 there was added 0.10 wt % of an overbased sulfonate detergent. The resulting formulation is designated Formulation 3.

To another sample of the Test Base there was added 4.4 wt. % of the borated PIBSA-PAM of EXAMPLE 4, 0.5 wt. % of the phosphorous- and sulfur-containing product mixture of EXAMPLE 2, and 0.15 wt. % of the hydroxyl amine friction modifier of EXAMPLE 5. The resulting formulation is designated Formulation 4.

To another sample of the Test Base there was added 4.4 wt. % of the borated PIBSA-PAM of EXAMPLE 4, along with 0.5 wt. % the phosphorous- and sulfur-containing product mixture of EXAMPLE 3 and 0.15 wt. % of the hydroxyl amine friction modifier that was used in Formulation 1. The resulting formulation is designated Formulation 5.

To another sample of the Test Base there was added 4.4 wt. % of the borated PIBSA-PAM dispersant of EXAMPLE 4, together with 0.15 wt. % of the hydroxyl amine friction modifier that was used in Formulation 1. The resulting formulation is designed Comparative Formulation 6C.

To another sample of the Test Base there was added 4.4 wt. % of the borated PIBSA-PAM dispersant that was used in Formulation 1, together with 0.5 wt. % of zinc ($C_4$-$C_5$) dialkyl dithiophosphite (ZDDP) and 0.15 wt. % of the hydroxyl amine friction modifier that was used in Formulation 1. The resulting formulation is designed at Comparative Formulation 7C.

Another formulation, Formulation 8, was prepared in the same manner as Formulation 1, except that 0.2 wt. % of hydroxyl amine the friction modifier in accordance with formula XI of EXAMPLE 5 was used instead of 0.01 wt. %.

The compositions of Formulations 1-8 are summarized in Table 6 as follows:

TABLE 6

| Component, wt. % | \multicolumn{8}{c}{Formulation Number} | | | | | | | |
|---|---|---|---|---|---|---|---|---|
| | 1 | 2 | 3 | 4 | 5 | 6C | 7C | 8 |
| borated PIBSA-PAM | 4.4 | 4.4 | 4.4 | 4.4 | 4.4 | 4.4 | 4.4 | 4.4 |
| phosphorous- and sulfur-containing product mixture (EXAMPLE 1) | 0.5 | 0.5 | 0.5 | — | — | — | — | 0.5 |
| phosphorous- and sulfur-containing product mixture (EXAMPLE 2) | — | — | — | 0.5 | — | — | — | — |
| phosphorous- and sulfur-containing product mixture (EXAMPLE 3) | — | — | — | — | 0.5 | — | — | — |
| hydroxyl amine, q = 0 | — | 0.15 | — | — | — | — | — | — |
| hydroxyl amine, q = 1, X = 0 | 0.15 | — | 0.15 | 0.15 | 0.15 | 0.15 | 0.15 | 0.15 |
| overbased sulfonate detergent | — | — | 0.10 | — | — | — | — | — |
| ZDDP | — | — | — | — | — | — | 0.5 | — |
| Test Base | 94.95 | 94.95 | 94.95 | 94.95 | 94.95 | 94.95 | 94.95 | 94.95 |

The Formulations 1 to 7C were then tested for their anti-wear properties using the FZG Gear Test.

FZG Gear Test

This test employs a gear box containing a wheel gear engaged with a pinion gear. The pinion gear is connected by an axle to a motor. The motor turns the pinion gear through the axle and the pinion gear serves to drive the wheel gear. The wheel gear is connected to a different axle which extends out of the gear box. A load is applied to the wheel gear during the test which creates resistance to the turning of the wheel gear by the pinion gear. This load is applied in several stages and increases in each stage. The load is expressed as torque (N.m) at the pinion gear.

Thus, the load of each load stage can be expressed as follows:

| Stage No. | Torque at Pinion (N.m.) | Stage No. | Torque at Pinion (N.m.) |
|---|---|---|---|
| 1 | 3.3 | 7 | 183.4 |
| 2 | 13.7 | 8 | 239.3 |
| 3 | 35.3 | 9 | 302 |
| 4 | 60.8 | 10 | 372.6 |
| 5 | 91.1 | 11 | 450.1 |
| 6 | 135.3 | 12 | 534.5 |

Prior to the start of each run, the test gear box is carefully flushed twice with a suitable solvent (non-flammable). The solvent is filled above the center of the shaft axles. The machine is then turned one full rotation by hand to remove waste oil from the bearings assemblies. The complete housing is then dried thoroughly.

The test gears are likewise washed. The tooth flanks are visually inspected from a fixed viewing distance of 25 cm. Existing irregularities are noted. Test wheels with any signs of rusting or corrosion are discarded.

The pinion and wheel gears are marked in such a way that when the test pieces are reassembled, the same teeth mesh as before. After installing the pinion gear on its shaft and the wheel gear on its shaft, the test gear box is filled with the oil formulation to be tested up to the center of the shafts. A preliminary run is made at the first load stage while heating until the temperature has reached 90°±3° C. The motor and rig are turned off until the next load stage is run.

The pinion and wheel gears are disassembled at the end of each load stage, washed in solvent, allowed to cool to room temperature, washed again and this time dried with an air gun.

The test gears are then separately examined at the fixed viewing distance for changes in appearance of the flanks. Thus, smoothing of the grinding marks, scratches, scoring, seizure marks, discoloration of the tooth flanks, corrosion symptoms, deposits, the natural position, and extent of the change on the tooth flanks are all noted.

The inspected gears are then re-mounted on the shafts for the next load stage. The same oil is used and the load stages are increased until a marked deviation (e.g. increase) in deterioration of the visible appearance of the gears is observed relative to the progressive deterioration observed in previous load stages. When such deterioration is observed the oil fails that load stage and the test is completed.

The following is a summary of the test conditions of the FZG test.

| TEST CONDITIONS | |
|---|---|
| Complete Revolutions of Wheel Gear per Load Stage | 21,700 |
| Pinion Speed | 2,170 RPM |
| Drive Gear | Pinion |
| Lubrication | Splash or Dip |
| Oil Temp. at Beginning of Test Run | 90 ± 3° C. |
| Amount of Oil Needed (Center of Shaft) | 1.25L |
| Running Time Per Load Stage | 15 min. |

The results of testing each formulation are summarized at Table 7, Runs 1 to 6.

TABLE 7

| Run No. | Formulation | Antiwear Additive | Highest FZG Load Stage To Failure |
|---|---|---|---|
| 1 | 1 | phosphorous- and sulfur- containing mixture of (EXAMPLE 1) | 12 |
| 2 | 2 | phosphorous- and sulfur- containing mixture of (EXAMPLE 1) | 12 |
| 3 | 3 | phosphorous- and sulfur- containing mixture of (EXAMPLE 1) | 12 |
| 4 | 4 | phosphorous- and sulfur- containing mixture of (EXAMPLE 2) | 12 |
| 5 | 5 | phosphorous- and sulfur- containing mixture of (EXAMPLE 3) | 12 |
| 6 | 6C | NONE | 6 |
| 7 | 7C | ZDDP | 7-8 |

Referring to Table 7, it can be seen that all of the tested phosphorous- and sulfur-containing product mixtures are better than ZDDP (run 7C) with respect to anti-wear. The tested formulations which contain the phosphorous- and sulfur-containing mixtures clearly are superior to Formulation 6C which contains no anti-wear additive

4000 CYCLE FRICTION TEST

This test uses an SAE No. 2 type friction machine operated successfully for 4000 cycles wherein no unusual clutch plate wear or composition-face plate flaking occurs. The test is conducted in a continuous series of 20 second cycles, each cycle consisting of three phases as follows: Phase I (10 seconds)—motor on at speed of 3,600 rpm, clutch plates disengaged; Phase II (5 seconds)—motor off, clutch plates engaged; and Phase III (5 seconds)—motor off, clutch plates released. 4000 cycles are repeated using 20740 J. of flywheel energy at 40 psi. of applied clutch pressure. During the clutch engagement, friction torque is recorded as a function of time as the motor speed declines from 3600 rpm to 0. From the torque traces, the dynamic torque ($T_D$) is determined midway between the start and end of clutch engagement (i.e. at a motor speed of 1800 rpm), as well as the torque ($T_0$) just before lock-up, e.g. between 0 and 20 rpm. The amount of time in seconds in phase II it takes for the motor speed to go from 3600 to 0 rpm is referred to as the lock-up time. The torque ratio of the oil formulation is then determined from ($T_0/T_D$) as is the torque difference ($T_0/T_D$). In addition to determining midpoint dynamic torque ($T_D$) and static torque ($T_0$), the breakaway static torque ($T_S$) is also determined. This is achieved by rotating the composition plates at 2 to 3 rpm under a load of 40 psi. while locking the steel reaction plates and preventing them from rotating. The torque is then measured until slippage occurs. The maximum torque observed is recorded as $T_S$. From $T_S$ is determined the Breakaway Static Torque ratio ($T_S/T_D$).

The breakaway static torque ratio expresses the ability of the transmission to resist slippage; the lower the ratio, the higher the slippage.

The above test was performed on an ATF formulation which was prepared by adding to the above-described Test Base Formulation, 4.4 wt. % of the borated PIBSA-PAM dispersant of EXAMPLE 4, together with 0.5 wt. of the phosphorous- and sulfur-containing mixture prepared in accordance with EXAMPLE 1 and 0.2 wt. % of a hydroxyl amine friction modifier in accordance with formula XI of EXAMPLE 5, the resulting formulation being referred to hereinafter as Formulation 8.

The following is a summary of the test conditions:

| Cycle Rate: | 3 per minute |
|---|---|
| Cycle Make-up: | Motor on, clutch released 10 sec |
| | Motor off, clutch applied 5 sec |
| | Motor off, clutch released 5 sec |
| Temperature: | 115 +/− 5° C. |
| Pressure: | 275 +/− 3 kPa |
| Velocity: | 3600 rpm |
| Energy: | 20740 +/1 100 J |
| Fluid Quantity: | 305 mL +/− 5 mL |
| Paper Speed: | 100 mm per sec |
| Torque Calibration | 2700 Nm |
| Total Cycles: | 4000 |

The results of the test are shown in Table 8.

TABLE 8

| 4000 CYCLE FRICTION TEST | | | | | |
|---|---|---|---|---|---|
| Test Cycle | $T_D$(N.m) | $T_O$(N.m) | $T_S$(N.m) | $T_OT_D$ | Temp. |
| 200 | 129 | 118 | 95 | 0.91 | 117° C. |
| 4000 | 136 | 119 | 91 | 0.88 | 116° C. |

The data reported in Table 8, which is derived from 4000 cycle friction test, at 200 cycles and 4000 cycles, shows using Formulation 8 resulted in a change in $T_O/T_D$ of only 0.03 between the 200th and 4000th cycles; a change which reflects good friction stability.

Formulations 1 and 3 were then tested in the High-energy, Friction Characteristics and Durability Test (HEFCAD) described in Dexron IIR Specification GM6137-M, Published by GMC Engineering Staff, Engineering Standards Section. This test is run for about 18,000 cycles (i.e. 100 hours).

This test uses a SAE No. 2 Friction Machine operated successfully for 100 hours wherein no unusual clutch plate wear or composition-face plate flaking occurs. After a break-in period of 24 hours, the test is conducted in a continuous series of 20 second cycles, each cycle consisting of three phases as follows: Phase I (10 seconds)—motor on at speed of 3,600 rpm, clutch plates disengaged; Phase II (5 seconds)—motor off, clutch plates engaged; and Phase III (5 seconds)—motor off, clutch plates released. The cycles are repeated for 75 hours after the break-in (i.e. a total of 18,000 cycles) or until failure. The static torque ($T_O$) in the HEFCAD procedure is measured at an engine speed (rpm) at which the slope of the torque curve approaches infinity, e.g. between 20 and about 0 rpm. The dynamic torque ($T_D$) is measured midway between the start and end of clutch engagement, i.e. at 18000 rpm. Data is reported after 100 hours of test operation. The torque differential ($T_O - T_D$) not only expresses the primary friction characteristic but its change over the duration of the test (i.e., between completion of break-in and 100 hours of operation) reflects friction stability.

The results of the HEFCAD test for Formulations 1, 3 and 6C are summarized at Table 9.

absolute pressure, for 1.0 hour to remove additional butanol. About 137.6 ml of condensate were collected. The resulting sample was analyzed for Total Acid number (TAN) which was found to be 131.

The resulting single phase reaction product mixture was designated Additive 7', and analyzed for sulphur and phosphorus content, and subjected to phosphorous nuclear magnetic resonance ($^{31}P$ NMR) to determine the identity and amounts of phosphorus containing materials in the product mixture.

The "roto-evaporated" sample was then diluted with tridecyl alcohol to achieve a Product:Alcohol wt. ratio of 90:10. The diluted product mixture was then designated Additive 7. For the runs of Table 10, $^{31}P$ NMR spectroscopy was performed as follows:

All measurements were taken at 40° C. on a JEOL GSX-400 NMR Spectrometer operating at 161.70 MHz. Samples were all prepared to be between 20 and 30%

TABLE 9

| Run No. | Formulation No. | Antiwear Additive | Friction Modifier (Ex.5) (%) | After 18,000 Cycles | | | | Net Change in ($T_O$-$T_D$) over 100 Mr | Lock-up Time (Sec.) |
|---|---|---|---|---|---|---|---|---|---|
| | | | | $T_O$ (Mm) | $T_D$ (Mm) | $T_S$ (Mm) | $T_O$-$T_D$ | | |
| 1 | 1 | phosphorous- and sulfur-containing mixture of EXAMPLE 1 | 0.15 v/v | 141 | 138 | N/D | +3 | +1 | 64 |
| 3 | 3 | phosphorous- and sulfur- containing mixture of EXAMPLE 1 | 0.15 v/v | 139 | 136 | N/D | +3 | 0 | 65 |
| 6 | 6C | None | 0.15 v/v | 127 | 130 | N/D | −3 | +3 | 7 |
| 8 | 9 | Additive 7 | 0.21 w/w | 146 | 141 | 99 | +5 | +5 | 0.67 |
| 9 | 10 | Additive 8 | 0.54 w/v | 127 | 130 | 84 | −3 | +3 | ND |

The data in Table 9 demonstrates that high dynamic torques are obtained with Runs 1, 3 and 8 relative to Run 6, and thus shows that even with high treat rates of the products of the invention, high dynamic friction is maintained, potentially even increased. While the data from Run 9 does not exhibit relatively enhanced friction performance, neither does it show any adverse influence. This further illustrates the non-deleterious effects the products have on fluid friction performance.

EXAMPLE 7

A phosphorous- and sulfur-containing reaction product mixture was prepared by adding to a 2L round bottom 4-neck flask, 582.60 grams (3.00 moles) of dibutyl phosphite, 492 grams (2.00 moles) of hydroxyethyl-n- dodecyl sulfide, and 244.01 grams (2.00 moles) of thiobisethanol. After mixing, a stopper, thermometer, air driven stirrer, and Dean Starke trap connected to a condenser were then attached to the flask. A nitrogen flow was begun through the flask and allowed to flow through the Dean Stark tube, up the the condenser, and out a bubbler. The clear, colorless liquid mixture was then heated to 95° C. under nitrogen while being stirred. The reaction temperature was maintained at 95° C. for 9.5 hours, after which time the reaction was shut down over night. The reaction was restarted the next day and run for 1 hour at 95° C. until infrared analysis indicated the reaction had proceeded such that the 4.1 micron hydrogen phosphite peak exceeded the hydroxyl peak, which hydroxyl peak had not yet fully disappeared. The total reaction time at 95° C. was 10.5 hours, during which time about 9.0 mls of butanol were collected.

About 1,272 grams of the resulting product mixture were then placed in a 1L, 1-neck flask and "roto-evaporated" under a nitrogen flush at 70° C., 0.7 mmHg wt/wt in $CDCl_3$. Standard single pulse experiments were used with a preacquisition pulse delay of 6 sec and 45° observe flip angle. All broadband $^1H$ decoupling was gated off during preacquisition and evolution and on during data acquisition. These conditions assure that the observed signals are relatively quantitative.

Chemical shifts reported are referenced to concentrated $H_3PO_4$ contained externally in a capillary tube. The spectral observation window was selected to be 35211.3 Hz or 2 times the normal chemical shift range with 32K data points per scan. All fast Fourier transforms were done with a normal gaussian line broadening of 1–4 Hz. Integration intensities were digitially measured and the values were normalized to mole percents.

The results are summarized in Table 10, (Run 8).

EXAMPLE 8

A phosphorous- and sulfur-containing reaction product mixture was prepared by adding to a 500 ml round bottom 4-neck flask equipped with a reflux condenser, a stirring bar and a nitrogen bubbler, 194 grams (1 mole) of dibutyl phosphite, 246 grams (1 mole) of hydroxyethyl-n-dodecyl sulfide, and 122 grams (1 mole) of thiobisethanol. The reaction flask was sealed and flushed with nitrogen, and the contents thereof heated to 95° C. and maintained thereat for 10 hours. The reaction temperature was then raised to 105° C. and maintained thereat for 9 hours, for a total reaction time of 19 hours. Approximately 13.25 gms of butanol were recovered as overhead.

The resulting product mixture was then "roto-evaporated" in accordance with EXAMPLE 7 at 85° C. and an additional 49.50 gms of condensate collected.

The single phase reaction product mixture was designated Additive 8', and was then subjected to phosphorous nuclear magnetic resonance ($^{31}P$ NMR) to determine the identity and amounts of phosphorus containing materials in the product mixture.

The "roto-evaporated" product mixture was then diluted with tridecyl alcohol at a 90:10 weight ratio in accordance with EXAMPLE 7. The diluted product mixture was then designated Additive 8 and analyzed for sulfur and phosphorous content.

The $^{31}P$ NMR results are summarized in Table 10 (Run 9).

EXAMPLE 9

Part A

A phosphorous- and sulfur-containing reaction product mixture was prepared by mixing in a reactor, tributyl phosphite (75 parts by wt), hydroxyethyl-n-dodecyl sulfide (73.8 parts by wt), thiobisethanol (36.6 parts by wt), and sodium methoxide, at a respective molar ratio of 1:1:1:0.0021. A nitrogen purge was then connected to the reactor and and the reactor heated to 115° C. over a period of 1 hour while stirring. The reaction temperature was maintained at 115° C. for 9.25 hours until infrared analysis indicated the reaction had proceeded such that the 4.1 micron hydrogen phosphite peak exceeded the hydroxyl peak, which hydroxyl peak had not yet fully disappeared. About 2 parts by wt of condensate were collected during reaction.

The resulting product mixture was then "roto-evaporated" under a nitrogen flush at 90° C., 0.7 mmHg absolute, for 11.0 hours to remove butanol. About 9.7 parts by wt of additional condensate were collected. The resulting sample was analyzed for Total Acid number (TAN) which was found to be 79.4.

The resulting single phase reaction product mixture was designated Additive 9' then analyzed for sulphur and phosphorus content, and subjected to phosphorous nuclear magnetic resonance ($^{31}P$ NMR) to determine the identity and amounts of phosphorus containing materials in the product mixture. In addition it was subjected to $^{13}C$ NMR analysis.

The "roto-evaporated" product mixture was then diluted with tridecyl alcohol at a 90:10 weight ratio in accordance with EXAMPLE 7. The diluted reaction product mixture was designated Additive 9.

For the runs of Table 10, $^{13}C$ NMR spectroscopy was performed as follows:

All $^{13}C$ measurements were taken on a JEOL GSX-400 NMR Spectrometer operating at 100.40 MHz. The samples were prepared to be between 20 and 30% wt/wt in $CDCl_3$. A standard single pulse experiment was used with a 90° flip angle, and preacquisition delay 4 sec. Broadband proton decoupling was gated off during preacquisition and evolution and on throughout data acquisition.

Chemical shifts reported are internally referenced to deuterochloroform. The spectral observation window was selected to be 24038.5 Hz with 6K data points per scan. All FFTs were done with a 4 Hz gaussian line broadening multiplication prior to transformation. Integral intensities were digitally measured and the values were reported in mole percents.

The results are summarized at Table 10 (Run 10).

Part B

A sample of Additive 9' before dilution with tridecyl alcohol was placed in a beaker under a fume hood at room temperature for 7 days. The undiluted product mixture separated into 2 phases. The top phase was designated Additive 9A and the bottom phase was designated Additive 9B.

EXAMPLE 10

Part A

A phosphorous- and sulfur-containing reaction product mixture was prepared by mixing in a 2L round bottom 4-neck flask, tributyl phosphite (500.63 parts by wt), hydroxyethyl-n-dodecyl sulfide (492.04 parts by wt), thiobisethanol (244.09 parts by wt), and sodium methoxide (0.23 parts by wt), at a respective molar ratio of 1:1:1:0.0021. A nitrogen purge was then connected to the reactor and and the reactor heated to 115° C. over a period of 0.75 hour while stirring. The reaction temperature was maintained at 115° C. for about 7.5 hours until infrared analysis indicated that the reaction had proceeded such that the 4.1 micron hydrogen phosphite peak exceeded the hydroxyl peak, which hydroxyl peak had not yet fully disappeared. The reaction was interrupted once after 4 hours reaction time and restarted the next day to complete the remaining 3.5 hours. About 7.24 parts of butanol were collected during reaction.

The resulting product mixture was then "roto-evaporated" under a nitrogen flush at 70° C., 0.3 mmHg absolute, for 2.0 hour to remove butanol. About 119.44 parts by weight of additional condensate were collected. The resulting sample was analyzed for Total Acid number (TAN) which was found to be 79.4.

The resulting single phase reaction product mixture was designated Additive 10, and was then analyzed for sulphur and phosphorus content.

The results are summarized at Table 10 (Run 11).

Part B

A sample of 633.84 parts of Additive 10 was placed in a fume hood and allowed to sit, exposed to air for about 12 days. Additive 10 separated into two phases after this prolonged exposure to air.

The two phase mixture was transferred to a 2L separatory funnel and again allowed to separate. The bottom phase was collected from the funnel, weighed, and designated Additive 10B. The top phase was designated Additive 10A and also weighed. The top phase consisted of 48 weight % of the total mixture and the bottom phase consisted of 52 weight % of the total mixture.

Additives 10A and 10B were then analyzed for sulphur and phosphorus content, and subjected to phosphorous nuclear magnetic resonance ($^{31}P$ NMR) and $^{13}C$ NMR analysis. The results are summarized at Table 10 at runs 11A and 11B.

EXAMPLE 11

A phosphorous- and sulfur-containing reaction product mixture was prepared by placing thiobisethanol (244 gms), hydroxyethyl-n-dodecyl sulfide (492 gms) and dibutyl hydrogen phosphite (388 gms) into a 2 liter round bottom flask fitted with a Dean Starke trap, condenser, stirrer, thermometer and nitrogen flush. The contents of the flask were heated to 95° C. under nitrogen with stirring. The mixture was held at this temperature for a total of 13 hours, during which time 22 gms of butanol were collected in the Dean Starke trap. When the reaction was terminated the infrared analysis showed that the relative height of the 4.1 micron hydrogen phosphite peak exceed that of the hydroxyl peak, but the hydroxyl peak had not disappeared.

About 1,066 gms of this product was then "roto-evaporated" at 70° C., under 0.4 mm Hg for 90 minutes with a slow nitrogen sparge. This process removed an additional 103 gms of butanol.

The product was found to contain 13.1% sulfur and have a total acid number of 98.

This product was designated additive 11'. Additive 11' was analyzed in the same manner as set forth in connection with Additives 10A and 10B and the results of the analysis as shown in Table 10 (Run 12).

Test Base A in each formulation prepared is summarized at Table 11.

Additives 7 through 10B are described in detail at Table 11, and the preparation thereof at EXAMPLES 7 to 10. The resulting formulations were tested for FZG wear performance, friction modification, including HEFCAD, and 4000 Cycle Friction tests, as indicated at Tables 7, 9 and 12. The procedure for such tests are described above. The results of these tests are provide therein also.

TABLE 10

| | | | Phase Analyzed | | | Phosphorous Containing Species by 31-PNMR (mole %)** | | | | | |
|---|---|---|---|---|---|---|---|---|---|---|---|
| Run No. | Reactants* | Mole Ratio of Reactants | Single Phase (W %) | Top Phase (W %) | Bottom Phase (W %) | (1) "R"O\\‖P—H/HO | (2) "R"O\\‖P—H/"R" | (3) "R"O\\‖P—R"/"R" | (4) "R"O\\‖P—S—R"/H | (5) HO O\\‖P—H/HO | (6) Other |
| 8 | A + B + C Additive 7' | 1.5:1:1 | 100 | N/A | N/A | 51 | 6 | 0 | ≦1 | 41 | <1 |
| 9 | A + B + C Additive 8' | 1:1:1 | 100 | N/A | N/A | 56 | 8 | 0 | ≦1 | 35 | <1 |
| 10 | A' + B + C Additive 9' | 1:1:1 | 100 | N/A | N/A | 41 | 16 | 10 | 3 | 27 | 3 |
| 11 | A' + B + C Additive 10 | 1:1:1 | 100 | N/A | N/A | 56 | 11 | 7 | 1 | 22 | 3 |
| 11A | A' + B + C Additive 10A | 1:1:1 | N/A | 48 | N/A | 57 | 13 | 16 | 2 | 4 | 8 |
| 11B | A' + B + C Additive 10B | 1:1:1 | N/A | N/A | 52 | 8 | <1 | 7 | <1 | 80 | 4 |
| 12 | A' + B + C Additive 11' | 1:1:1 | 100 | N/A | N/A | 41 | 4 | <1 | <1 | 52 | 2 |

| Run No. | Elemental Analysis (W %) | TAN (ngk OM/gm) | 13C-NMR Analysis (mole %)*** | | | |
|---|---|---|---|---|---|---|
| | | | Non-Phos. Containing Oxyethers | P-ester | Alcohol | EPI Sulfonium Salt |
| 8 | S = 8.6 P = 7.9 | 131 | 47 | 36 | 6 | 11 |
| 9 | S = 2.70 P = N/D | N/D | 58 | 20 | 14 | 8 |
| 10 | S = 11.48 P = 4.89 | | 60 | 30 | 3 | 7 |
| 11 | S = 12.2 P = 5.73 | 79.4 | 53 | 36 | 5 | 6 |
| 11A | S = 13.1 P = 2.0 | 37.5 | 70 | 13 | 13 | 3 |
| 11B | S = 11 P = 10 | 140 | 49 | 20 | 20 | 11 |
| 12 | S = 13.1 P = N/D | 98 | 46 | 22 | 14 | 18 |

*A = dibutyl phosphite
A' = tributyl phospite
B = thiobisethanol
C = nC$_{12}$—S—CH$_2$CH$_2$OH
N/A = Not Applicable
N/D = Not Determined
**"R" and R" are as defined in Example 1 except that R" includes butyl insstead of ethyl
***P-ester = Phosphite esters as depicted by species 1 to 4 and 6
non-phos. containing oxyethers = non-phosphorous containing species having oxyether groups present as generally depicted at Table 4

EXAMPLE 12

Various ATF formulations were prepared containing borated PIBSA-PAM dispersant of EXAMPLE 4, anti-oxidant seal swell additive, anti-wear additive derived from EXAMPLES 7 to 10, friction modifier derived from EXAMPLE 5 mineral base oil, and viscosity modifier. For convenience, the mineral base oil in combination with conventional amounts of the seal swell, anti-oxidant, and viscosity modifier are referred to herein as Test Base A. The amounts and identity of dispersant, anti-wear additive, and friction modifier present with

TABLE 11

| Component, wt. % | Formulation Number | | | | | |
|---|---|---|---|---|---|---|
| | 9 | 10 | 11 | 12 | 13 | 14 |
| borated PIBSA-PAM | 4.0 | 4.0 | 4.0 | 4.7 | 4.7 | 4.0 |
| Additive 7 | 0.42 | — | — | — | — | — |
| Additive 8 | — | 0.54 | — | — | — | — |
| Additive 9 | — | — | 0.60 | — | — | — |
| Additive 9A | — | — | — | .55 | — | — |
| Additive 9B | — | — | — | — | .55 | — |
| Additive 12 | — | — | — | — | — | .54 |
| hydroxyl amine q = 1, x = 0 | 0.21 | 0.21 | 0.21 | .21 | .21 | .21 |
| Test Base A | 95.37 | 95.25 | 95.19 | 94.54 | 94.54 | 95.25 |

TABLE 12

| Run No. | Formulation No. | Antiwear Additive | Test Cycle | 4,000 Cycle Friction Test |  |  |  |  |  |
|---|---|---|---|---|---|---|---|---|---|
| | | | | $T_D$ (Mm) | $T_O$ (Mm) | $T_S$ (Mm) | $T_O/T_D$ | Lock-up (Sec.) | Temp °C. |
| 8 | 9 | Additive 7 | 200 | 129 | 119 | 87 | 0.92 | 0.93 | 116 |
| | | | 4,000 | 140 | 127 | 99 | 0.91 | 0.87 | 116 |
| 9 | 10 | Additive 8 | 200 | 125 | 115 | 97 | 0.92 | 0.96 | 116 |
| | | | 4,000 | 138 | 126 | 95 | 0.91 | 0.87 | 116 |
| 10 | 11 | Additive 7 | 2,000 | 136 | 124 | 114 | 0.95 | 0.87 | 116 |
| | | | 4,000 | 133 | 118 | 103 | 0.89 | 0.91 | 116 |

ANTI-WEAR TEST

A sample of the Formulation 8 was tested for its anti-wear properties. The fluid to be evaluated is run in a motor driven power steering pump at a speed of 2950 rev./min (pump outlet pressure of 6200 kPa and pump-out fluid temperature of 145° to 150° C.) for 50 test hours as per the GM DEXRONR II specification GM6137-M. The fluid's anti-wear performance was evaluated at the end of the test by disassembling the pump and visually inspecting for evidence of scuffing, scoring, or chatter wear.

The following is a summary of the test condition:

| Limits | Max. | Min. | Avg. |
|---|---|---|---|
| Pump-out, °C. 145 to 150 | 148 | 145 | 146 |
| Sump, °C. | 138 | 136 | 137 |
| Pressure, kPa 6,200 ± 70 | 6260 | 6180 | 6214 |
| Speed, rpm 2,950 ± 50 | 2933 | 2929 | 2931 |
| Fluid Level at End of Test | | No change | |
| Shut downs | | None | |

The test evaluation for Formulation 8 indicated that the cam ring grinding pattern remaining after 50 test hours was 95-98%, that there was no visually detectable scuffing, scoring or chatter wear, and that the pressure and thrust plates showed only trace scratching. The fluid was given a good pass rating.

VICKERS ANTI-WEAR TEST

This vane pump wear test is fully described in ASTM procedure D2882. It uses a constant volume high pressure vane pump to indicate wear characteristics of petroleum and non-petroleum hydraulic fluids. The procedure used in the testing conducted herein differs from ASTM D2882 only in pump outlet pressure (1000 psi versus 2000 psi) and fluid temperature (175° F.) as per the Ford Engineering Spec WSP-M2C185A MERCON ®. The conditions for the testing are as follows:

| | |
|---|---|
| Pump Outlet Pressure | 1000 ± 20 psi |
| Fluid Temperature, Pump Inlet | 175 ± 5° F. |
| Pump Speed | 1200 ± 60 rpm |
| Fluid Change | 3 gallons |
| Total Test Completion Time | 112 hours |

The Vickers 104C vane pump cartridge is used for the testing. At the end of 100 hour test time, the cam ring and vanes are measured for total weight loss. The maximum allowable weight loss is 15 mg. Formulation 1 was tested in accordance with the above procedure, and the weight loss was only 1.7 mg.

SPRAG WEAR TEST

This sprag clutch wear test uses a General Motors model THM 440-T4 automatic transmission equipped vehicle, operated at a transmission sump temperature of 225° F. in a cyclic manner accelerating from idling to an engine speed of about 5800 rpm for 1000 cycles. After the test period, the input sprag clutch inner race, sprag assembly, and outer race are visually inspected for wear. The results of this test when using a sample of Formulation 1 as the test fluid are summarized in Table 13 as follows:

TABLE 13

| Input Sprag Clutch, Inner Race | No visual wear in element contact area |
|---|---|
| Input Sprag Clutch, Clutch assembly | No visual wear |
| Input Sprag Clutch, Outer Race | No visual wear |
| Transmission Shift Speed | 5800 rpm |
| Sump Temperature During Test, °F. | Min. 182, Max. 240, Avg. 225 |

EXAMPLE 13

A fully formulated automatic transmission fluid was prepared containing borated PIBSA-PAM dispersant, seal swell agent, friction modifier, alkylated diphenylamine and viscosity modifier. To four separate aliquots of this fluid there was added varying levels of Additive 9. The finished fluids, designated Fluid 1, Fluid 2, Fluid 3 and Fluid 4, were then run in an ISOT (Indiana Stirred Oxidation Test). The results after 48 hours at 165 degrees C. are shown in Table 14 as total acid number increase (Delta TAN) and are given as a function of the concentration of Additive 9 in the respective finished fluids.

TABLE 14

| | Fluid No. | | | |
|---|---|---|---|---|
| | 1 | 2 | 3 | 4 |
| Additive 9 (mass %) | 0.0 | 0.13 | 0.26 | 0.39 |
| Delta TAN | 3.0 | 2.3 | 2.1 | 1.6 | the product of the invention is very effective at controlling acid number build-up by oxidation

EXAMPLE 14

A fully formulated automatic transmission fluid was prepared containing borated PIBSA-PAM dispersant, seal swell agent, friction modifier, alkylated diphenyl amine and viscosity modifier. The fluid was separated into three aliquots. To a first of the aliquots there was added 0.44 weight % of Additive 8, and to a second aliquot there was added 0.62 weight of Additive 9. The third aliquot was untreated. The three aliquots were then subjected to the Laboratory Multiple Oxidation Test (LMOT). In this test, 50 ml of test fluid with 2.0 gm of iron filings and 0.5 gm of a 1% solution of copper naphthenate is heated to 150Ⓡ C. and 25 ml of air per minute is passed through the sample. Daily samples are taken and the number of days for visible sludge to appear on blotter paper is recorded. Results are given as "Days to Fail". The results obtained using the above three fluids as test samples are shown in Table 15.

TABLE 15

|  | Fluid | | |
|---|---|---|---|
|  | 1 | 2 | 3 |
| Additive 8 (mass %) | 0.44 | — | — |
| Additive 9 (mass %) | — | 0.62 | — |
| Days to Fail | 21+ | 21+ | 5 |

The data in Table 15 again show the strong anti-oxidation performance of the products of the invention.

EXAMPLE 15

An automatic transmission fluid was prepared containing the borated PIBSA-PAM dispersant of EXAMPLE 4 Part C, friction modifier of EXAMPLE 5, antioxidant, seal swell agent and viscosity modifier.

The phase separated product of Run No. 10 (Example 9) was separated into a top phase Additive 9A and a bottom phase Additive 9B. Two samples of the automatic transmission fluid above were treated, one with Additive 9A (Fluid A) and one with Additive 9B (Fluid B). An FZG gear scoring test (as described in EXAMPLE 6) was performed on each fluid. The results of the tests are shown below along with the results obtained for a test fluid (Fluid 6C) having no anti-wear agent, Fluid 6C is described more fully in EXAMPLE 6 above.

|  | Fluid A | Fluid B | Fluid 6C |
|---|---|---|---|
| wt % Additive 9A | 0.5 | — | — |
| wt % Additive 9B | — | 0.5 | — |
| FZG, load stages to failure | 10 | 10 | 6 |

This example shows that both phases of the product of this invention, when allowed to separate, provide equal and excellent anti-wear performance especially when compared to an untreated fluid such as Fluid 6C from EXAMPLE 6.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A composition comprising the reaction product of a reaction mixture comprising:
   (1) at least one beta-hydroxy thioether reactant represented by the formula:

$$R\text{-}(SCH_2CH_2OH)_x \qquad I$$

wherein R represents an unsubstituted or substituted hydrocarbyl group and wherein x is a number from 1 to about 3 and which identifies the number of -SCH$_2$CH$_2$OH groups attached to R;
   (2) an amount of phosphorous-containing reactant selected from the group consisting of dihydrocarbyl hydrogen phosphite, trihydrocarbyl phosphite, and mixtures thereof, sufficient to provide at least about ten mole percent of phosphorous containing reactant based on the total moles of reactants in said reaction mixture; and
   (3) a nucleophilic reactant containing at least one reactive hydroxy group and being free from any reactive mercapto or -SCH$_2$CH$_2$OH groups;

wherein said reaction mixture is admixed in a manner and under conditions sufficient to form a one or two phase mixture comprising:
   (i) non-phosphorous containing compounds having within their structure at least one group represented by the formula:

$$\text{-S-CH}_2\text{CH}_2\text{-Q-} \qquad I'''$$

wherein Q is independently selected from the group consisting of oxygen or sulfur, said Q constituting a portion of the residue derived from: (1) the beta-hydroxy thioether reactant, (2) the hydrocarbyl portion of the organic phosphite reactant, (3) the nucleophilic reactant, and (4) mixture of (1) to (3); and wherein the remainder of Structure I''', exclusive of Q, contains residue of beta-hydroxy thioether reactant; and
   (ii) phosphorous containing compounds comprising phosphorous acid and organic phosphites having within their structures at least one group represented by the formula:

$$R\text{-SCH}_2\text{CH}_2\text{O-} \qquad I'$$

bonded directly to the phosphorous atom of the organic phosphite said R-SCH$_2$CH$_2$O— group representing a residue of beta-hydroxy thioether.

2. The composition of claim 1 wherein the nucleophilic reactant is represented by at least one of the formulas:

$$R_7\text{---}(LH)_{n'} \qquad IV$$
and
$$H\text{+}O\text{---}R_{29}\text{+}_bZ\text{+}R_{29}\text{---}O\text{+}_dH \qquad IV'$$

wherein R$_7$ represents an inertly substituted or unsubstituted hydrocarbyl group; L represents at least one member selected from the group consisting of oxy, oxyalkylene, polyoxyalkylene, and poly(oxyalkylene)thio; n' is a number of from 1 to about 3 and represents the number of -LH groups attached to R$_7$; R$_{29}$ is independently C$_2$ to about C$_4$ alkylene; Z is selected from —S—, —S—S—, O—, >NR$_{10}$ wherein R$_{10}$ is H, C$_1$ to C$_{22}$ alkyl, or monohydroxy C$_1$ to C$_{12}$ alkyl; and (b) and (d), independently, are from 1 to 3, with the proviso that the identity of R$_{29}$, b and d is selected such that the compound represented by formula IV' does not contain an -SCH$_2$CH$_2$OH group.

3. The composition of claim 1, wherein said nucleophilic reactant may be represented by at least one of the formulas:

$$R_7\text{---}(LH)_{n'} \qquad IV$$
$$H\text{+}(O\text{---}R_{29})\text{+}_bZ\text{+}(R_{20}\text{---}O)\text{+}_dH \qquad IV'$$

-continued $$R_7\text{\textemdash}[Z\text{\textemdash}(R_{29}\text{\textemdash}O)_{n'''}\text{\textemdash}H]_{n'''} \qquad IV''$$

wherein $R_7$ represents an inertly substituted or unsubstituted aliphatic hydrocarbyl group having from 6 to 22 carbons; L represents oxygen; Z is —S— or —S—S— n' is a number of from 1 to about 3 and represents the number of -(LH) groups attached to $R_7$; n'' is a number of from 2 to about 4; $R_{29}$ is $C_2$ to about $C_4$ alkylene; and n''' is a number of from about 1 to about 3 and represents the number of $[Z (R_{29}\text{-}O)_{n''} H]$ groups attached to $R_7$.

4. The composition of claim 1, wherein said nucleophilic reactant may be represented by the formula:

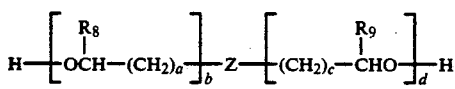

wherein $R_8$ and $R_9$, each independently, represent H or $C_1$-$C_{12}$ alkyl; Z is selected from —S—, —S—S—, —O— and >$NR_{10}$, wherein $R_{10}$ is H, $C_1$-$C_{22}$ alkyl, or monohydroxy-substituted $C_1$-$C_{12}$ alkyl; a, b, c, and d, each, independently, represents the same or different number of from about 1 to about 3 with the proviso that a+b, and c+d, are each at least 3.

5. The composition of claim 4, wherein, in said nucleophilic reactant, $R_8$ and $R_9$ are H; a and c are 1, b and d are 2; and Z is —S—.

6. The composition of claim 1, wherein said nucleophilic reactant is formed in situ and is derived from the hydrocarbyl portion of at least one of said hydrocarbyl phosphite reactants.

7. The composition of claim 1 wherein:
 (1) in structural formula I, R represents a member selected from the group consisting of: $C_1$-$C_{30}$ aliphatic hydrocarbyl; $C_6$-$C_{14}$ aromatic hydrocarbyl; mixed aromatic/aliphatic hydrocarbyl wherein the aromatic and aliphatic portions thereof are as described immediately above; -$R_1$OH or -S$R_1$OH, wherein $R_1$ is independently as described in connection with R as aliphatic, aromatic, and mixed aliphatic/aromatic;
 (2) the phosphorous-containing reactant is selected from the group consisting of organic phosphite esters having at least one of the following formulas:

$$P(OR_5)_3 \qquad II$$

wherein $R_5$, independently, represents the same or different $C_1$-$C_{30}$ straight chain aliphatic group or the group

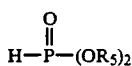

wherein $R_6$, independently, represents the same or different $C_1$-$C_{24}$ hydrocarbyl group or H; n is a number from 1 to 3; and wherein $R_5$ and $R_6$ may be inertly substituted.

8. The composition of claim 1, wherein x is 1; and R represents at least one member selected from the group consisting of $C_1$-$C_{30}$ alkyl; $C_6$-$C_{14}$ aryl; alkaryl or aralkyl wherein the alkyl and aryl portions thereof are as described immediately above; -$R_1$OH, -S$R_1$OH, or

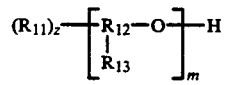

wherein, $R_1$ and $R_{11}$, independently, are as described in connection with R as alkyl, aryl, aralkyl and alkaryl immediately above; $R_{12}$ is $C_2$ to $C_3$ alkanetriyl; $R_{13}$ is H or $C_1$-$C_{18}$ aliphatic hydrocarbyl; m is a number of from 1 to 6 and represents the number of repeating oxyalkylene groups; and z is 0 or 1.

9. The composition of claim 8, wherein in said beta-hydroxy thioether R is $C_{10}$-$C_{14}$ alkyl.

10. The composition of claim 8, wherein in said beta-hydroxy thioether x is 1; R is selected from the group consisting of $C_8$ to $C_{15}$ alkyl, -$R_1$OH,

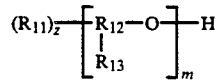

and mixtures thereof, and wherein $R_1$ is $C_8$ to $C_{15}$ alkyl; $R_{12}$ is $C_2$ alkanetriyl, $R_{13}$ is H, z is 0, and m is a number of from 1 to 3.

11. The composition of claim 8, wherein, in said phosphorous-containing reactant, each $R_5$, independently, represents $C_2$-$C_4$ alkyl, or phenyl.

12. The composition of claim 11, wherein each $R_5$ is the same.

13. The composition of any one of claims 1 to 12, wherein said admixture in step (A) comprises at least about twenty mole percent of phosphorous-containing reactant based on the total number of moles of reactants in said reaction mixture.

14. The composition of any one of claims 1 to 12, wherein said admixtures in step (A) comprises from about 20 to about 50 mole percent of phosphorous-containing reactant, based on the total number of moles of reactants in said reaction mixture.

15. A composition comprising the reaction product recovered from a top phase of a reaction product mixture prepared by a process comprising:
 (A) providing an admixture comprising:
  (1) at least one beta-hydroxy thioether reactant represented by the formula:

$$R\text{-}(SCH_2CH_2OH)_x \qquad I$$

wherein R represents an unsubstituted or substituted hydrocarbyl group, and wherein x is a number from 1 to about 3 and identifies the number of -$SCH_2CH_2OH$ groups attached to R;
  (2) an amount of phosphorous-containing reactant selected from the group consisting of dihydrocarbyl hydrogen phosphite, trihydrocarbyl phosphite, and mixtures thereof, sufficient to provide at least about ten mole percent of phosphorous containing reactant based on the total moles of reactants in said reaction mixture; and (3) a nucleophilic reactant containing at least one reactive hydroxy group and being free from any reactive mercapto or -SCH$_2$CH$_2$OH groups;

(B) heating the admixture prepared in accordance with Step (A) in a manner and under conditions sufficient to:

(1) cause the beta-hydroxy thioether to react with the components of the reaction mixture to form a product mixture comprising:

(i) non-phosphorous containing compounds having within their structure at least one group represented by the formula:

$$-S-CH_2CH_2-O- \qquad I''$$

wherein Q is independently selected from the group consisting of oxygen or sulfur; said Q constituting a portion of the residue derived from: (1) the beta-hydroxy thioether reactant, (2) the hydrocarbyl portion of the organic phosphite reactant, (3) the nucleophilic reactant, and (4) mixtures of (1) to (3); and wherein the remainder of Structure I'' exclusive of Q, contains residue of beta-hydroxy thioether reactant; and (ii) phosphorous compounds comprising phosphorous acid and organic phosphites having within their structure at least one group represented by the formula:

$$R-SCH_2CH_2O- \qquad I'$$

bonded directly to the phosphorous atom of the organic phosphite, said R-SCH$_2$CH$_2$O— group representing a residue of beta-hydroxy thioether; and (2) cause the product mixture to separate into a top phase and a bottom phase, with said top phase comprising a major amount of said non-phosphorous containing compounds and said bottom phase comprising a major amount of said phosphorous containing compounds; and (C) separating the top phase from the bottom phase.

16. The composition of claim 15 wherein the nucleophilic reactant is represented by at least one of the formulas:

$$R_7-(LH)_{n'} \qquad IV$$
and
$$H+O-R_{29}\}_bZ+R_{29}-O\}_dH \qquad IV'$$

wherein R$_7$ represents an inertly substituted or unsubstituted hydrocarbyl group; L represents at least one member selected from the group consisting of oxy, oxyalkylene, polyoxyalkylene, and poly(oxyalkylene)thio; n' is a number of from 1 to about 3 and represents the number of -LH groups attached to R$_7$; R$_{29}$ is independently C$_2$ to about C$_4$ alkylene; Z is selected from —S—, —S—S—, —O—, >NR$_{10}$ wherein R$_{10}$ is H, C$_1$ to C$_{22}$ alkyl, or monohydroxy C$_1$ to C$_{12}$ alkyl; and (b) and (d), independently, are from 1 to 3, with the proviso that the identity of R$_{29}$, b and d is selected such that the compound represented by formula IV' does not contain an -SCH$_2$CH$_2$OH group.

17. The composition of claim 1, wherein said nucleophilic reactant may be represented by at least one of the formulas:

$$R_7-(LH)_{n'} \qquad IV$$
$$H+(O-R_{29})_b Z+(R_{20}-O)_d H \qquad IV'$$
$$R_7+Z-(R_{29}-O)_{n'''}-H]_{n'''} \qquad IV''$$

wherein R$_7$ represents an inertly substituted or unsubstituted aliphatic hydrocarbyl group having from to 22 carbons; L represents oxygen; Z is —S—or —S—S—; n' is a number of from 1 to about 3 and represents the number of -LH groups attached to R$_7$; n'' is a number of from 2 to about 4; R$_{29}$ is C$_2$ to about C$_4$ alkylene; and n''' is a number of from about 1 to about and represents the number of [Z (R$_{29}$-O)$_{n'''}$-H] groups attached to R$_7$.

18. The composition of claim 15, wherein said nucleophilic reactant may be represented by the formula:

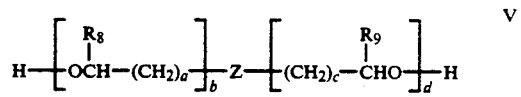

wherein R$_8$ and R$_9$, each independently, represent H or C$_1$-C$_{12}$ alkyl; Z is selected from —S—, —S—S—, —O— and NR$_{10}$, wherein R$_{10}$ is H, C$_1$-C$_{22}$ alkyl, or monohydroxy-substituted C$_1$-C$_{12}$ alkyl; a, b, c, and d, each, independently, represents the same or different number of from about 1 to about 3 with the proviso that a+b, and c+d, are each at least 3.

19. The composition of claim 1, wherein, in said nucleophilic reactant, R$_8$ and R$_9$ are H; a and c are 1, b and d are 2; and Z is —S—.

20. The composition of claim 15, wherein said nucleophilic reactant is formed in situ and is derived from the hydrocarbyl portion of at least one of said hydrocarbyl phosphite reactants.

21. The composition of claim 15 wherein:

(1) in structural formula I, R represents a member selected from the group consisting of: C$_1$-C$_{30}$ aliphatic hydrocarbyl; C$_6$-C$_{14}$ aromatic hydrocarbyl; mixed aromatic/aliphatic hydrocarbyl wherein the aromatic and aliphatic portions thereof are as described immediately above; -R$_1$OH or -SR$_1$OH, wherein R$_1$ is independently as described in connection with R as aliphatic, aromatic, and mixed aliphatic/aromatic;

(2) the phosphorous-containing reactant is selected from the group consisting of organic phosphite esters having at least one of the following formulas:

$$P(OR_5)_3 \qquad II$$

$$\overset{O}{\underset{\|}{H-P}}-(OR_5)_2 \qquad III$$

wherein R$_5$, independently, represents the same or different C$_1$-C$_{30}$ straight chain aliphatic group or the group

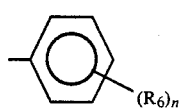

wherein R$_6$, independently, represents the same or different C$_1$-C$_{24}$ hydrocarbyl group or H; n is a number from 1 to 3; and wherein $R_5$ and $R_6$ may be inertly substituted.

22. The composition of claim 21, wherein x is 1; and R represents at least one member selected from the group consisting of $C_1$–$C_{30}$ alkyl; $C_6$–$C_{14}$ aryl; alkaryl or aralkyl wherein the alkyl and aryl portions thereof are as described immediately above; -$R_1$OH, -$SR_1$OH, or

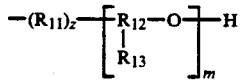

wherein, $R_1$ and $R_{11}$, independently, are as described in connection with R as alkyl, aryl, aralkyl and alkaryl immediately above; $R_{12}$ is $C_2$ to $C_3$ alkanetriyl; $R_{13}$ is H or $C_1$–$C_{18}$ aliphatic hydrocarbyl; m is a number of from 1 to 6 and represents the number of repeating oxyalkylene groups; and z is 0 or 1.

23. The composition of claim 22, wherein in said beta-hydroxy thioether R is $C_{10}$–$C_{14}$ alkyl.

24. The composition of claim 22, wherein in said beta-hydroxy thioether x is 1; R is selected from the group consisting of $C_8$ to $C_{15}$ alkyl, -$R_1$OH,

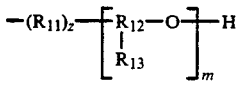

and mixtures thereof, and wherein $R_1$ is $C_8$ to $C_{15}$ alkyl; $R_{12}$ is $C_2$ alkanetriyl, $R_{13}$ is H, z is 0, and m is a number of from 1 to 3.

25. The composition of claim 22, wherein, in said phosphorous-containing reactant, each $R_5$, independently, represents $C_2$–$C_4$ alkyl, or phenyl.

26. The composition of claim 25, wherein each $R_5$ is the same.

27. The composition of any one of claims 15 to 26, wherein said admixture in step (A) comprises at least about twenty mole percent of phosphorous-containing reactant based on the total number of moles of reactants in said reaction mixture.

28. The composition of any one of claims 13 to 26, wherein said admixture in step (A) comprises from about 20 to about 50 mole percent of phosphorous-containing reactant, based on the total number of moles of reactants in said reaction mixture.

29. A composition comprising the reaction product recovered from a bottom phase of a reaction product mixture prepared by a process comprising:
   (A) providing an admixture comprising:
      (1) at least one beta-hydroxy thioether reactant represented by the formula:

R-(SCH$_2$CH$_2$OH)$_x$         I wherein R represents an unsubstituted or substituted hydrocarbyl group, and wherein x is a number from 1 to about 3 and identifies the number of -SCH$_2$CH$_2$OH groups attached to R;
      (2) an amount of phosphorous-containing reactant selected from the group consisting of dihydrocarbyl hydrogen phosphite, trihydrocarbyl phosphite, and mixtures thereof, sufficient to provide at least about ten mole percent of phosphorous containing reactant based on the total moles of reactants in said reaction mixture; and
      (3) a nucleophilic reactant containing at least one reactive hydroxy group and being free from any reactive mercapto or -SCH$_2$CH$_2$OH groups;
   (B) heating the admixture prepared in accordance with Step (A) in a manner and under conditions sufficient to:
      (1) cause the beta-hydroxy thioether to react with the components of the reaction mixture to form a product mixture comprising:
         (i) non-phosphorous containing compounds having within their structure at least one group represented by the formula:

-S—CH$_2$CH$_2$—Q—         I″ wherein Q is independently selected from the group consisting of oxygen or sulfur, said Q constituting a portion of the residue derived from: (1) the beta-hydroxy thioether reactant, (2) the hydrocarbyl portion of the organic phosphite reactant, (3) the nucleophilic reactant, and (4) mixture of (1) to (3); and wherein the remainder of Structure I″ exclusive of Q, contains residue of beta-hydroxy thioether reactant; and
         (ii) phosphorous containing compounds comprising phosphorous acid and organic phosphites having within their structures at least one group represented by the formula:

R-SCH$_2$CH$_2$O—          I′ bonded directly to the phosphorous atom of the organic phosphite, said R-SCH$_2$CH$_2$OH— group representing a residue of beta-hydroxy thioether; and
      (2) cause the product mixture to separate into a top phase and a bottom phase with said bottom phase comprising a major amount of said phosphorous containing compounds; and
   (C) separating the bottom phase from the top phase to recover the bottom phase.

30. The composition of claim 27 wherein the nucleophilic reactant is represented by at least one of the formulas:

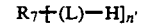         IV and

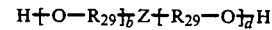         IV′ wherein $R_7$ represents an inertly substituted or unsubstituted hydrocarbyl group; L represents at least one member selected from the group consisting of oxy, oxyalkylene, polyoxyalkylene, and poly(oxyalkylene)thio; n′ is a number of from 1 to about 3 and represents the number of -LH groups attached to $R_7$; $R_{29}$ is independently $C_2$ to about $C_4$ alkylene; Z is selected from —S—, —S—S—, —O—, >$NR_{10}$ wherein $R_{10}$ is H, $C_1$ to $C_{22}$ alkyl, or monohydroxy $C_1$ to $C_{12}$ alkyl; and (b) and (d), independently, are from 1 to 3, with the proviso that the identity of $R_{29}$, b and d is selected such that the compound represented by formula IV′ does not contain an -SCH$_2$CH$_2$OH group.

31. The composition of claim 29, wherein said nucleophilic reactant may be represented by at least one of the formulas:

  IV

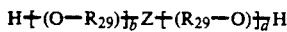  IV'

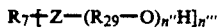  IV"

wherein $R_7$ represents an inertly substituted or unsubstituted aliphatic hydrocarbyl group having from 6 to 22 carbons; L represents oxygen; Z is —S— or —S—S—; n' is a number of from 1 to about 3 and represents the number of -LH groups attached to $R_7$; n" is a number of from 2 to about 4; $R_{29}$ is $C_2$ to about $C_4$ alkylene; and n''' is a number of from about 1 to about 3 and represents the number of $[Z\text{-}(R_{29}\text{—}O)_{n''}H]$ groups attached to $R_7$.

32. The composition of claim 29, wherein said nucleophilic reactant may be represented by the formula:

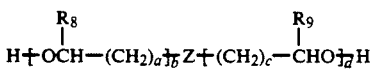  V wherein $R_8$ and $R_9$, each independently, represent H or $C_1$-$C_{12}$ alkyl; Z is selected from —S—, —S—S—, —O— and $NR_{10}$, wherein $R_{10}$ is H, $C_1$-$C_{22}$ alkyl, or monohydroxy-substituted $C_1$-$C_{12}$ alkyl; a, b, c, and d, each, independently, represents the same or different number of from about 1 to about 3 with the proviso that a+b, and c+d, are each at least 3.

33. The composition of claim 32, wherein, in said nucleophilic reactant, $R_8$ and $R_9$ are H; a and c are 1, b and d are 2; and Z is —S—.

34. The composition of claim 29, wherein said nucleophilic reactant is formed in situ and is derived from the hydrocarbyl portion of at least one of said hydrocarbyl phosphite reactants.

35. The composition of claim 29 wherein:
   (1) in structural formula I, R represents a member selected from the group consisting of: $C_1$-$C_{30}$ aliphatic hydrocarbyl; $C_6$-$C_{14}$ aromatic hydrocarbyl; mixed aromatic/aliphatic hydrocarbyl wherein the aromatic and aliphatic portions thereof are as described immediately above; -$R_1$OH or -$SR_1$OH, wherein $R_1$ is independently as described in connection with R as aliphatic, aromatic, and mixed aliphatic/aromatic;
   (2) the phosphorous-containing reactant is selected from the group consisting of organic phosphite esters having at least one of the following formulas:

  II

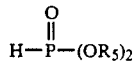  III wherein $R_5$, independently, represents the same or different $C_1$-$C_{30}$ straight chain aliphatic group or the group

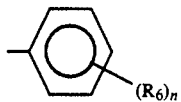  III' wherein $R_6$, independently, represents the same or different $C_1$-$C_{24}$ hydrocarbyl group or H; n is a number from 1 to 3; and wherein $R_5$ and $R_6$ may be inertly substituted.

36. The composition of claim 35, wherein x is 1; and R represents at least one member selected from the group consisting of $C_1$-$C_{30}$ alkyl; $C_6$-$C_{14}$ aryl; alkaryl or aralkyl wherein the alkyl and aryl portions thereof are as described immediately above; -$R_1$OH, -$SR_1$OH, or

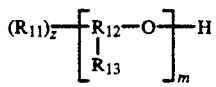

wherein, $R_1$ and $R_{11}$, independently, are as described in connection with R as alkyl, aryl, aralkyl and alkaryl immediately above; $R_{12}$ is $C_2$ to $C_3$ alkanetriyl; $R_{13}$ is H or $C_1$-$C_{18}$ aliphatic hydrocarbyl; m is a number of from 1 to 6 and represents the number of repeating oxyalkylene groups; and z is 0 or 1.

37. The composition of claim 36, wherein in said beta-hydroxy thioether, R is $C_{10}$-$C_{14}$ alkyl.

38. The composition of claim 36, wherein in said beta-hydroxy thioether, x is 1; R is selected from the group consisting of $C_8$ to $C_{15}$ alkyl, -$R_1$OH,

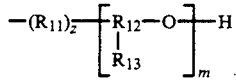

and mixtures thereof, and wherein $R_1$ is $C_8$ to $C_{15}$ alkyl; $R_{12}$ is $C_2$ alkanetriyl, $R_{13}$ is H, z is 0, and m is a number of from 1 to 3.

39. The composition of claim 36, wherein, in said phosphorous-containing reactant, each $R_5$, independently, represents $C_2$-$C_4$ alkyl, or phenyl.

40. The composition of claim 39, wherein each $R_5$ is the same.

41. The composition of any one of claims 29 to 40 wherein said admixture in step (A) comprises at least about twenty mole percent of phosphorous-containing reactant based on the total number of moles of reactants in said reaction mixture.

42. The composition of any one of claims 29 to 40 wherein said admixture in step (A) comprises from least about 20 to about 50 mole percent of phosphorous-containing reactant, based on the total number of moles of reactants in said reaction mixture.

43. A lubricating oil composition adaptable for use as an automatic transmission fluid which comprises mineral oil and an amount of an additive mixture effective to impart at least one of the properties of anti-wear and anti-oxidation to said fluid relative to the absence of said additive mixture, said additive mixture comprising the phosphorous- and sulfur-containing reaction products prepared by reacting in admixture:
   (1) at least one beta-hydroxy thioether reactant represented by the formula:

R-(SCH$_2$CH$_2$OH)$_x$  I wherein R represents an unsubstituted or substituted hydrocarbyl group, and wherein x is a number of from 1 to about 3 and identifies the number of -SCH$_2$CH$_2$OH groups attached to R;

(2) an amount of phosphorous-containing reactant selected from the group consisting of dihydrocarbyl hydrogen phosphite, trihydrocarbyl phosphite, and mixtures thereof, sufficient to provide at least about ten mole percent of phosphorous containing reactant based on the total moles of reactants in said reaction mixture; and (3) a nucleophilic reactant containing at least one reactive hydroxy group and being free from any reactive mercapto or -SCH$_2$CH$_2$OH groups;

wherein said reaction mixture is admixed in a manner and under conditions sufficient to form a one or two phase mixture comprising:

(i) non-phosphorous containing compounds having within their structure at least one group represented by the formula:

-S—CH$_2$CH$_2$—Q—  I'' wherein Q is independently selected from the group consisting of oxygen or sulfur, said Q constituting a portion of the residue derived from: (1) the beta-hydroxy thioether reactant, (2) the hydrocarbyl portion of the organic phosphite reactant, (3) the nucleophilic reactant, and (4) mixture of (1) to (3); and wherein the remainder of Structure I'' exclusive of Q, contains residue of beta-hydroxy thioether reactant; and;

(ii) phosphorous containing compounds comprising phosphorous acid and organic phosphites having within their structures at least one group represented by the formula:

R-SCH$_2$CH$_2$O—  I' bonded directly to the phosphorous atom of the organic phosphite said R-SCH$_2$CH$_2$O— group representing a residue of beta-hydroxy thioether.

44. The composition of claim 43 wherein the nucleophilic reactant is represented by at least one of the formulas:

R$_7$—(LH)$_{n'}$  IV
and
H$+$O—R$_{29}$$\}_b$Z$+$R$_{29}$—O$\}_d$H  IV' wherein R$_7$ represents an substituted or inertly substituted hydrocarbyl group; L represents at least one member selected from the group consisting of oxy, oxy-alkylene, polyoxyalkylene, and poly(oxyalkylene)thio; n' is a number of from 1 to about 3 and represents the number of -LH groups attached to R$_7$; R$_{29}$ is independently C$_2$ to about C$_4$ alkylene; Z is selected from —S—, —S—S—, —O—, >NR$_{10}$ wherein R$_{10}$ is H, C$_1$ to C$_{22}$ alkyl, or monohydroxy C$_1$ to C$_{12}$ alkyl; and (b) and (d), independently, are from 1 to 3, with the proviso that the identity of R$_{29}$, b and d is selected such that the compound represented by formula IV' does not contain an -SCH$_2$CH$_2$OH group.

45. The composition of claim 43, wherein said nucleophilic reactant may be represented by at least one of the formulas:

R$_7$—(LH)$_{n'}$  IV
H$+$(O—R$_{29}$)$_b$Z$+$(R$_{29}$—O)$_d$H  IV'
R$_7$$+$Z—(R$_{29}$—O)$_{n''}$H]$_{n'''}$  IV'' wherein R$_7$, represents an inertly substituted or unsubstituted aliphatic hydrocarbyl group having from 6 to 22 carbons; L represents oxygen; Z is —S— or —S—S—; n' is a number of from 1 to about 3 and represents the number of -LH groups attached to R$_7$; n'' is a number of from 2 to about 4; R$_{29}$ is C$_2$ to about C$_4$ alkylene; and n''' is a number of from about 1 to about 3 and represents the number of [Z-(R$_{29}$—O)$_{n''}$H] groups attached to R$_7$.

46. The composition of claim 43, wherein said nucleophilic reactant may be represented by the formula:

$$H\!-\!\!\left[\!-\!OCH\!\!\!\underset{R_8}{|}\!\!\!-(CH_2)_a\!\right]_{\!b}\!\!Z\!+\!(CH_2)_c\!-\!CHO\!\!\!\underset{R_9}{|}\!\!\!-\!\right]_{\!d}\!\!\!-\!H \quad V$$

wherein R$_8$ and R$_9$, each independently, represent H or C$_1$-C$_{12}$ alkyl; Z is selected from —S—, —S—S—, —O— and NR$_{10}$, wherein R$_{10}$ is H, C$_1$-C$_{22}$ alkyl, or monohydroxy-substituted C$_1$-C$_{12}$ alkyl; a, b, c, and d, each, independently, represents the same or different number of from about 1 to about 3 with the proviso that a+b, and c+d, are each at least 3.

47. The composition of claim 46, wherein, in said nucleophilic reactant, R$_8$ and R$_9$ are H; a and c are 1, b and d are 2; and Z is —S—.

48. The composition of claim 43, wherein said nucleophilic reactant is formed in situ and is derived from the hydrocarbyl portion of at least one of said hydrocarbyl phosphite reactants.

49. The composition of claim 43 wherein:

(1) in structural formula I, R represents a member selected from the group consisting of: C$_1$-C$_{30}$ aliphatic hydrocarbyl; C$_6$-C$_{14}$ aromatic hydrocarbyl; mixed aromatic/aliphatic hydrocarbyl wherein the aromatic and aliphatic portions thereof are as described immediately above; -R$_1$OH or -SR$_1$OH, wherein R$_1$ is independently as described in connection with R as aliphatic, aromatic, and mixed aliphatic/aromatic;

(2) the phosphorous-containing reactant is selected from the group consisting of organic phosphite esters having at least one of the following formulas:

R(OR$_5$)$_3$  II $$\underset{H-P-(OR_5)_2}{\overset{O}{\|}} \quad III$$

wherein R$_5$, independently, represents the same or different C$_1$-C$_{30}$ straight chain aliphatic group or the group

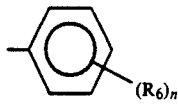

wherein $R_6$, independently, represents the same or different $C_1$-$C_{24}$ hydrocarbyl group or H; n is a number from 1 to 3; and wherein $R_5$ and $R_6$ may be inertly substituted.

50. The composition of claim 49, wherein x is 1; and R represents at least one member selected from the group consisting of $C_1$-$C_{30}$ alkyl; $C_6$-$C_{14}$ aryl; alkaryl or aralkyl wherein the alkyl and aryl portions thereof are as described immediately above; -$R_1$OH, -$SR_1$OH, or

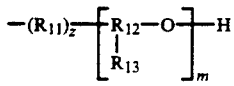

wherein, $R_1$ and $R_{11}$, independently, are as described in connection with R as alkyl, aryl, aralkyl and alkaryl immediately above; $R_{12}$ is $C_2$ to $C_3$ alkanetriyl; $R_{13}$ is H or $C_1$-$C_{18}$ aliphatic hydrocarbyl; m is a number of from 1 to 6 and represents the number of repeating oxyalkylene groups; and z is 0 or 1.

51. The composition of claim 50, wherein in said beta-hydroxy thioether R is $C_{10}$-$C_{14}$ alkyl.

52. The composition of claim 50, wherein in said beta-hydroxy thioether x is 1; R is selected from the group consisting of $C_8$ to $C_{15}$ alkyl, -$R_1$OH

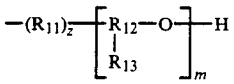

and mixtures thereof, and wherein $R_1$ is $C_8$ to $C_{15}$ alkyl; $R_{12}$ is $C_2$ alkanetriyl, $R_{13}$ is H, z is 0, and m is a number of from 1 to 3.

53. The composition of claim 51, wherein, in said phosphorous-containing reactant, each $R_5$, independently, represents $C_2$-$C_4$ alkyl, or phenyl.

54. The composition of claim 53, wherein each $R_5$ is the same.

55. The composition according to any one of claims 43-54 wherein said additive mixture is present in an amount of from about 0.01 to about 25 weight percent.

56. A lubricating oil composition adaptable for use as an automatic transmission fluid which comprises mineral oil and an amount of an additive mixture effective to impart at least one of the properties of anti-wear and anti-oxidation to said fluid relative to the absence of said additive mixture, said additive mixture comprising a top phase mixture of non-phosphorous-containing compounds as set forth in any one of claims 15 to 28.

57. A lubricating oil composition adaptable for use as an automatic transmission fluid which comprises mineral oil and an amount of an additive mixture effective to impart at least one of the properties of anti-wear and anti-oxidation to said fluid relative to the absence of said additive mixture, said additive mixture comprising a bottom phase mixture of phosphorous-containing compounds as set forth in any one of claims 29 to 42.

58. The composition according to any one of claims 56 to 57 wherein said additive mixture is present in an amount of from about 0.01 to about 25 weight percent.

59. An additive concentrate comprising a base oil in an amount up to about 75 wt. % and from about 25 wt. % up to about 100 wt. % of said concentrate of an additive mixture comprised of the phosphorous- and sulfur-containing reaction products formed by reacting in admixture:

(1) at least one beta-hydroxy thioether reactant represented by the formula:

$$R\text{-}(SCH_2CH_2OH)_x \qquad \text{I}$$

wherein R represents an unsubstituted or inertly substituted hydrocarbyl group having present in its structure one or more hydroxy, oxy, thio, oxalkylene and oxyalkylenethio groups and wherein x is a number from 1 to 3 and which identifies the number of -$SCH_2CH_2OH$ groups attached to R;

(2) an amount of phosphorous-containing reactant selected from the group consisting of dihydrocarbyl hydrogen phosphite, trihydrocarbyl phosphite, and mixtures thereof, sufficient to provide at least about ten mole percent of phosphorous containing reactant based on the total moles of reactants in said reaction mixture; and (3) a nucleophilic reactant containing at least one reactive hydroxy group and being free from any reactive mercapto or -$SCH_2CH_2OH$ groups;

wherein said reaction mixture is admixed in a manner and under conditions sufficient to form either a one or two phase product mixture comprising:

(i) non-phosphorous containing compounds having within their structure at least one group represented by the formula:

$$\text{-S-CH}_2CH_2\text{—Q-} \qquad \text{I''}$$

wherein Q is independently selected from the group consisting of oxygen or sulfur, said Q constituting a portion of the residue derived from: (1) beta-hydroxy thioether reactant, (2) the hydrocarbyl portion of the organic phosphite reactant, (3) the nucleophilic reactant, and (4) mixtures of (1) to (3); and wherein the remainder of Structure I'' exclusive of Q, contains residue of beta-hydroxy thioether reactant; and (ii) phosphorous-containing compounds comprising phosphorous acid and organic phosphites having within their structure at least one group represented by the formula:

$$R\text{-SCH}_2CH_2O\text{—} \qquad \text{I'}$$

bonded directly to the phosphorous atom of the organic phosphite said R-$SCH_2CH_2O$— group representing a residue of beta-hydroxy thioether.

60. The concentrate of claim 59 wherein the nucleophilic reactant is represented by at least one of the formulas:

$$R_7\text{—(LH)}_{n'} \qquad \text{IV}$$

and $$H\text{—}(O\text{—}R_{29})_{\overline{b}}Z\text{—}(R_{29}\text{—}O)_{\overline{d}}H \qquad \text{IV'}$$

wherein R₇ represents an inertly substituted or unsubstituted hydrocarbyl group; L represents at least one member selected from the group consisting of oxy, oxyalkylene, polyoxyalkylene, and poly(oxyalkylene)thio; n' is a number of from 1 to about 3 and represents the number of -LH groups attached to R₇; R₂₉ is independently C₂ to about C₄ alkylene; Z is selected from —S—, —S—S—, —O—, >NR₁₀ wherein R₁₀ is H, C₁ to C₂₂ alkyl, or monohydroxy C₁ to C₁₂ alkyl; and (b) and (d), independently, are from 1 to 3, with the proviso that the identity of R₂₉, b and d is selected such that the compound represented by formula IV' does not contain an -SCH₂CH₂OH group.

61. The concentrate of claim 59, wherein said nucleophilic reactant may be represented by at least one of the formulas:

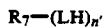    IV

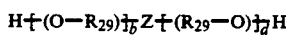    IV'

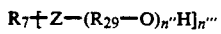    IV'' wherein R₇ represents an inertly substituted or unsubstituted aliphatic hydrocarbyl group having from 6 to 22 carbons; L represents oxygen; Z is —S— or —S—S—; n' is a number of from 1 to about 3 and represents the number of -LH groups attached to R₇; n'' is a number of from 2 to about 4; R₂₉ is C₂ to about C₄ alkylene; and n''' is a number of from about 1 to about 3 and represents the number of [Z-(R₂₉—O)ₙ''H] groups attached to R₇.

62. The concentrate of claim 59, wherein said nucleophilic reactant may be represented by the formula:

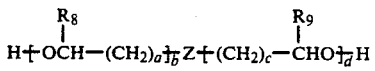    V wherein R₈ and R₉, each independently, represent H or C₁-C₁₂ alkyl; Z is selected from —S—, —S—S—, —O— and NR₁₀, wherein R₁₀ is H, C₁-C₂₂ alkyl, or monohydroxy-substituted C₁-C₁₂ alkyl; a, b, c, and d, each, independently, represents the same or different number of from about 1 to about 3 with the proviso that a+b, and c+d, are each at least 3.

63. The concentrate of claim 62, wherein, in said nucleophilic reactant, R₈ and R₉ are H; a and c are 1, b and d are 2; and Z is —S—.

64. The concentrate of claim 59, wherein said nucleophilic reactant is formed in situ and is derived from the hydrocarbyl portion of at least one of said hydrocarbyl phosphite reactants.

65. The concentrate of any of claims 60 to 64 wherein said admixture comprises at least twenty mole percent of phosphorous-containing reactant, based on the total number of moles of reactants in said admixture.

66. The concentrate of claim 59 wherein:
(1) in structural formula I, R represents a member selected from the group consisting of: C₁-C₃₀ aliphatic hydrocarbyl; C₆-C₁₄ aromatic hydrocarbyl; mixed aromatic/aliphatic hydrocarbyl wherein the aromatic and aliphatic portions thereof are as described immediately above; -R₁OH or -SR₁OH, wherein R₁ is independently as described in connection with R as aliphatic, aromatic, and mixed aliphatic/aromatic;
(2) the phosphorous-containing reactant is selected from the group consisting of organic phosphite esters having at least one of the following formulas:

    II

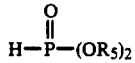    III wherein R₅, independently, represents the same or different C₁-C₃₀ straight chain aliphatic group or the group

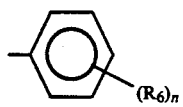    III' wherein R₆, independently, represents the same or different C₁-C₂₄ hydrocarbyl group or H; n is a number from 1 to 3; and wherein R₅ and R₆ may be inertly substituted.

67. The concentrate of claim 66, wherein x is 1; and R represents at least one member selected from the group consisting of C₁-C₃₀ alkyl; C₆-C₁₄ aryl; alkaryl or aralkyl wherein the alkyl and aryl portions thereof are as described immediately above; -R₁OH, -SR₁OH, or

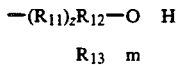

wherein, R₁ and R₁₁, independently, are as described in connection with R as alkyl, aryl, aralkyl and alkaryl immediately above; R₁₂ is C₂ to C₃ alkanetriyl; R₁₃ is H or C₁-C₁₈ aliphatic hydrocarbyl; m is a number of from 1 to 6 and represents the number of repeating oxyalkylene groups; and z is 0 or 1.

68. The concentrate of claim 67, wherein in said beta-hydroxy thioether R is C₁₀-C₁₄ alkyl.

69. The concentrate of claim 67, wherein in said beta-hydroxy thioether x is 1; R is selected from the group consisting of C₈ to C₁₅ alkyl, -R₁OH,

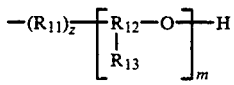

and mixtures thereof, and wherein R₁ is C₈ to C₁₅ alkyl; R₁₂ is C₂ alkanetriyl, R₁₃ is H, z is 0, and m is a number of from 1 to 3.

70. The concentrate of claim 67, wherein, in said phosphorous-containing reactant, each R₅, independently, represents C₂-C₄ alkyl, or phenyl.

71. The concentrate of claim 70, wherein each R₅ is the same.

72. The concentrate of any of claims 59 to 71 wherein said admixture from comprises at least about 20 to about 50 mole percent of phosphorous-containing reactant, based on the total number of moles of reactants in said admixture.

73. An additive concentrate comprising a base oil in an amount up to about 75 wt. % and from about 25 wt. % up to about 100 wt. % of said concentrate of an additive mixture comprising the mixture of non-phosphorous-containing compounds recovered as the top phase according to any one of claims 24 to 28.

74. An additive concentrate comprising a base oil in an amount up to about 75 wt. % and from about 25 wt. % up to about 100 wt. % of said concentrate of an additive mixture comprising the mixture of phosphorous-containing compounds recovered as the bottom phase according to any one of claims 29 and 42.

75. A process for improving at least one of the anti-wear and anti-oxidation properties of an oleaginous composition which comprises admixing a phosphorous- and sulfur-containing additive with an oleaginous lubricating oil, said phosphorous- and sulfur-containing additive having been prepared by reacting in admixtures:
(1) at least one beta-hydroxy thioether reactant represented by the formula:

$$R\text{-}(SCH_2CH_2OH)_x \qquad \qquad I$$

wherein R represents an unsubstituted or substituted hydrocarbyl group, and wherein x is a number from 1 to about 3 and which identifies the number of -SCH$_2$CH$_2$OH groups attached to R;
(2) an amount of phosphorous-containing reactant selected from the group consisting of dihydrocarbyl hydrogen phosphite, trihydrocarbyl phosphite, and mixtures thereof, sufficient to provide at least about ten mole percent of phosphorous containing reactant based on the total moles of reactants in said reaction mixture; and
(3) a nucleophilic reactant containing at least one reactive hydroxy group and being free from any reactive mercapto or -SCH$_2$CH$_2$OH groups;

wherein said reaction mixture is admixed in a manner and under conditions sufficient to form a one or two phase product mixture comprising:
(i) non-phosphorous containing compounds having within their structure at least one group represented by the formula:

$$\text{-S}\text{—}CH_2CH_2\text{—}Q\text{-} \qquad \qquad I''$$

wherein Q is independently selected from the group consisting of oxygen or sulfur, said Q constituting a portion of the residue derived from: (1) beta-hydroxy thioether reactant, (2) the hydrocarbyl portion of the organic phosphite reactant, (3) the nucleophilic reactant, and (4) mixtures of (1) to (3); and wherein the remainder of Structure I'' exclusive of Q, contains residue of beta-hydroxy thioether reactant; and
(ii) phosphorous containing compounds comprising phosphorous acid and organic phosphites having within their structure at least one group represented by the formula:

$$R\text{-}SCH_2CH_2O\text{—} \qquad \qquad I'$$

bonded directly to the phosphorous atom of the organic phosphite, said R-SCH$_2$CH$_2$O— group representing a residue of beta-hydroxy thioether.

76. The process of claim 75 wherein the nucleophilic reactant is represented by at least one of the formulas:

$$R_7\text{—}(LH)_{n'} \qquad \qquad IV$$

and

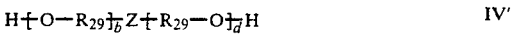  IV' wherein R$_7$ represents an inertly substituted or unsubstituted hydrocarbyl group; L represents at least one member selected from the group consisting of oxy, oxyalkylene, polyoxyalkylene, and poly(oxyalkylene)thio; n' is a number of from 1 to about 3 and represents the number of -LH groups attached to R$_7$; R$_{29}$ is independently C$_2$ to about C$_4$ alkylene; Z is selected from —S—, —S—S—, —O—, >NR$_{10}$ wherein R$_{10}$ is H, C$_1$ to C$_{22}$ alkyl, or monohydroxy C$_1$ to C$_{12}$ alkyl; and (b) and (d), independently, are from 1 to 3, with the proviso that the identity of R$_{29}$, b and d is selected such that the compound represented by formula IV' does not contain an -SCH$_2$CH$_2$OH group.

77. The process of claim 75, wherein said nucleophilic reactant may be represented by at least one of the formulas:

$$R_7\text{—}(LH)_{n'} \qquad \qquad IV$$

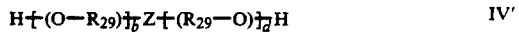  IV'

  IV'' wherein R$_7$ represents an inertly substituted or unsubstituted aliphatic hydrocarbyl group having from 6 to 22 carbons; L represents oxygen; Z is —S—, —S—S—; n' is a number of from 1 to about 3 and represents the number of -LH groups attached to R$_7$; n'' is a number of from 2 to about 4; R$_{29}$ is C$_2$ to about C$_4$ alkylene; and n''' is a number of from about 1 to about 3 and represents the number of [Z-(R$_{29}$—O)$_{n''}$H] groups attached to R$_7$.

78. The process of claim 75, wherein said nucleophilic reactant may be represented by the formula:

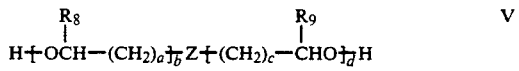  V wherein R$_8$ and R$_9$, each independently, represent H or C$_1$-C$_{12}$ alkyl; Z is selected from —S—, —S—S—, —O— and >NR$_{10}$, wherein R$_{10}$ is H, C$_1$-C$_{22}$ alkyl, or monohydroxy-substituted C$_1$-C$_{12}$ alkyl; a b, c, and d, each, independently, represents the same or different number of from about 1 to about 3 with the proviso that a+b, and c+d, are each at least 3.

79. The process of claim 78, wherein, in said nucleophilic reactant, R$_8$ and R$_9$ are H; a and c are 1, b and d are 2; and Z i —S—.

80. The process of claim 75, wherein said nucleophilic reactant is formed in situ and is derived from the hydrocarbyl portion of at least one of said hydrocarbyl phosphite reactants.

81. The process of claim 75 wherein:
(1) in structural formula I, R represents a member selected from the group consisting of: C$_1$-C$_{30}$ aliphatic hydrocarbyl; C$_6$-C$_{14}$ aromatic hydrocarbyl; mixed aromatic/aliphatic hydrocarbyl wherein the aromatic and aliphatic portions thereof are as described immediately above; -R$_1$OH or -SR$_1$OH, wherein R$_1$ is independently as described in connection with R as aliphatic, aromatic, and mixed aliphatic/aromatic;
(2) the phosphorous-containing reactant is selected from the group consisting of organic phosphite esters having at least one of the following formulas:

$$P(OR_5)_3 \qquad \qquad II$$

-continued

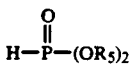   III wherein $R_5$, independently, represents the same or different $C_1$-$C_{30}$ straight chain aliphatic group or the group

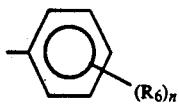   III' wherein $R_6$, independently, represents the same or different $C_1$-$C_{24}$ hydrocarbyl group or H; n is a number from 1 to 3; and wherein $R_5$ and $R_6$ may be inertly substituted.

82. The process of claim 81, wherein x is 1; and R represents at least one member selected from the group consisting of $C_1$-$C_{30}$ alkyl; $C_6$-$C_{14}$ aryl; alkaryl or aralkyl wherein the alkyl and aryl portions thereof are as described immediately above; $-R_1OH$, $-SR_1OH$, or

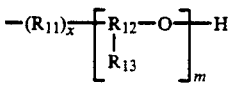

wherein, $R_1$ and $R_{11}$, independently, are as described in connection with R as alkyl, aryl, aralkyl and alkaryl immediately above; $R_{12}$ is $C_2$ to $C_3$ alkanetriyl; $R_{13}$ is H or $C_1$-$C_{18}$ aliphatic hydrocarbyl; m is a number of from 1 to 6 and represents the number of repeating oxyalkylene groups; and z is 0 or 1.

83. The process of claim 82, wherein in said beta-hydroxy thioether R is $C_{10}$-$C_{14}$ alkyl.

84. The process of claim 82, wherein in said beta-hydroxy thioether x is 1; R is selected from the group consisting of $C_8$ to $C_{15}$ alkyl, $-R_1OH$,

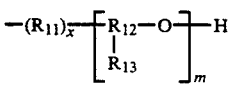

and mixtures thereof, and wherein $R_1$ is $C_8$ to $C_{15}$ alkyl; $R_{12}$ is $C_2$ alkanetriyl, $R_{13}$ is H, z is 0, and m is a number of from 1 to 3.

85. The process of claim 82, wherein, in said phosphorous-containing reactant, each $R_5$, independently, represents $C_2$-$C_4$ alkyl, or phenyl.

86. The process of claim 85, wherein each $R_5$ is the same.

87. The process of any one of claims 75 to 86 wherein said admixture comprises an amount of about twenty mole percent of phosphorous-containing reactant in said admixture.

88. The process of any of claims 75 to 86 wherein said admixture comprises an amount of from about 20 to about 50 mole percent of phosphorous-containing reactant in said admixture.

89. The process of any one of claim 75 to 86, wherein the oleaginous composition is a lubricating oil.

90. The process of claim 89, wherein the lubricating oil composition is a power transmission fluid.

91. The process of claim 90, wherein the power transmission fluid composition is an automatic transmission fluid.

92. The process according to any one of the claims 75 to 85 wherein said oleaginous composition comprises 0.01 to about 25 weight percent of said phosphorous- and sulfur-containing additive.

93. A process for improving at least one of the anti-wear and anti-oxidation properties of an oleaginous composition which comprises admixing a sulfur-containing additive with an oleaginous material selected from the group consisting of lubricating oils, said sulfur-containing additive comprising a mixture of compounds which have been recovered from the top phase of a reaction product mixture prepared by a process comprising:

(A) providing an admixture comprising:
  (1) at least one beta-hydroxy thioether reactant represented by the formula:

$R\text{-}(SCH_2CH_2OH)_x$   I wherein R represents an unsubstituted or substituted hydrocarbyl group, and wherein x is a number from 1 to about 3 and identifies the number of $-SCH_2CH_2OH$ groups attached to R;
  (2) an amount of phosphorous-containing reactant selected from the group consisting of dihydrocarbyl hydrogen phosphite, trihydrocarbyl phosphite, and mixtures thereof, sufficient to provide at least about ten mole percent of phosphorous containing reactant based on the total moles of reactants in said reaction mixture; and
  (3) a nucleophilic reactant containing at least one reactive hydroxy group and being free from any reactive mercapto or $-SCH_2CH_2OH$ groups;
(B) heating the admixture prepared in accordance with Step (A) in a manner and under conditions sufficient to:
  (1) cause the beta-hydroxy thioether to react with the components of the reaction mixture to form a product mixture comprising (i) non-phosphorous containing compounds having within their structure at least one group represented by the formula:

$-S\text{---}CH_2CH_2\text{---}Q-$   I'' wherein Q is independently selected from the group consisting of oxygen or sulfur, said Q constituting a portion of the residue derived from: (1) beta-hydroxy thioether reactant, (2) the hydrocarbyl portion of organic phosphite reactant, (3) the nucleophilic reactant, and (4) mixtures of (1) to (3); and wherein the remainder of Structure I'', exclusive of Q, contains residue of beta-hydroxy thioether reactant; and (ii) phosphorous compounds comprising phosphorous acid and organic phosphites having within their structure at least one group represented by the formula:

$R\text{-}SCH_2CH_2O-$   I' bonded directly to the phosphorous atom of the organic phosphite, said $R\text{-}SCH_2CH_2O-$ group representing a residue of beta-hydroxy thioether; and (2) cause the product mixture to separate into a top phase and a bottom phase, with said top phase comprising a major amount of said non-phosphorous containing compounds and said bottom phase comprising a major amount of said phosphorous containing compounds; and (C) separating the top phase from the bottom phase.

94. The process of claim 93 wherein the nucleophilic reactant is represented by at least one of the formulas:

$$R_7-(LH)_{n'} \quad \text{IV}$$

and $$H\!+\!O\!-\!R_{29}\!\}_{\overline{b}}Z\!+\!R_{29}\!-\!O\!\}_{\overline{d}}H \quad \text{IV}'$$

wherein $R_7$ represents an inertly substituted or unsubstituted hydrocarbyl group; L represents at least one member selected from the group consisting of oxy, oxyalkylene, polyoxyalkylene, and poly(oxyalkylene)thio; n' is a number of from 1 to about 3 and represents the number of -LH groups attached to $R_7$; $R_{29}$ is independently $C_2$ to about $C_4$ alkylene; Z is selected from —S—, —S—S—, —O—, >$NR_{10}$ wherein $R_{10}$ is H, $C_1$ to $C_{22}$ alkyl, or monohydroxy $C_1$ to $C_{12}$ alkyl; and (b) and (d), independently, are from 1 to 3, with the proviso that the identity of $R_{29}$, b and d is selected such that the compound represented by formula IV' does not contain an -SCH$_2$CH$_2$OH group.

95. The process of claim 93, wherein said nucleophilic reactant may be represented by at least one of the formulas:

$$R_7(LH)_{n'} \quad \text{IV}$$

$$H\!+\!(O\!-\!R_{29})\!\}_{\overline{b}}Z\!+\!(R_{29}\!-\!O)\!\}_{\overline{d}}H \quad \text{IV}'$$

$$R_7\!+\!Z\!-\!(R_{29}\!-\!O)_{n''}H]_{n'''} \quad \text{IV}''$$

wherein $R_7$ represents an inertly substituted or unsubstituted aliphatic hydrocarbyl group having from 6 to 22 carbons; L represents oxygen; Z is —S—, —S—S—; n' is a number of from 1 to about 3 and represents the number of -LH groups attached to $R_7$; n'' is a number of from 2 to 4; $R_{29}$ is $C_2$ to about $C_4$ alkylene; and n''' is a number of from about 1 to about 3 and represents the number of [Z-($R_{29}$—O)$_{n''}$H] groups attached to $R_7$.

96. The process of claim 93, wherein said nucleophilic reactant may be represented by the formula:

$$\overset{R_8}{\underset{|}{H\!+\!OCH\!-\!(CH_2)_a\!\}_{\overline{b}}Z\!+\!(CH_2)_c\!-\!\underset{|}{\overset{R_9}{CHO}}\!\}_{\overline{d}}H}} \quad \text{V}$$

wherein $R_8$ and $R_9$, each independently, represent H or $C_1$-$C_{12}$ alkyl; Z is selected from —S—, —S—S—, —O— and >$NR_{10}$, wherein $R_{10}$ is H, $C_1$-$C_{22}$ alkyl, or monohydroxy-substituted $C_1$-$C_{12}$ alkyl; a, b, c, and c, each, independently, represents the same or different number of from about 1 to about 3 with the proviso that a+b, and c+d, are each at least 3.

97. The process of claim 96, wherein, in said nucleophilic reactant, $R_8$ and $R_9$ are H; a and c are 1, b and d are 2; and Z is —S—.

98. The process of claim 93, wherein said nucleophilic reactant is formed in situ and is derived from the hydrocarbyl portion of at least one of said hydrocarbyl phosphite reactants.

99. The process of claim 93 wherein:
(1) in structural formula I, R represents a member selected from the group consisting of: $C_1$-$C_{30}$ aliphatic hydrocarbyl; $C_6$-$C_{14}$ aromatic hydrocarbyl; mixed aromatic/aliphatic hydrocarbyl wherein the aromatic and aliphatic portions thereof are as described immediately above; -$R_1$OH or -$SR_1$OH, wherein $R_1$ is independently as described in connection with R as aliphatic, aromatic, and mixed aliphatic/aromatic;
(2) the phosphorous-containing reactant is selected from the group consisting of organic phosphite esters having at least one of the following formulas:

$$P(OR_5)_3 \quad \text{II}$$

$$\overset{O}{\underset{\|}{H\!-\!P\!-\!(OR_5)_2}} \quad \text{III}$$

wherein $R_5$, independently, represents the same or different $C_1$-$C_{30}$ straight chain aliphatic group or the group

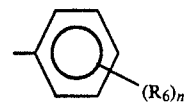

$\text{III}'$ wherein $R_6$, independently, represents the same or different $C_1$-$C_{24}$ hydrocarbyl group or H; n is a number from 1 to 3; and wherein $R_5$ and $R_6$ may be inertly substituted.

100. The process of claim 99, wherein x is 1; and R represents at least one member selected from the group consisting of $C_1$-$C_{30}$ alkyl; $C_6$-$C_{14}$ aryl; alkaryl or aralkyl wherein the alkyl and aryl portions thereof are as described immediately above; -$R_1$OH, -$SR_1$OH, or

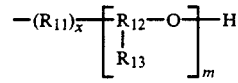

wherein: $R_1$ and $R_{11}$, independently, are as described in connection with R as alkyl, aryl, aralkyl and alkaryl immediately above; $R_{12}$ is $C_2$ to $C_3$ alkanetriyl; $R_{13}$ is H or $C_1$-$C_{18}$ aliphatic hydrocarbyl; m is a number of from 1 to 6 and represents the number of repeating oxyalkylene groups; and z is 0 or 1.

101. The process of claim 100, wherein in said beta-hydroxy thioether R is $C_{10}$-$C_{14}$ alkyl.

102. The process of claim 100, wherein in said beta-hydroxy thioether x is 1; R is selected from the group consisting of $C_8$ to $C_{15}$ alkyl, -$R_1$OH,

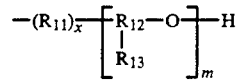

and mixtures thereof, and wherein $R_1$ is $C_8$ to $C_{15}$ alkyl; $R_{12}$ is $C_2$ alkanetriyl, $R_{13}$ is H, z is 0, and m is a number of from 1 to 3.

103. The process of claim 100, wherein, in said phosphorous-containing reactant, each $R_5$, independently, represents $C_2$-$C_4$ alkyl, or phenyl.

104. The process of claim 103, wherein each $R_5$ is the same.

105. The process of any one of claims 93 to 104, wherein said admixture in step (A) comprises at least about twenty mole percent of phosphorous-containing reactant, based on the total number of moles of reactants in the reaction mixture.

106. The process of any one of claims 93 to 104, wherein the oleaginous composition is a lubricating oil.

107. The process of claim 106, wherein the lubricating oil composition is a power transmission fluid.

108. The process of claim 107, wherein the power transmission fluid composition is an automatic transmission fluid.

109. The process according to any one of claims 93 to 104 wherein said oleagnious composition comprises from about 0.01 to about 25 weight percent of said sulfur-containing additive.

110. A process for improving at least one of the anti-wear and anti-oxidation properties of an oleaginous composition which comprises admixing a sulfur-containing additive with an oleaginous lubricating oil, said phosphorous-containing additive comprising a mixture of compounds which have been recovered from the bottom phase of a reaction product prepared by a process comprising:

(A) providing an admixture comprising:
(1) at least one beta-hydroxy thioether reactant represented by the formula:

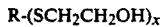

$$R\text{-}(SCH_2CH_2OH)_x \qquad \qquad I$$

wherein R represents an unsubstituted or substituted hydrocarbyl group, and wherein x is a number from 1 to about 3 and identifies the number of $-SCH_2CH_2OH$ groups attached to R;

(2) an amount of phosphorous-containing reactant selected from the group consisting of dihydrocarbyl hydrogen phosphite, trihydrocarbyl phosphite, and mixtures thereof, sufficient to provide at least about ten mole percent of phosphorous containing reactant based on the total moles of reactants in said reaction mixture; and (3) a nucleophilic reactant containing at least one reactive hydroxy group and being free from any reactive mercapto or $-SCH_2CH_2OH$ groups;

(B) heating the admixture prepared in accordance with Step (A) in a manner and under conditions sufficient to:

(1) cause the beta-hydroxy thioether to react with the components of the reaction mixture to form a product mixture comprising:

(i) non-phosphorous containing compounds having within their structure at least one group represented by the formula:

$$\text{-}S\text{--}CH_2CH_2\text{--}Q\text{-} \qquad \qquad I''$$

wherein Q is independently selected from the group consisting of oxygen or sulfur, said constituting a portion of the residue derived from: (1) beta-hydroxy thioether reactant, (2) the hydrocarbyl portion of organic phosphite reactant, (3) the nucleophilic reactant, and (4) mixtures of (1) to (3); and wherein the remainder of Structure I'' exclusive of Q, contains residue of beta-hydroxy thioether reactant; and (ii) phosphorous compounds comprising phosphorous acid and organic phosphates having within their structure at least one group represented by the formula:

$$R\text{-}SCH_2CH_2O\text{--} \qquad \qquad I'$$

bonded directly to the phosphorous atom of the organic phosphite said $R\text{-}SCH_2CH_2O\text{--}$ group representing a residue of beta-hydroxy thioether; and (2) cause the product mixture to separate into a top phase an a bottom phase, with said top phase comprising a major amount of said non-phosphorous containing compounds and said bottom phase comprising a major amount of said phosphorous containing compounds; and (C) separating the top phase from the bottom phase.

111. The process of claim 110 wherein the nucleophilic reactant is represented by at least one of the formulas:

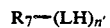

$$R_7\text{--}(LH)_{n'} \qquad \qquad IV$$

and

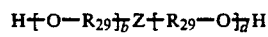

$$H\text{--}(\text{O}\text{--}R_{29})_b\text{--}Z\text{--}(R_{29}\text{--}O)_d\text{--}H \qquad \qquad IV'$$

wherein $R_7$ represents an inertly substituted or unsubstituted hydrocarbyl group; L represents at least one member selected from the group consisting of oxy, oxyalkylene, polyoxyalkylene, and poly(oxyalkylene)thio; n' is a number of from 1 to about 3 and represents the number of -LH groups attached to $R_7$; $R_{29}$ is independently $C_2$ to about $C_4$ alkylene; Z is selected $-S-$, $-S-S-$, $-O-$, $>NR_{10}$ wherein $R_{10}$ is H, $C_1$ to $C_{22}$ alkyl, or monohydroxy $C_1$ to $C_{12}$ alkyl; and (b) and (d), independently, are from 1 to 3, with the proviso that the identity of $R_{29}$, b and d is selected such that the compound represented by formula IV' does not contain an $-SCH_2CH_2OH$ group.

112. The process of claim 110, wherein said nucleophilic reactant may be represented by at least one of the formulas:

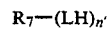

$$R_7\text{--}(LH)_{n'} \qquad \qquad IV$$

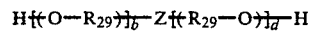

$$H\text{--}(\text{O}\text{--}R_{29})_b\text{--}Z\text{--}(R_{29}\text{--}O)_d\text{--}H \qquad \qquad IV'$$

$$R_7\text{--}[Z\text{--}(R_{29}\text{--}O)_{n''}H]_{n'''} \qquad \qquad IV''$$

wherein $R_7$ represents an inertly substituted or unsubstituted aliphatic hydrocarbyl group having from 6 to 22 carbons; L represents oxygen; Z is $-S-$ or $-S-S-$; n' is a number of from 1 to about 3 and represents the number of -LH groups attached to $R_7$; n'' is a number of from 2 to about 4; $R_{29}$ is $C_2$ to about $C_4$ alkylene; and n''' is a number of from about 1 to about 3 and represents the number of $[Z\text{-}R_{29}\text{--}O)_{n''}H]$ groups attached to $R_7$.

113. The process of claim 110, wherein said nucleophilic reactant may be represented by the formula:

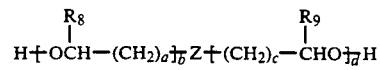

$$H\text{--}(\text{OCH}\text{--}(CH_2)_a)_b\text{--}Z\text{--}((CH_2)_c\text{--}CHO)_d\text{--}H \qquad V$$
with $R_8$ and $R_9$ substituents wherein $R_8$ and $R_9$, each independently, represent H or $C_1$-$C_{12}$ alkyl; Z is selected from —S—, —S—S—, —O— and >$NR_{10}$, wherein $R_{10}$ is H, $C_1$-$C_{22}$ alkyl, or monohydroxy-substituted $C_1$-$C_{12}$ alkyl; a, b, c, and d, each, independently, represents the same or different number of from about 1 to about 3 with the proviso that a+b, and c+d, are each at least 3.

114. The process of claim 113, wherein, in said nucleophilic reactant, $R_8$ and $R_9$ are H; a and c are 1, b and d are 2; and Z is —S—.

115. The process of claim 110, wherein said nucleophilic reactant is formed in situ and is derived from the hydrocarbyl portion of at least one of said hydrocarbyl phosphite reactants.

116. The process of claim 110 wherein:
(1) in structural formula I, R represents a member selected from the group consisting of: $C_1$-$C_{30}$ aliphatic hydrocarbyl; $C_6$-$C_{14}$ aromatic hydrocarbyl; mixed aromatic/aliphatic hydrocarbyl wherein the aromatic and aliphatic portions thereof are as described immediately above; -$R_1$OH or -$SR_1$OH, wherein $R_1$ is independently as described in connection with R as aliphatic, aromatic, and mixed aliphatic/aromatic;
(2) the phosphorous-containing reactant is selected from the group consisting of organic phosphite esters having at least one of the following formulas:

$$P(OR_5)_3 \qquad \text{II}$$

$$\underset{H-P-(OR_5)_2}{\overset{O}{\|}} \qquad \text{III}$$

wherein $R_5$, independently, represents the same or different $C_1$-$C_{30}$ straight chain aliphatic group or the group

III'

(with $(R_6)_n$ on phenyl ring)

wherein $R_6$, independently, represents the same or different $C_1$-$C_{24}$ hydrocarbyl group or H; n is a number from 1 to 3; and wherein $R_5$ and $R_6$ may be inertly substituted.

117. The process of claim 116, wherein x is 1; and R represents at least one member selected from the group consisting of $C_1$-$C_{30}$ alkyl; $C_6$-$C_{14}$ aryl; alkaryl or aralkyl wherein the alkyl and aryl portions thereof are as described immediately above; -$R_1$OH, -$SR_1$OH, or $$-(R_{22})_z-\left[\begin{array}{c} R_{12}-O \\ | \\ R_{13} \end{array}\right]_m-H$$

wherein, $R_1$ and $R_{11}$, independently, are as described in connection with R as alkyl, aryl, aralkyl and alkaryl immediately above; $R_{12}$ is $C_2$ to $C_3$ alkanetriyl; $R_{13}$ is H or $C_1$-$C_{18}$ aliphatic hydrocarbyl; m is a number of from 1 to 6 and represents the number of repeating oxyalkylene groups; and z is 0 or 1.

118. The process of claim 117, wherein in said beta-hydroxy thioether R is $C_{10}$-$C_{14}$ alkyl.

119. The process of claim 117, wherein in said beta-hydroxy thioether x is 1; R is selected from the group consisting of $C_8$ to $C_{15}$ alkyl, -$R_1$OH, $$-(R_{22})_z-\left[\begin{array}{c} R_{12}-O \\ | \\ R_{13} \end{array}\right]_m-H$$

and mixtures thereof, and wherein $R_1$ is $C_8$ to $C_{15}$ alkyl; $R_{12}$ is $C_2$ alkanetriyl, $R_{13}$ is H, z is 0, and m is a number of from 1 to 3.

120. The process of claim 117, wherein, in said phosphorous-containing reactant, each $R_5$, independently, represents $C_2$-$C_4$ alkyl, or phenyl.

121. The process of claim 120, wherein each $R_5$ is the same.

122. The process of any one of claims 110 to 121, wherein said admixture in step (A) comprises at least about twenty mole percent of phosphorous-containing reactant, based on the total moles of reactants in the reaction mixture.

123. The process of any one of claims 110 to 121, wherein said admixture in step (A) comprises from about 20 to 50 mole percent of phosphorous-containing reactant, based on the total moles of reactants in the reaction mixture.

124. The process of any one of the claims 110 to 121 wherein the oleaginous composition is a power transmission fluid.

125. The process of claim 124, wherein the power transmission fluid composition is an automatic transmission fluid.

126. The process according to any one of claims 110 to 121 wherein said oleaginous composition comprises from about 0.01 to about 25 weight percent of said phosphorous containing additive.

127. The process of any one of claims 75 to 121, and which comprises admixing with said oleaginous material at least one dispersant additive and at least one friction modifying additive.

128. The process of claim 127, wherein said friction modifying additive is characterized by at least one of the following formulas:

$$\underset{R_{16}-(X)_q-R_{17}-N}{\overset{R_{15}}{|}} \diagup^{(R_{18}O)_rH}_{\diagdown (R_{19}O)_rH} \qquad \text{XI}$$

$$\underset{R_{16}-(X)_q-R_{17}-N-R_{21}-N}{\overset{R_{15}}{|}} \diagup^{(R_{18}O)_rH}_{\diagdown (R_{19}O)_rH} \qquad \text{XII}$$

with $R_{20}OH$ on the middle N wherein $R_{15}$ represents H or $CH_3$; $R_{16}$ represents a $C_3$-$C_{27}$ saturated or unsaturated aliphatic hydrocarbyl radical; $R_{17}$ and $R_{20}$, independently, represent the same or different straight or branched chain $C_2$-$C_6$ alkylene radical; $R_{18}$ and $R_{19}$, independently, represent the same or different straight or branched chain $C_1$-$C_5$ alkylene radical; $R_{21}$ represents a straight or branched chain $C_1$-$C_5$ alkylene radical; X represents O or S; q represents 0 or 1; and r, independently, represents the same or different number of from about 1 to about 4.

129. The process of claim 128, wherein said dispersant additive comprises a borated or unborated polyisobutenyl succinimide.

130. A process for preparing phosphorous- and sulfur containing reaction products comprising:
 (A) providing an admixture comprising:
  (1) at least one beta-hydroxy thioether reactant represented by the formula:

$$R\text{-}(SCH_2CH_2OH)_x \qquad \qquad I$$

wherein R represents an unsubstituted or substituted hydrocarbyl group and wherein x is a number from 1 to about 3 and identifies the number of -SCH$_2$CH$_2$OH groups attached to R;
  (2) an amount of phosphorous-containing reactant selected from the group consisting of dihydrocarbyl hydrogen phosphite, trihydrocarbyl phosphite, and mixtures thereof, sufficient to provide at least about ten mole percent of phosphorous containing reactant based on the total moles of reactants in said reaction mixture; and
  (3) a nucleophilic reactant containing at least one reactive hydroxy group and being free from any reactive mercapto or -SCH$_2$CH$_2$OH groups;
 (B) heating the admixture prepared in accordance with Step (A) in a manner and under conditions sufficient to:
  (1) cause the beta-hydroxy thioether to react with the phosphorous containing reactant to form a product mixture comprising:
   (i) non-phosphorous containing compounds having within their structure at least one group represented by the formula:

$$\text{-S}\text{—}CH_2CH_2\text{—}Q\text{-} \qquad \qquad I''$$

wherein Q is independently selected from the group consisting of oxygen or sulfur, said Q constituting a portion of the residue derived from: (1) beta-hydroxy thioether reactant, (2) the hydrocarbyl portion of the organic phosphite reactant, (3) the nucleophilic reactant, and (4) mixtures of (1) to (3); and wherein the remainder of Structure I'' exclusive of Q, contains residue of beta-hydroxy thioether reactant; and
   (ii) phosphorous containing compounds comprising phosphorous acid and organic phosphites having within their structure at least one group represented by the formula:

$$R\text{-}SCH_2CH_2O\text{—} \qquad \qquad I'$$

bonded directly to the phosphorous atom of the organic phosphite said R-SCH$_2$CH$_2$O group representing a residue of beta-hydroxy thioether.

131. The process of claim 130 wherein the nucleophilic reactant is represented by at least one of the formulas:

$$R_7\text{—}(LH)_{n'} \qquad \qquad IV$$

and $$H\text{+}O\text{—}R_{29}\text{)}_{\overline{b}}Z\text{+}R_{29}\text{—}O\text{)}_{\overline{d}}H \qquad \qquad IV'$$

wherein R$_7$ represents an inertly substituted or unsubstituted hydrocarbyl group; L represents at least one member selected from the group consisting of oxy, oxyalkylene, polyoxyalkylene, and poly(oxyalkylene)thio; n' is a number of from 1 to about 3 and represents the number of -LH groups attached to R$_7$; R$_{29}$ is independently C$_2$ to about C$_4$ alkylene; Z is selected from —S—, —S—S—, —O—, >NR$_{10}$ wherein R$_{10}$ is H, C$_1$ to C$_{22}$ alkyl, or monohydroxy C$_1$ to C$_{12}$ alkyl; and (b) and (d), independently, are from 1 to 3, with the proviso that the identity of R$_{29}$, b and d is selected such that the compound represented by formula IV' does not contain an -SCH$_2$CH$_2$OH group.

132. The process of claim 130, wherein said nucleophilic reactant may be represented by at least one of the formulas:

$$R_7\text{—}(LH)_{n'} \qquad \qquad IV$$

$$H\text{+}O\text{—}R_{29}\text{)}_{\overline{b}}Z\text{+}R_{29}\text{—}O\text{)}_{\overline{d}}H \qquad \qquad IV'$$

$$R_7\text{+}Z\text{—}(R_{29}\text{—}O)_{n''}H]_{n'''} \qquad \qquad IV'''$$

wherein R$_7$ represents an inertly substituted or unsubstituted aliphatic hydrocarbyl group having from 6 to 22 carbons; L represents oxygen; Z is —S— or —S—S—; n' is a number of from 1 to about 3 and represents the number of -LH groups attached to R$_7$; n'' is a number of from 2 to about 4; R$_{29}$ is C$_2$ to about C$_4$ alkylene; and n''' is a number of from about 1 to about 3 and represents the number of [Z-(R$_{29}$—O)$_{n''}$H] groups attached to R$_7$.

133. The process of claim 130, wherein said nucleophilic reactant may be represented by the formula:

$$\begin{array}{cc} R_8 & R_9 \\ | & | \\ H\text{+}OCH\text{—}(CH_2)_a\text{)}_{\overline{b}}Z\text{+}(CH_2)_c\text{—}CHO\text{)}_{\overline{d}}H \end{array} \qquad V$$

wherein R$_8$ and R$_9$, each independently, represent H or C$_1$-C$_{12}$ alkyl; Z is selected from —S—, —S—S—, —O— and >NR$_{10}$, wherein R$_{10}$ is H, C alkyl, or monohydroxy-substituted C$_1$-C$_{12}$ alkyl; a, b, c, and d, each, independently, represents the same or different number of from about 1 to about 3 with the proviso that a+b, and c+d, are each at least 3.

134. The process of claim 133, wherein, in said nucleophilic reactant, R$_8$ and R$_9$ are H, a and c are 1, b and d are 2; and Z is —S—.

135. The process of claim 130, wherein said nucleophilic reactant is formed in situ and is derived from the hydrocarbyl portion of at least one of said hydrocarbyl phosphite reactants.

136. The process of claim 130, wherein the reaction mixture is heated at a temperature of from about 75° to about 130° C. for a period of from about 1 to about 24 hours.

137. The process of claim 130, wherein said heating step is continued for a period of time such that the hydrogen phosphite peak of said mixture of reaction products at 4.1 u has exceeded the hydroxide peak when tested by infrared analysis.

138. The process of claim 130 wherein:
 (1) in structural formula I, R represents a member selected from the group consisting of: C$_1$-C$_{30}$ aliphatic hydrocarbyl; C$_6$-C$_{14}$ aromatic hydrocarbyl; mixed aromatic/aliphatic hydrocarbyl wherein the aromatic and aliphatic portions thereof are as described immediately above; -R$_1$OH or -SR$_1$OH, wherein R$_1$ is independently as described in connection with R as aliphatic, aromatic, and mixed aliphatic/aromatic;

(2) the phosphorous-containing reactant is selected from the group consisting of organic phosphite esters having at least one of the following formulas:

 II

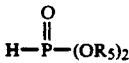 III wherein $R_5$, independently, represents the same or different $C_1$-$C_{30}$ straight chain aliphatic group or the group

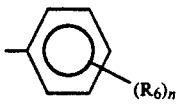 III' wherein $R_6$, independently, represents the same or different $C_1$-$C_{24}$ hydrocarbyl group or H; n is a number from 1 to 3; and wherein $R_5$ and $R_6$ may be inertly substituted.

139. The process of claim 138, wherein x is 1; and R represents at least one member selected from the group consisting of $C_1$-$C_{30}$ alkyl; $C_6$-$C_{14}$ aryl; alkaryl or aralkyl wherein the alkyl and aryl portions thereof are as described immediately above; -$R_1$OH, -$SR_1$OH, or

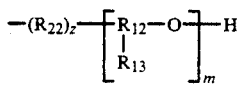

wherein, $R_1$ and $R_{11}$, independently, are as described in connection with R as alkyl, aryl, aralkyl and alkaryl immediately above; $R_{12}$ is $C_2$ to $C_3$ alkanetriyl; $R_{13}$ is H or $C_1$-$C_{18}$ aliphatic hydrocarbyl; m is a number of from 1 to 6 and represents the number of repeating oxyalkylene groups; and z is 0 or 1.

140. The process of claim 139 wherein in said beta-hydroxy thioether R is $C_{10}$-$C_{14}$ alkyl.

141. The process of claim 139, wherein in said beta-hydroxy thioether x is 1; R is selected from the group consisting of $C_8$ to $C_{15}$ alkyl, -$R_1$OH,

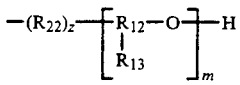

and mixtures thereof, and wherein $R_1$ is $C_8$ to $C_{15}$ alkyl; $R_{12}$ is $C_2$ alkanetriyl, $R_{13}$ is H, z is 0, and m is a number of from 1 to 3.

142. The process of claim 139, wherein, in said phosphorous-containing reactant, each $R_5$, independently, represents $C_2$-$C_4$ alkyl, or phenyl.

143. The process of claim 142 wherein each $R_5$ is the same.

144. The composition of any one of claims 130 to 143, wherein said admixture in step (A) comprises from about 20 to about 50 mole percent of phosphorous-containing reactant, based on the total number of moles of reactants in said reaction mixture.

145. The process of any one of claim 130 to 143 wherein the reaction is conducted for a period and at a temperature sufficient to cause the reaction mixture to separate into a top phase and a bottom phase, whereby the top phase comprises a major amount of said non-phosphorous containing compounds and the bottom phase comprises a major amount of said phosphorous containing compounds.

146. The process of claim 145 wherein the top phase is separated from the bottom phase.

147. The process of claim 145 wherein the reaction temperature is from about 75° to about 130° C. and the reaction time at said temperature is from about 1 to about 24 hours.

148. The process of any one of claims 130 to 143, wherein at least about 20 mole of phosphorous-containing reactant are employed in the admixture provided in step (A).

149. A hydrocarbon soluble or dispersible mixture of compounds comprising phosphorous- and sulfur-containing reaction products prepared by reacting in admixture:

(1) organic phosphite ester having the formula II:

 II wherein $R_5$, independently, represents the same or different $C_1$-$C_5$ saturated or unsaturated, straight or branched chain aliphatic hydrocarbyl radical or the aromatic radical:

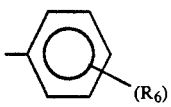 III' wherein $R_6$ represents H or $C_1$-$C_4$ alkyl, and n is an integer from 1 to 3;

(2) hydrocarbyl thioalkanol having at least one of the following formulas VI' or VI":

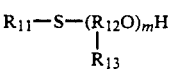 VI'

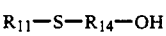 VI"

wherein $R_{11}$ represents a $C_8$-$C_{30}$ saturated or unsaturated, straight or branched chain hydrocarbyl radical having at most two unsaturated linkages; $R_{12}$ represents a $C_2$-$C_3$ alkanetriyl radical; $R_{13}$ represents H or a $C_1$-$C_{18}$ saturated or unsaturated, straight or branched chain hydrocarbyl radical; $R_{14}$ represents a $C_2$-$C_{30}$ saturated or unsaturated, straight or branched chain hydrocarbyl radical; and m represents a number of from about 1 to 6; and (3) heterodialkanol having the following formula V:

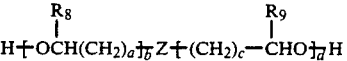 V wherein $R_8$ and $R_9$ each independently represent hydrogen, or a $C_1$-$C_{12}$ alkyl; Z is a linking group selected from —S—, —S—S—, —O—, and >$NR_{10}$, wherein $R_{10}$ is hydrogen, $C_1$-$C_{22}$ alkyl, or monohydroxy-substituted $C_1$-$C_{12}$ alkyl; and a, b, c and d each independently represents the same or different integer 1-3; said reaction having been conducted at a temperature of from about 75° to about 130° C. for a period of from about 1 to about 10 hours, with the proviso that at least one of the hydrocarbon thioalkanol and heterodialkanol reactants contains an -SCH$_2$CH$_2$OH group, and that the organic phosphite reactant is employed in an amount sufficient to provide at least about ten mole percent of said organic phosphite reactant in said admixture based on the total number of moles of organic phosphite, hydrocarbyl thioalkanol and heterodialkanol reactants present therein.

150. A hydrocarbon soluble or dispersible mixture of compounds comprising phosphorous- and sulfur-containing reaction products prepared by reacting in admixture:
(1) at least about ten mole percent, based on the total number of moles of reactants in said admixture, of organic phosphite ester having the formula:

P(OR$_5$)$_3$      II wherein R$_5$, independently, represents the same or different C$_1$-C$_5$ saturated or unsaturated, straight or branched chain aliphatic hydrocarbyl radical or the aromatic radical:

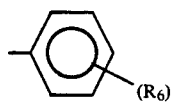
     III' wherein R$_6$, independently, represents H or the same or different C$_1$-C$_4$ alkyl, and n is an integer from 1 to 3;
(2) hydrocarbyl thioalkanol comprising a compound represented by the formula:

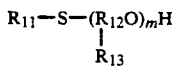
     VI' wherein R$_{11}$ represents C$_8$-C$_{30}$ saturated or unsaturated, straight or branched chain hydrocarbyl radical having at most two unsaturated linkages; R$_{12}$ represents a C$_2$-C$_3$ alkanetriyl radical; R$_{13}$ represents H or a C$_1$-C$_{18}$ saturated or unsaturated, straight or branched chain hydrocarbyl radical; and m represents a number of from 1 to about 6; and
(3) heterodialkanol comprising a compound having the formula V:

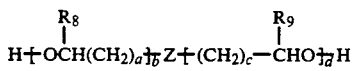
     V wherein R$_8$ and R$_9$, each independently, represent H or C$_1$-C$_{12}$ alkyl; a, b, c and d each, independently, represent the same or different number 1-3; and Z is —S— or —S—S—; said reaction having been conducted at a temperature of from about 75° to about 130° C., with the proviso that at least one -SCH$_2$CH$_2$OH group appears in the structure of at least one of reactants V and VI'.

151. The hydrocarbon soluble or dispersible mixture of compounds prepared in accordance with claim 150 wherein the ratio of total molar equivalents of hydroxyl groups in the said hydrocarbyl thioalkanol reactant and said heterodialkanol reactant collectively to the moles of phosphorous contained in said phosphite reactant in the reaction mixture is from about 1 to 5:1.

152. A hydrocarbon soluble or dispersible mixture of compounds comprising phosphorous- and sulfur-containing reaction products prepared by reacting in admixture:
(1) at least about ten mole percent, based on the total moles of reactants employed in said admixture, of organic phosphite ester having the formula:

P(OR$_5$)$_3$      II wherein R$_5$, independently, represents the same or different C$_1$-C$_5$ saturated or unsaturated, straight or branched chain aliphatic hydrocarbyl radical or the aromatic radical:

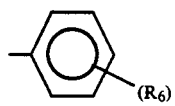
     III' wherein R$_6$, independently, represents H or the same or different C$_1$-C$_4$ alkyl, and n is an integer of from 1 to
(2) hydrocarbyl thioalkanol comprising a compound represented by the formula:

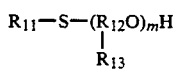
     VI' wherein R$_{11}$ represents C$_8$-C$_{30}$ saturated or unsaturated, straight or branched chain hydrocarbyl radical having at most two unsaturated linkages; R$_{12}$ represents a C$_2$ alkanetriyl radical; R$_{13}$ represents H or a C$_1$-C$_{18}$ saturated or unsaturated, straight or branched chain hydrocarbyl radical; and n represents a number of from 1 to about 6; and
(3) heterodialkanol comprising a compound having the formula V:

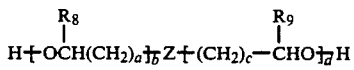
     V wherein R$_8$ and R$_9$, each independently, represent H or C$_1$-C$_{12}$ alkyl; a, b, c and d each, independently, represent the same or different number 1-3; and Z is —S— or —S—S—, with the proviso that at least one of the hydrocarbyl thioalkanol and the heterodialkanol reactants contains at least one -SCH$_2$CH$_2$OH group; said reaction having been conducted at a temperature of from about 75° to about to about 130° C.

153. The mixture of any one of claims 149 to 152, wherein in said organic phosphite ester, each R$_5$, independently, represents a C$_2$-C$_4$ alkyl or phenyl radical.

154. The mixture of claim 153, wherein each R$_5$ represents the same radical.

155. The mixture of any one of claims 150 to 152, wherein in said hydrocarbyl thioalkanol R$_{11}$ is C$_{10}$-C$_{14}$ alkyl, R$_{12}$ is C$_2$ alkanetriyl, R$_{13}$ is H, and n is 1.

156. The mixture of claim 155, wherein, in said heterodialkanol, both $R_8$ and $R_9$ are H, each of a, b, c and d, is 1 and Z is —S—.

157. An oleaginous composition comprising an oleaginous material selected from the group consisting of fuels and lubrication oils, and the mixture of sulfur- and phosphorous-containing reaction products prepared according to any one of claims 151 to 152.

158. The oleaginous composition of claim 157, which is adaptable for use as a power transmission fluid and which further comprises an effective amount of at least one of each of (a) dispersant additive and (b) friction modifying additive.

159. The oleaginous composition of claim 158, wherein said dispersant additive comprises ashless dispersant.

160. The oleaginous composition of claim 159, where said ashless dispersant comprises borated or unborated, aminated, long chain hydrocarbyl-substituted dicarboxylic acid material.

161. The oleaginous composition of claim 160, wherein said dispersant comprises borated or unborated polyisobutenyl succinimide.

162. The oleaginous compositions of claim 161, wherein said friction modifying additive is characterized by at least one of the following formulas:

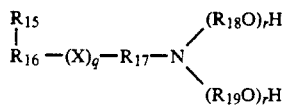

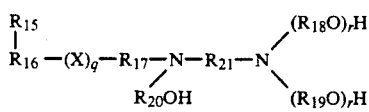

wherein $R_{15}$ represents H or $CH_3$; $R_{16}$ represents a $C_3$-$C_{27}$ saturated or unsaturated aliphatic hydrocarbyl radical; $R_{17}$ and $R_{20}$, independently, represent the same or different straight or branched chain $C_2$-$C_6$ alkylene radical; $R_{18}$ and $R_{19}$, independently, represent the same or different straight or branched chain $C_1$-$C_5$ alkylene radical; $R_{21}$ represents a straight or branched chain $C_1$-$C_5$ alkylene radical; X represents O or S; q represents 0 or 1; and r, independently, represents the same or different number of from about 1 to about 4.

163. A lubricating oil composition adaptable for use as an automatic transmission fluid which comprises mineral oil and an amount of an additive mixture effective to impart at least one of the properties of anti-wear and anti-oxidation to said fluid relative to the absence of said additive mixture, said additive mixture comprising the hydrocarbon soluble mixture of compounds of any one of claims 149 to 152.

164. The lubricating oil composition of claim 163 which further comprises an effective amount of at least one of each of (a) dispersant additive and (b) friction modifying additive.

165. The lubricating oil composition of claim 164, wherein said dispersant additive comprises ashless dispersant.

166. The lubricating oil composition of claim 165, where said ashless dispersant comprises borated or unborated, aminated, long chain hydrocarbyl-substituted dicarboxylic acid material.

167. The lubricating oil composition of claim 166, wherein said dispersant comprises borated or unborated polyisobutenyl succinimide.

168. The lubricating oil composition of claim 167, wherein said friction modifying additive is characterized by at least one of the following formulas:

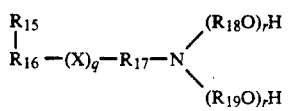

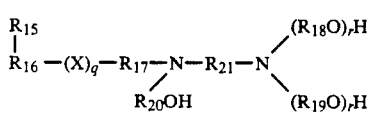

wherein $R_{15}$ represents H or $CH_3$; $R_{16}$ represents a $C_3$-$C_{27}$ saturated or unsaturated aliphatic hydrocarbyl radical; $R_{17}$ and $R_{20}$, independently, represent the same or different straight or branched chain $C_2$-$C_6$ alkylene radical; $R_{18}$ and $R_{19}$, independently, represent the same or different straight or branched chain $C_1$-$C_5$ alkylene radical; $R_{21}$ represents a straight or branched chain $C_1$-$C_5$ alkylene radical; X represents O or S; q represents 0 or 1; and r, independently, represents the same or different number of from about 1 to about 4.

169. The oleaginous composition of claims 137 to 168 wherein said mixture of sulfur- and phosphorous-containing reaction products is present in said composition to the extent of from about 0.01 to about 25 weight percent.

* * * * *